(12) United States Patent
Elokdah et al.

(10) Patent No.: US 7,074,817 B2
(45) Date of Patent: Jul. 11, 2006

(54) SUBSTITUTED INDOLE ACID DERIVATIVES AS INHIBITORS OF PLASMINOGEN ACTIVATOR INHIBITOR-1 (PAI-1)

(75) Inventors: Hassan Mahmoud Elokdah, Yardley, PA (US); Geraldine Ruth McFarlane, Monmouth Junction, NJ (US); David Zenan Li, Princeton, NJ (US); Lee D. Jennings, Chestnut Ridge, NY (US); David LeRoy Crandall, Doylestown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/174,159

(22) Filed: Jun. 18, 2002

(65) Prior Publication Data

US 2003/0125371 A1 Jul. 3, 2003

Related U.S. Application Data

(60) Provisional application No. 60/299,657, filed on Jun. 20, 2001.

(51) Int. Cl.
*A61K 31/404* (2006.01)
*C07D 209/42* (2006.01)

(52) U.S. Cl. .................. 514/419; 548/493; 548/494
(58) Field of Classification Search ............. 548/493, 548/494; 514/419
See application file for complete search history.

(56) References Cited

U.S. PATENT DOCUMENTS

| 3,026,325 A | * | 3/1962 | Heinzelman et al. ....... 548/496 |
| 3,476,770 A | | 11/1969 | Scherrer |
| 3,557,142 A | | 1/1971 | Bell ............................ 548/516 |

(Continued)

FOREIGN PATENT DOCUMENTS

| DE | 3147276 A1 | 11/1981 |
| DE | 43 38 770 A1 | 5/1995 |
| DE | 19543639 A1 | 5/1997 |
| DE | 19753522 A1 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 A2 | 4/2001 |
| EP | 1 092 716 A | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | WO 96/32379 A1 | 10/1996 |
| WO | 97/09308 A1 | 3/1997 |
| WO | 97/43260 A1 | 11/1997 |
| WO | 97/48697 A1 | 12/1997 |
| WO | 98/08818 A1 | 3/1998 |
| WO | WO 99/28297 A1 | 6/1999 |
| WO | WO 99/43651 A2 | 9/1999 |
| WO | WO 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |

(Continued)

OTHER PUBLICATIONS

Julia et al., CA 57:49169, 1962.*
Moody et al., CA 120:298300, 1994.*
Delgado et al., Journal of Organic Chemistry (1993), 58(10), pp. 2862–2866.*

(Continued)

*Primary Examiner*—Laura L. Stockton
(74) *Attorney, Agent, or Firm*—Woodcock Washburn LLP

(57) ABSTRACT

This invention provides compounds of the formula:

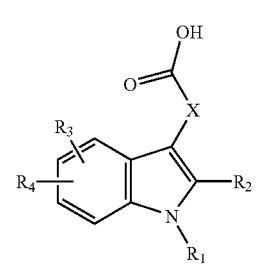

(I)

wherein: X is a chemical bond, —$CH_2$— or —C(O)—; $R_1$ is alkyl, cycloalkyl, —$CH_2$-cycloalkyl, pyridinyl, —$CH_2$-pyridinyl, phenyl or benzyl; $R_2$ is H, alkyl, cycloalkyl, —$CH_2$-cycloalkyl, or perfluoroalkyl; $R_3$ is H, halo, alkyl, perfluoroalkyl, alkoxy, cycloalkyl, —$CH_2$-cycloalkyl, —$NH_2$, or —$NO_2$; $R_4$ is optionally substituted phenyl, benzyl, benzyloxy, pyridinyl, or —$CH_2$-pyridinyl, or the salt or ester forms thereof, as well as methods for using the compounds as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

22 Claims, No Drawings

U.S. PATENT DOCUMENTS

| | | | |
|---|---|---|---|
| 3,843,683 A | 10/1974 | Bell | 548/493 |
| 4,478,819 A | 10/1984 | Hercelin et al. | 424/457 |
| 4,736,043 A | 4/1988 | Michel et al. | 548/492 |
| 4,851,406 A | 7/1989 | Mertens et al. | |
| 5,164,372 A | 11/1992 | Matsuo et al. | 514/19 |
| 5,420,289 A * | 5/1995 | Musser et al. | 548/159 |
| 5,482,960 A | 1/1996 | Berryman et al. | 514/414 |
| 5,502,187 A | 5/1996 | Ayer et al. | 544/117 |
| 5,541,343 A | 7/1996 | Himmelsbach et al. | 514/424 |
| 5,612,360 A | 3/1997 | Boyd et al. | 514/381 |
| 5,859,044 A | 1/1999 | Dow et al. | 514/419 |
| 6,048,875 A | 4/2000 | De Nanteuil et al. | 514/314 |
| 6,110,963 A | 8/2000 | Malamas | 514/443 |
| 6,166,069 A | 12/2000 | Malamas et al. | 514/469 |
| 6,232,322 B1 | 5/2001 | Malamas et al. | 514/303 |
| 6,251,936 B1 | 6/2001 | Wrobel et al. | 514/443 |
| 6,302,837 B1 | 10/2001 | De Nanteuil et al. | 514/337 |
| 6,479,524 B1 | 11/2002 | Priepke et al. | 514/352 |
| 6,599,929 B1 | 7/2003 | Cho et al. | 514/415 |
| 6,787,556 B1 | 9/2004 | Hargreaves et al. | 514/311 |
| 6,800,645 B1 | 10/2004 | Cox et al. | 514/314 |
| 6,800,654 B1 | 10/2004 | Mayer et al. | 514/381 |
| 6,844,358 B1 | 1/2005 | Malamas et al. | 514/336 |
| 2003/0013732 A1 | 1/2003 | Elokdah | 514/301 |
| 2003/0018067 A1 | 1/2003 | Elokdah et al. | 514/469 |
| 2003/0060497 A1 | 3/2003 | Gerlach | 514/414 |
| 2004/0116488 A1 | 6/2004 | Jennings et al. | 514/374 |
| 2004/0116504 A1 | 6/2004 | Elokdah et al. | 514/419 |
| 2004/0122070 A1 | 6/2004 | Jennings | 514/374 |
| 2004/0138283 A1 | 7/2004 | Jennings et al. | 514/414 |
| 2004/0204417 A1 | 10/2004 | Perez et al. | 514/249 |
| 2005/0119296 A1 | 2/2005 | Elokdeh et al. | 514/300 |
| 2005/0070585 A1 | 3/2005 | Elokdah et al. | 514/364 |
| 2005/0070587 A1 | 3/2005 | Elokdah et al. | 514/381 |
| 2005/0070592 A1 | 3/2005 | Gunderson | 514/415 |
| 2005/0096377 A1 | 5/2005 | Hu | 514/419 |
| 2005/0113428 A1 | 5/2005 | Gopalsamy et al. | 514/364 |
| 2005/0113436 A1 | 5/2005 | Elokdeh et al. | 514/411 |
| 2005/0113438 A1 | 5/2005 | Hu et al. | 514/414 |
| 2005/0113439 A1 | 5/2005 | Hu | 514/414 |
| 2005/0119326 A1 | 6/2005 | Harven et al. | 514/414 |
| 2005/0119327 A1 | 6/2005 | Hu | 514/414 |
| 2005/0215626 A1 | 9/2005 | Harven et al. | 514/469 |

FOREIGN PATENT DOCUMENTS

| | | |
|---|---|---|
| WO | WO 00 35919 A | 6/2000 |
| WO | 00/46195 A1 | 8/2000 |
| WO | 00/046197 A1 | 8/2000 |
| WO | 00/64876 A1 | 11/2000 |
| WO | 00/64888 A1 | 11/2000 |
| WO | 01/12187 A2 | 2/2001 |
| WO | 02/030895 A1 | 4/2002 |
| WO | 02/072549 A1 | 9/2002 |
| WO | 03/000253 A1 | 1/2003 |
| WO | 03/031409 A1 | 4/2003 |
| WO | 03/068742 A2 | 8/2003 |
| WO | 03/087087 A2 | 10/2003 |
| WO | 2004/052854 A2 | 6/2004 |

OTHER PUBLICATIONS

Nordt et al., The Journal of Clinical Endocrinology & Metabolism, 85(4), 1563–1568 (2000).
Aznar et al., Haemostasis, 24, 243–251 (1994).
Carmeliet et al., Journal of Clinical Invest., 92, 2756–2760 (1993).
Daci et al., Journal of Bone & Mineral Research, 15(8), 1510–1516 (2000).
Biemond et al., Circulation, 91(4), 1175–1181 (1995).
Levi, et al., Circulation, 85(1), 305–312 (1992).
Rocha, et al., Fibrinolysis, 8, 294–303 (1994).
Reilly et al., Arteriosclerosis & Thrombosis 11, 1276–1286 (1991).
Krishnamurti et al., Blood, 69(3), 798–803 (1987).
Dillard R. D. et al: Indole Inhibitors of Human Nonpancreatic Secretory Phospholipase A21. Indole–3–Acetamides Journal of Medicinal Chemistry, American Chemical Society, Washington, US, vol. 39, No. 26, Dec. 20, 1996, pp. 5119–5136, XP002046054, ISSN: 0022–2623, Scheme 3 compounds 9c, 9h.
Crandall, D. L. et al., "Characterization and comparative evaluation of a structurally unique PAI–1 inhbitor exhibiting oral in–vivo efficacy," *Journal of Thrombosis and Haemostasis,* Mar. 17, 2004, 2, 1422–1428.
Guzzo, P.R. et al., "Synthesis of a confomationally constrained threonin–valine dipeptide mimetic: design of a potential inhibtor of plasminogen activator inhibtor–1," *Tetrahedron Letters,* 2002 43(1), 41–43.
Charlton, Peter, "The status of plasminogen activator inhibitor–1 as a therapuetic target," *Expert Opinion On Investigational Drugs,* May 1997, 6(5), 539–554.
Malamas, M. S. et al., "Antihyperglycemic activity of new 1,2,4–oxadiazolidine–3–5–diones," *Eur. J. Med. Chem.,* 2001, 36, 31–42.
U.S. Appl. No. 10/947,710, filed Sep. 23, 2004, Commons et al.
U.S. Appl. No. 10/947,711, filed Sep. 23, 2004, Gopalsamy et al.
Aggarwal et al., "A catalytic antibody programmed for torsional activation of amide bond hydrolysis," *Chem. Eur. J.,* Jan. 25, 2003, 9(13), 3132–3142.
Hipskind, P. A. et al., "Potent and selective 1,2,3–trusubstitued indole NPY Y–1 antagonists," *J Med Chem,* 1997, 40(23), 3712–3714.
Malamas, M. S. et al. "Novel benzofuran and benzothiophene biphenyls as inhibitors of protein tyrosine 1B with antihyperglycemic properties," *Journal of Medicinal Chemistry,* Apr. 6, 2000, 43(7), 1293–1310.
Shengeliya, M. S. et al., "N–Glycosides of 5–amino–2–(ethoxycarbonyl)indole," *Zhurnal Organicheskoi Khimii,* 1986, 22(9),1868–1873.
Ballantine, J. A., "The Chemistry of bacteria," Journal of the Chemical Society Abstracts, 1957, pp. 2222–2227.
De Settimo, A. "Reaction of indole with bromine," J Org Chem, 1970, 35(8):2546–2551.

* cited by examiner

SUBSTITUTED INDOLE ACID DERIVATIVES AS INHIBITORS OF PLASMINOGEN ACTIVATOR INHIBITOR-1 (PAI-1)

This application claims benefit of 60/299,657 filed Jun. 20, 2001.

This invention relates to the composition and utility of substituted indole derivatives as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (t-PA) and urokinase type plasminogen activator (u-PA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

WO 99/43654 and WO 99/43651 (American Home products Co.) teach indole derivatives of formula I as inhibitors phospholipase enzymes useful in preventing inflammatory conditions.

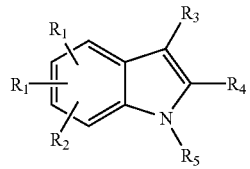

U.S. Pat. No. 4,851,406 (Boehringer Mannheim GmbH) claims cardiotonic compounds of formula I where:

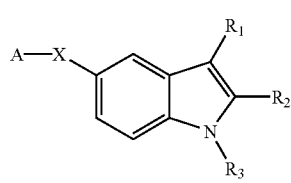

A is a five-membered, or six-membered ring heterocycle.

X is a bond, an alkylene, or a vinylene radical.

$R_1$ is a hydrogen, alkyl, alkenyl, cycloalkyl, cycloalkenyl, carboxyl, cyano, alkylcarbonyl, alkoxycarbonyl, aminocarbonyl, alkylaminocarbonyl, dialkylaminocarbonyl or aryl radical.

$R_2$ is a hydrogen, alkyl, trihalogenomethyl, hydroxyl, cycloalkyl, cyano, carboxyyl, etc. cloalkenyl, carboxyl, cyano, alkylcarbonyl, alkoxycarbonyl, aminocarbonyl, alkylaminocarbonyl, dialkylaminocarbonyl or aryl radical.

$R_3$ is a hydrogen atom.

WO 96/32379 (Fujisawa Pharmaceutical Co.) disclose PDE-inhibitor compounds of formula I where:

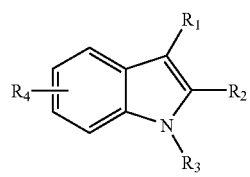

$R_1$ is a H, halo, nitro, carboxy, protected carboxy, lower alkenyl, or acyl; $R_2$ is a H, halo, carboxy, lower alkenyl, or acyl; $R_3$ is a lower alkenyl, or lower alkenyl, both optionally substituted; and $R_4$ is carboxy, protected carboxy, or acyl WO 9928297 (DE19753522) (Boehringer Ingelheim-Pharma KG) teaches substituted indoles of formula I with thrombin inhibiting effect and fibrinogen receptor antagonist effect.

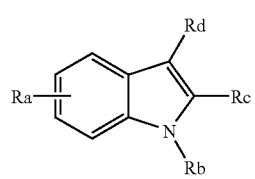

Wherein Ra is halogen, carboxy, $R_3R_4N$—CO—, $R_3R_4SO_2$—, or $R_4R_5N$—; Rb and Rd are either alkyl or $R_2$—A where $R_2$ is a phenyl optionally substituted and A is an alkylene or a substituted alkylene; and Rc is a hydrogen, or alkyl.

EP 0 655 439 (Eli Lilly and Company) discloses to 5, 6 fused ring bicyclic compounds inclusive of indoles, benzofurans, and benzothiophenes corresponding the general formula I as platelet aggregation inhibitors.

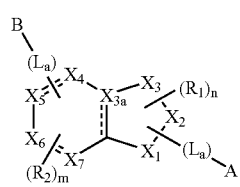

DESCRIPTION OF INVENTION

This invention comprises compounds of Formula I:

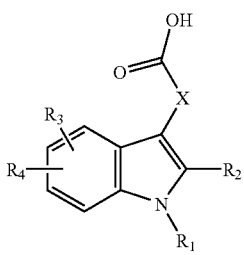

(I)

wherein:

X is a chemical bond, —CH₂— or —C(O)—;

R₁ is selected from $C_1$–$C_8$ alkyl, preferably $C_1$–$C_6$ alkyl, (—CH₂—)ₙ—$C_3$–$C_6$ cycloalkyl, wherein n is an integer of from 0 to 3, pyridinyl, —CH₂-pyridinyl, phenyl or benzyl, the rings of the cycloalkyl, pyridinyl, phenyl and benzyl groups being optionally substituted by, from 1 to 3 groups selected from, halogen, $C_1$–$C_4$ alkyl, $C_1$–$C_3$ perfluoroalkyl, preferably —CF₃, —O—$C_1$–$C_3$ perfluoroalkyl, preferably —O—CF₃, $C_1$–$C_3$ alkoxy, —OH, —NH₂, or —NO₂;

R₂ is selected from H, $C_1$–$C_6$ alkyl, $C_3$–$C_6$ cycloalkyl, —CH₂—$C_3$–$C_6$ cycloalkyl, or $C_1$–$C_3$ perfluoroalkyl, preferably —CF₃, —CH₂OH or CH₂OAc;

R₃ is selected from H, halogen, $C_1$–$C_6$ alkyl, $C_1$–$C_3$ perfluoroalkyl, preferably —CF₃, $C_1$–$C_6$ alkoxy, $C_3$–$C_6$ cycloalkyl, —CH₂—$C_3$–$C_6$ cycloalkyl, $C_3$–$C_6$ cycloalkenyl, —CH₂—$C_3$–$C_6$ cycloalkenyl, —NH₂, or —NO₂;

R₄ is selected from $C_3$–$C_6$ cycloalkyl, —CH₂—$C_3$–$C_6$ cycloalkyl, $C_3$–$C_6$ cycloalkenyl, —CH₂—$C_3$–$C_6$ cycloalkenyl, phenyl, benzyl, benzyloxy, pyridinyl, or —CH₂-pyridinyl, with the rings of these groups being optionally substituted by from 1 to 3 groups selected from halogen, $C_1$–$C_4$ alkyl, $C_1$–$C_3$ perfluoroalkyl, preferably —CF₃, —O—$C_1$–$C_3$ perfluoroalkyl, preferably —O—CF₃, $C_1$–$C_3$ alkoxy, —OH, —NH₂, —NO₂ or (CO)$C_1$–$C_6$ alkyl;

or a pharmaceutically acceptable salt or ester form thereof.

A subset of the compounds of this invention are those of the formulae:

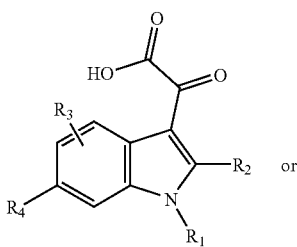

or

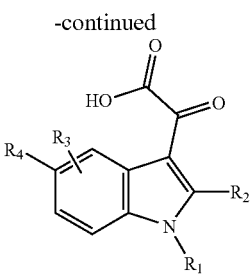

wherein R₁, R₂, R₃ and R₄ are as defined above, or a pharmaceutically acceptable salt or ester form thereof.

A further subset of the compounds of this invention comprises those having the formulae:

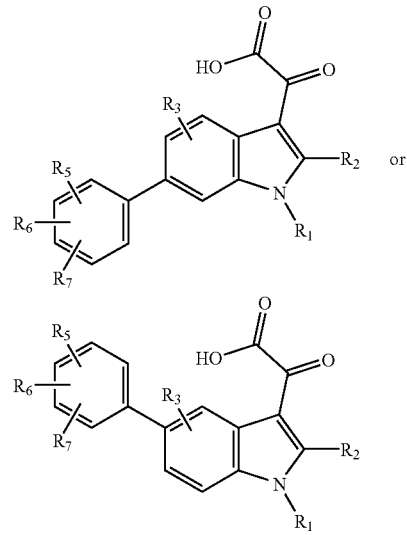

wherein:

R₁ is selected from $C_1$–$C_8$ alkyl, preferably $C_1$–$C_6$ alkyl, $C_3$–$C_6$ cycloalkyl, —CH₂—$C_3$–$C_6$ cycloalkyl, or benzyl, the rings of the cycloalkyl and benzyl groups being optionally substituted by from 1 to 3 groups selected from halogen, $C_1$–$C_3$ alkyl, $C_1$–$C_3$ perfluoroalkyl, preferably —CF₃, —O—$C_1$–$C_3$ perfluoroalkyl, preferably —O—CF₃, $C_1$–$C_3$ alkoxy, —OH, —NH₂, or —NO₂;

R₂ is selected from H, $C_1$–$C_6$ alkyl, $C_3$–$C_6$ cycloalkyl, —CH₂—$C_3$–$C_6$ cycloalkyl, or $C_1$–$C_3$ perfluoroalkyl, preferably —CF₃;

R₃ is selected from H, halogen, $C_1$–$C_6$ alkyl, $C_1$–$C_3$ perfluoroalkyl, preferably —CF₃, $C_1$–$C_6$ alkoxy, $C_3$–$C_6$ cycloalkyl, —CH₂—$C_3$–$C_6$ cycloalkyl, —NH₂, or —NO₂;

R₅, R₆ and R₇ are independently selected from H, halogen, $C_1$–$C_3$ alkyl, $C_1$–$C_3$ perfluoroalkyl, preferably —CF₃, —O—$C_1$–$C_3$ perfluoroalkyl, preferably —O—CF₃, $C_1$–$C_3$ alkoxy, —OH, —NH₂, or —NO₂;

or a pharmaceutically acceptable salt or ester form thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —$COOR_5$ wherein $R_5$ is selected from the formulae:

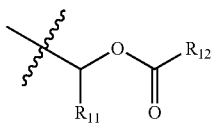

(1)

or

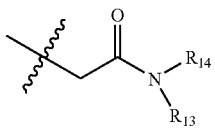

(2)

wherein $R_{11}$, $R_{12}$, $R_{13}$, $R_{14}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anti-coagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor—containing highly active antiretroviral therapy (HAART) for the treatment of diseases which orginate from fibrinolytic impairment and hyper-coagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

Process of the Invention

The compounds of the present invention can be readily prepared according to method A or method B as described in following reaction schemes or modification thereof using readily available starting materials, reagents and conventional synthetic procedures. It is also possible to make use of variants of these process steps, which in themselves are known to and well within the preparatory skill of the medicinal chemist. In the following reaction schemes, R, $R_1$, $R_2$, $R_3$, $R_4$ and $R_5$ are selected from the groups defined above.

The bromo-indoles (II) were either commercially available or were prepared following known literature procedures (Ayer et. al, *Tetrahedron Letters*, 48 (14) 2919–2924, 1992; Rapoport et. al, *JOC*, 51, 5106–5110, 1986).

In method A (Scheme I), the bromo-indoles (II) were reacted with alkyl halides or aryl-alkyl halides using a base such as sodium hydride in DMF or THF to give the N-substituted bromo-indoles (III). The N-substituted bromo-indoles (III) were converted to the corresponding boronic acids (IV) by treating III in THF with nBuLi, followed by triisopropyl-borate and subsequent quenching with aqueous acid. Boronic acids (IV) were then subjected to palladium catalyzed cross-coupling with various substituted aryl-halides affording the aryl-indoles (VI). Alternatively, N-substituted bromo-indoles (III) were subjected to the palladium catalyzed cross-coupling with various substituted aryl-boronic acids to afford the aryl-indoles (VI). Furthermore, reaction of bromo-indoles (II) with various substituted aryl-boronic acids under the palladium catalyzed cross-coupling conditions afforded the aryl-indoles (V). Alkylation of (V) with alkyl-halides or aryl-alkyl-halides under basic conditions as described above afforded the N-substituted aryl-indoles (VI). Reaction of VI with n-butyllithium and carbon dioxide afforded the desired acids (I). Reaction of VI with oxalyl chloride in methylene chloride followed by quenching with water afforded the desired ketoacids (I, Y=O), which were purified by crystallization. Alternatively reaction of VI with oxalyl chloride in methylene chloride followed by quenching with alcohol afforded the keto-esters (VII). The ketoesters (VII) can be purified by either crystallization or chromatography. Conversion of the ketoesters (VII) to the corresponding ketoacids (I, Y=O) was accomplished by saponification of the ester followed by neutralization with an acid such as hydrochloric acid. Reaction of (I, Y=O) with hydrazine followed by treatment with a base such as sodium methoxide while heating in a solvent such as 2-methoxyethanol yielded The corresponding acetic acid (I, Y=H,H). Alternatively, Bromoindoles (II) were reacted with dimethyl amine and formaldehyde and the product was then treated with potassium cyanide to furnish the indole acetonitrile derivatives (IIa). Conversion of IIa to the IIb was carried out as described above. Base hydrolysis of the nitrile of IIb to the corresponding acid furnished the desired compounds (I, Y=H,H).

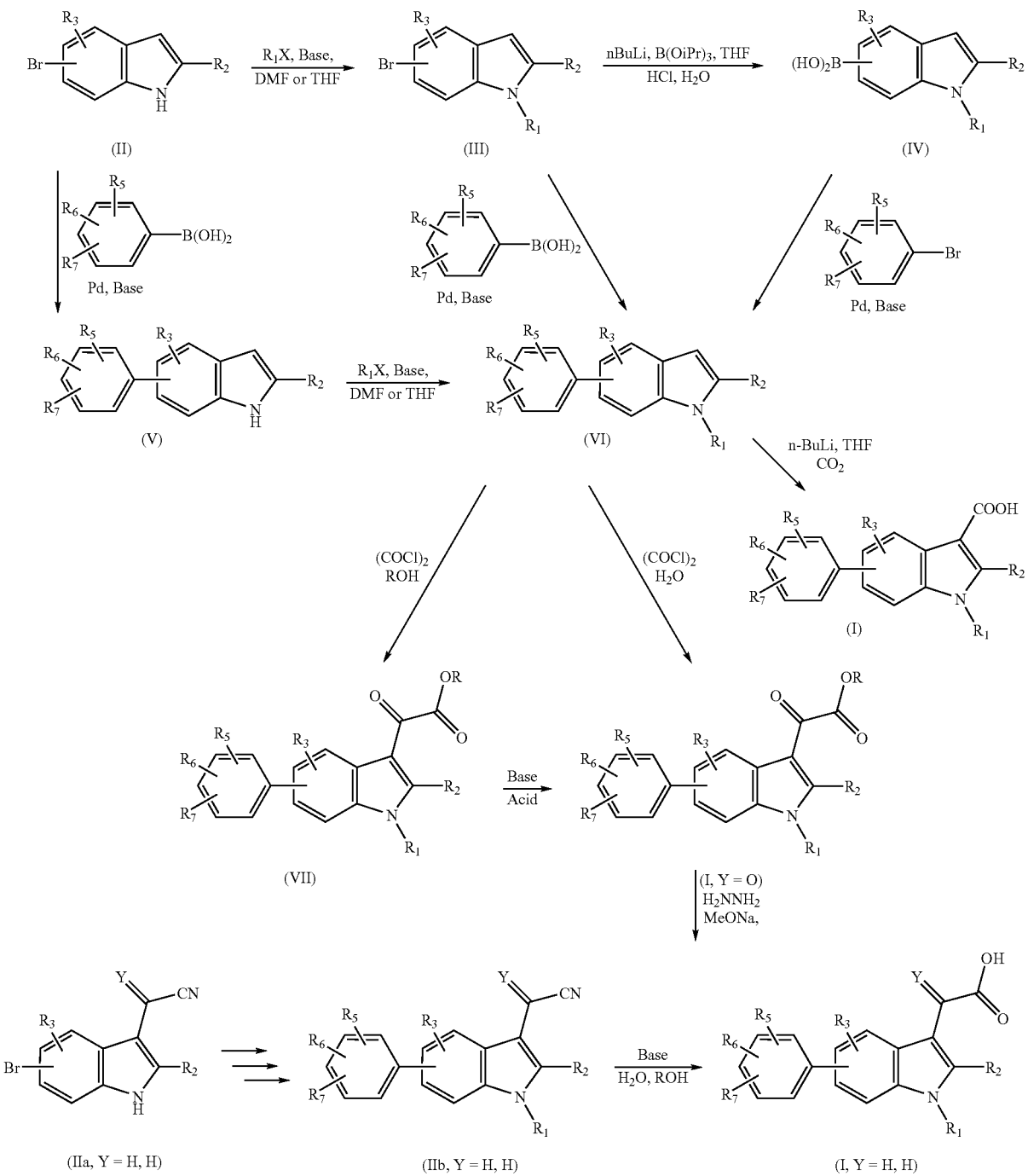

Scheme I

In method B (Scheme II), an indole (II), substituted on the benzene ring with bromide, iodine, or triflate, is coupled with an aryl boronic acid in the presence of a palladium catalyst, such as Pd(PPh$_3$)$_4$, a base, such as Na$_2$CO$_3$ or NaHCO$_3$, in a solvent, such as water, methanol or ethanol, or in a mixed co-solvent system comprising two or more of the aforesaid solvents, at 50–110° C. Boronic acid derivatives of benzene, furan, thiophene, benz[b]thiophene and naphthalene are described in the literature and many are presently commercially available. The resulting aryl indole (V) can be sulfonylated on nitrogen using phenylsulfonyl chloride or toluenesulfonyl chloride in the presence of a base, such as NaH or KOt-Bu, in an inert solvent, such as THF or DMF. The resulting 5-aryl-1H-arylsulfonyl indole (VIII) is reacted with alcohols in the presence of base, such as NaH or KOt-Bu, in an inert solvent, preferably toluene or DMF, at 80–200° C., to give 5-aryl-1H-alkyl indoles (VI). Reaction with oxalyl chloride, neat or in an inert solvent, affords the indol-3-yl glyoxylic chloride. Quenching the reaction with water affords the desired 5-aryl-1H-alkyl indol-3-yl glyoxylic acids (I).

Scheme II

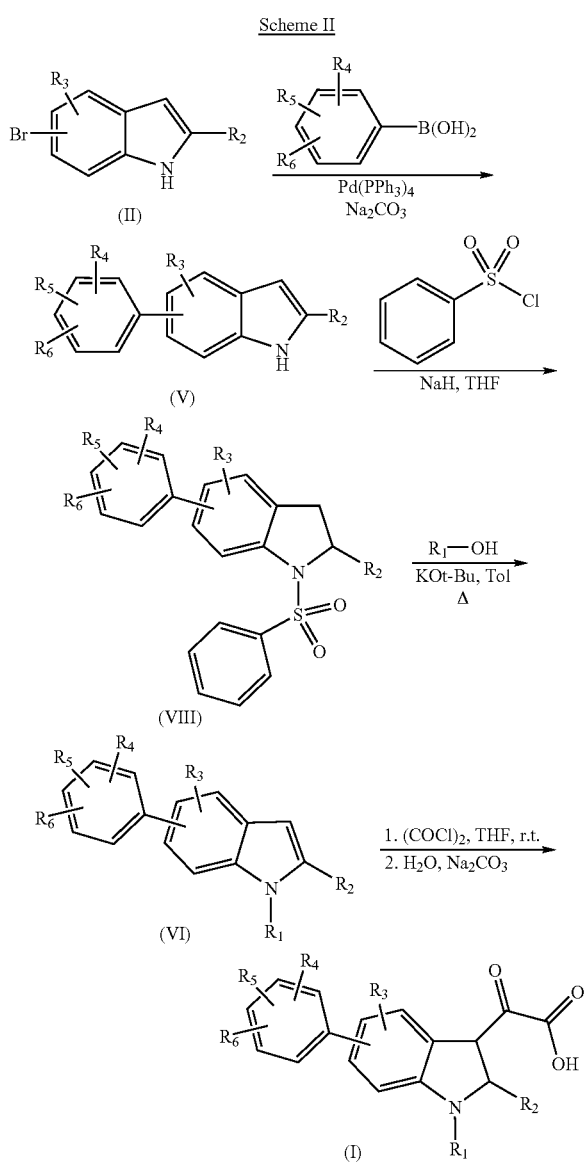

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit plasminogen activator inhibitor-1 was established by the following experimental procedures:

Primary Screen for the PAI-1 Inhibition

Test compounds are dissolved in DMSO at a final concentration of 10 mM, then diluted 100× in physiologic buffer. The inhibitory assay is initiated by the addition of the test compound (1–100 μM final concentration, maximum DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (American Diagnostica, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the test compound on tPA alone.

Assay for Determining $IC_{50}$ of Inhibition of PAI-1

This assay is based upon the non-SDS dissociable interaction between tPA and active PAI-1. Assay plates are initially coated with human tPA (10 μg/ml). Test compounds are dissolved in DMSO at 10 mM, then diluted with physiologic buffer (pH 7.5) to a final concentration of 1–50 μM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table I.

TABLE I

| Example | $IC_{50}$ (μM) | % Inhibition @ 25 μM |
|---|---|---|
| 1 | — | 15 |
| 2 | 32[b] | |
| 3 | — | 24 |
| 4 | — | 16 |

TABLE I-continued

| Example | $IC_{50}$ (μM) | % Inhibition @ 25 μM |
|---|---|---|
| 5 | 17.3[a] | |
| 6 | — | 27 |
| 7 | — | 26 |
| 8 | 11.2[b] | |
| 9 | — | 40 |
| 10 | — | 33 |
| 11 | — | 19 |
| 12 | 2.7[a] | |
| 13 | — | 27 |
| 14 | — | 55 |
| 15 | 6.5[b] | |
| 16 | 11.5[a] | |
| 17 | 10[a] | |
| 18 | 19.4[b] | |
| 19 | 15.8[b] | |
| 20 | — | 14 |
| 21 | 19.9[a] | |
| 22 | 9.7[a] | |
| 23 | — | 40 |
| 24 | — | 47 |
| 25 | 14[b] | |
| 26 | 6.8[b] | |
| 27 | 5.3[b] | |
| 28 | 35[a] | |
| 29 | 12.5[a] | |
| 30 | 16[b] | |
| 31 | — | 32 |
| 32 | — | 28 |
| 33 | 10.5[a] | |
| 34 | 6.2[b] | |
| 35 | 14.6[b] | |
| 36 | 10[a] | |
| 37 | 16.4[a] | |
| 38 | — | 14 |
| 39 | 21.6[a] | |
| 40 | 8.5[b] | |
| 41 | — | 13 |
| 42 | 45.7[a] | |
| 43 | 17.2[a] | |
| 44 | 26.3[a] | |
| 45 | — | 45 |
| 46 | — | 45 |
| 47 | — | 51 |
| 48 | 13.3[a] | — |
| 49 | — | 54 |
| 50 | — | 59 |
| 51 | — | 58 |
| 52 | — | 59 |
| 53 | — | 67 |
| 54 | — | 46 |
| 55 | — | 51 |
| 56 | — | 54 |
| 57 | — | 57 |
| 58 | — | 61 |
| 59 | — | 58 |
| 60 | — | 39 |
| 61 | — | 28 |
| 62 | 11.16[a] | 53 |
| 63 | — | — |
| 64 | — | — |

[a]The $IC_{50}$ was determined by the Antibody Assay described above.
[b]The $IC_{50}$ was determined by a modification of the Primary Screen for the PAI-1 Inhibition.

EXAMPLE 1

{1-Methyl-6-[4-(trifluoromethoxy)phenyl]-1H-indol-3-yl}(oxo)acetic acid

Step 1

6-(4-Trifluoromethoxyphenyl)-1H-indole

The mixture of 6-bromo-1H-indole (1.22 g, 6.22 mmol), 4-trifluoromethoxyphenyl boronic acid (1.41 g, 6.84 mmol), tetrakis(triphenylphosphine)palladium (0.213 g, 0.184 mmol) and sodium carbonate (2.64 g, 24.9 mmoles) in water (12.5 mL), ethanol (4 mL), and toluene (25 mL) was heated at reflux for 1.5 hours then cooled to room temperature. The mixture was then evaporated to dryness and the residue was partitioned in methylene chloride and water. The organic phase was washed with water, brine, dried over anhydrous magnesium sulfate and evaporated to dryness. The residue was purified by flash chromatography using 10–30% chloroform in hexane as an eluant. The title compound was obtained as a white solid (0.874 g, 51%), mp: 165–166° C. $^1$HNMR (300 MHz, DMSO-$d_6$): δ 11.25 (s, 1H), 7.8 (d, 2H, J=7.0 Hz), 7.65 (d, 2H, J=7.0 Hz), 7.4–7.5 (m, 3H), 7.3 (d, 1H, J=8.8 Hz), and 6.45 ppm (s, 1H).

Step 2

6-(4-Trifluoromethoxyphenyl)-1-methyl-1H-indole

To a solution of 6-(4-trifluoromethoxyphenyl)-1H-indole (0.853, 3.08 mmoles) in dry THF (10 mL) was added sodium hydride (60% dispersion on mineral oil, 0.47 g, 12.3 mmol), portionwise. The reaction mixture was stirred under nitrogen for 30 minutes and, then cooled in ice bath. A solution of iodomethane (0.38 mL, 6.1 mmole) in dry THF (10 mL) was added and the reaction mixture was stirred for 1 hour at room temperature. The mixture was then poured into excess water, acidified with 2N hydrochloric acid and extracted with ethyl acetate. The organic phase was washed with brine, dried over anhydrous magnesium sulfate and evaporated to dryness. The residue was purified by flash chromatography (Biotage apparatus) using 0.5% t-butyl methyl ether in hexane as an eluant. The title compound was obtained as a cream-colored solid that was vacuum dried at 66° C. (0.623 g, 70%). $^1$HNMR (300 MHz, DMSO-$d_6$): δ 7.85 (d, 2H, J=8.3 Hz), 7.75 (s, 1H), 7.65 (d, 1H, J=8.3 Hz), 7.45 (d, 2H, J=8.3 Hz), 7.3–7.4 (m, 2H), 6.45 (s, 1H), and 3.85 ppm (s, 3H).

Step 3

Methyl 2-[6-(4-trifluoromethoxyphenyl)-1-methyl-1H-indol-3-yl]-2-oxoacetate

To a solution of 6-(4-trifluoromethoxyphenyl)-1-methyl-1H-indole (0.304 g, 1.04 mmol) in dry THF (5 mL) under nitrogen at 0° C. was added oxalyl chloride (0.11 ml, 1.2 mmol). The reaction mixture was stirred at room temperature for 2 hour. The mixture was cooled in an ice bath. Methanol (1 mL) was added. The reaction mixture was stirred at room temperature for 1 hour then poured into excess sodium bicarbonate solution and extracted with ethyl acetate. The organic phase was washed with water and brine, dried over anhydrous magnesium sulfate, and evaporated to dryness. The residue was purified by flash chromatography (Biotage apparatus) using 20–50% ethyl acetate in hexane as an eluant. The title compound was obtained as a cream-colored solid (0.196 g, 50%), mp: 152–153° C. Mass spectrum (+APCI, [M+H]$^+$) m/z 378; $^1$HNMR (400 MHz, DMSO-$d_6$): δ 8.55 (s, 1H), 8.2 (d, 1H, J=8.3 Hz), 7.95 (t, 1H, J=0.77 Hz), 7.90–7.95 (m, 2H,), 7.65 (dd, 1H, J=8.3 Hz and 1.5 Hz), 7.45 (d, 2H, J=8.6 Hz), 4.0 (s, 3H), and 3.9 ppm (m, 3H).

Elemental Analysis for $C_{19}H_{14}F_3NO_4$: Calculated: C, 60.48; H, 3.74; N, 3.71. Found: C, 60.60; H, 3.86; N, 3.60.

Step 4

{1-Methyl-6-[4-(trifluoromethoxy)phenyl]-1H-indol-3-yl}(oxo)acetic acid

The mixture of methyl 2-[6-(4-trifluoromethoxyphenyl)-1-methyl-1H-indol-3-yl]-2-oxoacetate (0.120 g, 0.318 mmol), and sodium hydroxide (1N, 1 mL, 1.0 mmol) in methanol (10 mL), was stirred at room temperature for 2.5 hours. The mixture was poured into excess water and acidified with 1N hydrochloric acid. The mixture was extracted with ethyl acetate. The organic phase was washed with water, brine and dried over anhydrous magnesium sulfate. The organic phase was evaporated to dryness and dried under vacuum at 55° C. for 12 hours to yield the title compound as a yellow solid (0.0686 g, 59.1%), mp: 233–235° C. (dec). Mass spectrum (+APCI, [M+H]$^+$) m/z 364; $^1$HNMR (400 MHz, DMSO-$d_6$): δ 13.8–14.0 (br s, 1H), 8.55 (s, 1H), 8.25 (d, 1H, J=8.3 Hz), 7.95 (d, 1H, J=1.1 Hz), 7.85–7.95 (m, 2H), 7.65 (dd, 1H, J=8.2 and 1.6 Hz), 7.45 (dd, 2H, J=8.8 Hz and 0.88 Hz), and 4.0 ppm (s, 3H).

Elemental Analysis for $C_{19}H_{14}F_3NO_4$: Calculated: C, 59.51; H, 3.33; N, 3.86. Found: C, 59.39; H, 3.38; N, 3.71.

EXAMPLE 2

{1-Methyl-6-[4-(trifluoromethyl)phenyl]-1H-indol-3-yl}(oxo)acetic acid

Step 1

6-Bromo-1-methyl-1H-indole

A solution of 6-bromo-1H-indole (2.34 g, 11.9 mmol) in dry THF (25 mL) was cooled in an ice bath. Sodium hydride (1.12 g of 60% dispersion in oil, 28.0 mmol) was added. The mixture was stirred for 30 minutes under nitrogen at room temperature, then cooled in an ice bath. Iodomethane (1.6 mL, 26 mmol) was added. The reaction mixture was stirred for 2 hours at room temperature, poured into excess water, acidified with 2N hydrochloric acid and extracted with ethyl acetate. The organic phase was washed with water and brine, dried over anhydrous magnesium sulfate and evaporated to dryness. The residue was purified by flash chromatography using hexane as an eluant to yield 6-bromo-1-methyl-1H-indole 2.04 g (81.6%, 9.71 mmol) as a yellow oil. $^1$HNMR (200 MHz, DMSO-$d_6$): δ 7.7 (s, 1H), 7.5 (d, 1H, J=8.6 Hz), 7.35 (d, 1H, J=2.1 Hz), 7.15 (d, 1H, 7.3 Hz), 6.4 (d, 1H, J=1.3 Hz), and 3.75 ppm (s, 3H).

Step 2

6-(4-Trifluoromethylphenyl)-1-methyl-1H-indole

The mixture of 6-bromo-1-methyl-1H-indole (0.216 g, 1.03 mmol), 4-trifluoromethylbenzeneboronic acid (0.216 g, 1.14 mmol), tetrakis(triphenylphosphine)palladium (0.0541 g, 0.0468 mmol) and sodium carbonate (0.438 g, 4.13 mmol) in water (2.5 mL), ethanol (1 mL) and toluene (5 mL) was refluxed for 1.6 hours. The mixture was cooled to room temperature then evaporated to dryness. The residue was partitioned in methylene chloride and water. The organic phase was washed with water, brine, dried over anhydrous magnesium sulfate and evaporated to dryness. The residue was purified by flash chromatography using 0–0.2% ethyl acetate in hexane as an eluant to give the title compound (0.144 g, 51%) as a white solid, mp: ~100° C.; $^1$HNMR (200 MHz, DMSO-$d_6$): δ 8.0 (d, 2H, J=6.6 Hz), 7.8 (d, 3H, J=8.7 Hz), 7.65 (d, 1H, J=8.7 Hz), 7.35–7.5 (m, 2H), 6.45 (d, 1H, J=2.6 Hz), and 3.8–3.95 ppm (m, 3H).

Step 3

Methyl 2-[6-(4-trifluoromethylphenyl)-1-methyl-1H-indol-3-yl]-2-oxoacetate

Following the procedure described in Step 3 of Example 1, 6-(4-trifluoromethylphenyl)-1-methyl-1H-indole (0.135 g, 0.490 mmol) was converted to methyl 2-[6-(4-trifluoromethylphenyl)-1-methyl-1H-indol-3-yl]-2-oxoacetate. Purification by flash chromatography using 20–50% ethyl acetate in hexane as an eluant yielded a pale yellow solid (0.103 g, 58%), mp: 199–200° C. $^1$HNMR (300 MHz, DMSO-$d_6$): δ 8.6 (s, 1H), 8.25 (d, 1H, J=7.5 Hz), 8.0 (d, 3H, J=7.5 Hz), 7.85 (d, 2H, J=7.5 Hz), 7.7 (s, 1H, J=7.5 Hz), 4.0 (s, 3H), and 3.9 ppm (s, 3H).

Step 4

{1-Methyl-6-[4-(trifluoromethyl)phenyl]-1H-indol-3-yl}(oxo)acetic acid

Following the procedure described in Step 4 of Example 1, methyl 2-[6-(4-trifluoromethylphenyl)-1-methyl-1H- indol-3-yl]-2-oxoacetate (0.0988 g, 0.273 mmol) was converted to {1-methyl-6-[4-(trifluoromethyl)phenyl]-1H-indol-3-yl}(oxo)acetic acid as a yellow solid (0.0557 g, 59%), mp: 256–257° C. (dec.). Mass spectrum (–ESI, [M–H]⁻) m/z 346. ¹HNMR (400 MHz, DMSO-$d_6$): δ 13.8–14.0 (br s, 1H), 8.55 (s, 1H), 8.3 (d, 1H, J=8.3 Hz), 8.0–8.05 (m, 3H), 7.85 (d, 2H, J=8.3 Hz), 7.70 (dd, 1H, J=8.3 Hz and 1.5 Hz), and 4.0 ppm (s, 3H).

Elemental Analysis for $C_{18}H_{12}F_3NO_3$: Calculated: C, 62.25; H, 3.48; N, 4.03. Found: C, 62.02; H, 3.36; N, 3.98.

EXAMPLE 3

{1-Ethyl-6-[4-(trifluoromethoxy)phenyl]-1H-indol-3-yl}(oxo)acetic acid

Step 1

6-Bromo-1-ethyl-1H-indole

A solution of 6-bromoindole (1.01 g, 5.15 mmol) in THF (10 mL) was cooled in an ice bath. Sodium hydride (0.459 g of 60% dispersion in oil, 11.5 mmol) was added. After stirring for 35 minutes at room temperature under nitrogen, the reaction mixture was again cooled in an ice bath, and iodoethane (0.90 mL, 11 mmol) was added. The mixture was stirred for 2 hours at room temperature, poured into excess water, acidified with 2N hydrochloric acid and extracted with ethyl acetate. The organic phase was washed with water and brine, dried over anhydrous magnesium sulfate and evaporated to dryness. The residue was purified by flash chromatography using hexane as an eluant to yield 6-bromo-1-ethyl-1H-indole (0.812 g, 71%) as a yellow oil. ¹HNMR (300 MHz, DMSO-$d_6$): δ 7.75 (s, 1H), 7.5 (d, 1H, J=7.8 Hz), 7.45 (d, 1H, J=3.9 Hz), 7.15 (dd, 1H, J=7.8 Hz and 1.6 Hz), 6.45 (s, 1H), 4.2 (q, 2H, J=7.1 Hz), and 1.35 ppm (t, 3H, J=7.0 Hz).

Step 2

6-(4-Trifluoromethoxyphenyl)-1-ethyl-1H-indole

Following the procedure described in Step 2 of Example 2, 6-bromo-1-ethyl-1H-indole (0.410 g, 1.83 mmol) was reacted with 4-trifluoromethoxybenzene boronic acid (0.422 g, 2.05 mmol), using tetrakis(triphenylphosphine)palladium (0.0651 g, 0.0563 mmol), and sodium carbonate (0.792 g, 7.47 mmol) in water (3.7 mL), ethanol (1.4 mL), and toluene (8 mL). Purification by flash chromatography using hexane as an eluant yielded the title compound as a yellow oil (0.312 g, 56%). ¹HNMR (300 MHz, DMSO-$d_6$): δ 7.85 (d, 2H, J=6.3 Hz), 7.8 (s, 1H), 7.65 (d, 1H, J=7.8 Hz), 7.4–7.5 (m, 3H), 7.35 (d, 1H, J=6.2 Hz), 6.45 (d, 1H, J=2.3 Hz), 4.3 (q, 2H, J=7.0 Hz), and 1.4 ppm (t, 3H, J=7.0 Hz).

Step 3

Ethyl 2-[6-(4-trifluoromethoxyphenyl)-1-ethyl-1H-indol-3-yl]-2-oxoacetate

Following the procedure described in Step 3 of Example 1, ethyl 2-[6-(4-trifluoromethoxyphenyl)-1-ethyl-1H-indol-3-yl]-2-oxoacetate was prepared from 6-(4-trifluoromethoxyphenyl)-1-ethyl-1H-indole (0.284 g, 0.930 mmol), oxalyl chloride (0.10 mL, 1.1 mmol), and ethanol (2 mL). Purification by flash chromatography using 3–10% ethyl acetate in hexane as an eluant yielded (0.247 g, 66%) of the title compound as a yellow solid, mp: 114–116° C. Mass spectrum (EI, M⁺) m/z 405; ¹HNMR (400 MHz, DMSO-$d_6$): δ 8.55 (s, 1H), 8.25 (d, 1H, J=8.3 Hz), 8.0 (d, 1H, J=0.98 Hz), 7.85–7.9 (m, 2H), 7.65 (dd, 1H, J=8.3 Hz and 1.4 Hz), 7.45 (dd, 2H, J=8.8 Hz and 0.98 Hz), 4.35–4.45 (m, 4H), 1.45 (t, 3H, J=7.2 Hz), and 1.35 ppm (t, 3H, J=7.1 Hz).

Elemental Analysis for $C_{21}H_{18}F_3NO_4$: Calculated: C, 62.22; H, 4.48; N, 3.46. Found: C, 62.27; H, 4.39; N, 3.41.

Step 4

{1-Ethyl-6-[4-(trifluoromethoxy)phenyl]-1H-indol-3-yl}(oxo)acetic acid

Following the procedure described in Step 4 of Example 2, ethyl 2-[6-(4-trifluoromethoxyphenyl)-1-ethyl-1H-indol-3-yl]-2-oxoacetate (0.156 g, 0.385 mmol) was converted to the title compound as a yellow solid (0.121 g, 83%), mp: 204–205° C. Mass spectrum (+APCI, [M+H]⁺) m/z 378; ¹HNMR (400 MHz, DMSO-$d_6$): δ 13.8–14.0 (br s, 1H), 8.55 (s, 1H), 8.25 (dd, 1H, J=8.3 Hz and 0.49 Hz), 8.0 (t, 1H, J=0.73 Hz), 7.85–7.90 (m, 2H), 7.65 (dd, 1H, J=8.3 Hz and 1.5 Hz), 7.45 (dd, 2H, J=8.8 Hz and 0.98 Hz), 4.45 (q, 2H, J=7.2 Hz), and 1.45 ppm (t, 3H, J=7.2 Hz).

Elemental Analysis for $C_{19}H_{14}F_3NO_4$: Calculated: C, 60.48; H, 3.74; N, 3.71. Found: C, 60.39; H, 3.52; N, 3.61.

EXAMPLE 4

{1-Ethyl-6-[4-(trifluoromethyl)phenyl]-1H-indol-3-yl}(oxo)acetic acid

Step 1

6-(4-Trifluoromethylphenyl)-1-ethyl-1H-indole

Following the procedure described in Step 2 of Example 2, 6-bromo-1-ethyl-1H-indole (0.400 g, 1.78 mmol), was coupled to 4-trifluoromethylbenzene boronic acid (0.348 g, 1.83 mmol), using tetrakis(triphenylphosphine)palladium (0.0668 g, 0.0578 mmol), and sodium carbonate (0.769 g, 7.26 mmol) in water (3.6 mL), ethanol (1.5 mL), and toluene (8 mL). Purification by flash chromatography using hexane as an eluant yielded the title compound as a yellow oil (0.289 g, 56%). ¹HNMR (300 MHz, DMSO-$d_6$): δ 7.95 (d, 2H, J=7.7 Hz), 7.9 (s, 1H), 7.8 (d, 2H, J=7.7 Hz), 7.65 (d, 1H, J=7.7 Hz), 7.5 (d, 1H, J=1.5 Hz), 7.45 (d, 1H, J=7.7 Hz), 6.45 (d, 1H, J=2.3 Hz), 4.3 (q, 2H, J=6.9 Hz) and 1.4 ppm (t, 3H, J=6.9 Hz).

Step 2

Ethyl 2-[6-(4-trifluoromethylphenyl)-1-ethyl-1H-indol-3-yl]-2-oxoacetate

Following the procedure described in Step 3 of Example 1, ethyl 2-[6-(4-trifluoromethylphenyl)-1-ethyl-1H-indol-3-yl]-2-oxoacetate was prepared from 6-(4-trifluoromethylphenyl)-1-ethyl-1H-indole (0.289 g, 0.999 mmol), oxalyl chloride (0.10 mL, 1.1 mmol), and ethanol (2 mL). Purification by flash chromatography using 3–10% ethyl acetate in hexane as an eluant yielded the title compound as a yellow solid (0.145 g, 37%), mp: 139–141° C. Mass spectrum (+APCI, [M+H]⁺) m/z 390; ¹HNMR (400 MHz, DMSO-$d_6$): δ 8.55 (s, 1H), 8.25 (d, 1H, J=8.3 Hz), 8.05 (d, 1H, J=0.98 Hz), 8.0 (d, 2H, J=8.3 Hz), 7.85 (d, 2H, J=8.3 Hz), 7.7 (dd, 1H, J=8.3 Hz and 1.5 Hz), 4.45 (q, 2H, J=7.2 Hz), 4.4 (q, 2H, J=7.1 Hz), 1.45 (t, 3H, J=7.2 Hz), and 1.35 ppm (t, 3H, J=7.1 Hz).

Elemental Analysis for $C_{21}H_{18}F_3NO_3$: Calculated: C, 64.78; H, 4.66; N, 3.60. Found: C, 64.67; H, 4.56; N, 3.54.

Step 3

{1-Ethyl-6-[4-(trifluoromethyl)phenyl]-1H-indol-3-yl}(oxo)acetic acid

Following the procedure described in Step 4 of Example 2, using ethyl 2-[6-(4-trifluoromethylphenyl)-1-ethyl-1H-indol-3-yl]-2-oxoacetate (0.0987 g, 0.253 mmol), and 1N sodium hydroxide (0.76 mL, 0.76 mmol) in methanol (5 mL), 2-[6-(4-trifluoromethylphenyl)-1-ethyl-1H-indol-3-yl]-2-oxoacetate acid (0.0714 g, 78%) was prepared as a yellow solid, mp 247–248° C. Mass spectrum (+APCI, [M+H]⁺) m/z 362; ¹HNMR (400 MHz, DMSO-$d_6$): δ 13.7–14.1 (br s, 1H), 8.55 (s, 1H), 8.3 (d, 1H, J=8.3 Hz), 8.05 (d, 1H, J=0.98 Hz), 8.0 (d, 2H, J=8.1 Hz), 7.8 (d, 2H, J=8.5 Hz), 7.7 (dd, 1H, J=8.5 Hz and 1.6 Hz), 4.45 (q, 2H, J=7.2 Hz), and 1.45 ppm (t, 3H, J=7.2 Hz).

Elemental Analysis for $C_{19}H_{14}F_3NO_3$: Calculated: C, 63.16; H, 3.91; N, 3.88. Found: C, 62.91; H, 3.67; N, 3.73.

EXAMPLE 5

{1-Benzyl-6-[4-(trifluoromethoxy)phenyl]-1H-indol-3-yl}(oxo)acetic acid

Step 1

1-Benzyl-6-bromo-1H-indole

A solution of 6-bromoindole (5.0 g, 26 mmol) in dry DMF (45 mL) was cooled in an ice bath. Sodium hydride (2.2 g of 60% dispersion in oil, 55 mmol) was added. After stirring for 30 minutes under nitrogen at room temperature, the reaction mixture was cooled in an ice bath, and benzyl bromide (6.1 mL, 51 mmol) was added. After stirring for one hour at room temperature, the reaction mixture was poured into excess water, acidified with 2N hydrochloric acid and extracted with ethyl acetate. The organic phase was then washed with water and brine, then dried over anhydrous magnesium sulfate and evaporated to dryness. Purification of the residue by flash chromatography using hexane as an eluant and drying for 30 minutes at 60° C. yielded 1-benzyl-6-bromo-1H-indole (5.83 g, 80%) as a waxy solid, mp: 85–88° C. Mass spectrum (+ESI, [M+H]$^+$) m/z 286; $^1$HNMR (500 MHz, DMSO-d$_6$): δ 7.7 (d, 1H, J=0.61 Hz), 7.50–7.55 (m, 2H), 7.30 (t, 2H, J=7.3 Hz), 7.2–7.25 (m, 1H), 7.2 (d, 2H, J=8.4 Hz), 7.15 (dd, 1H, J=8.4 Hz and 1.7 Hz), 6.5 (dd, 1H, J=3.1 Hz and 0.77 Hz), and 5.45 ppm (s, 2H).

Step 2

1-Benzyl-6-(4-trifluoromethoxylphenyl)-1H-indole

The mixture of 1-benzyl-6-bromo-1H-indole (0.272 g, 0.950 mmol), 4-trifuoromethoxybenzeneboronic acid (0.217 g, 1.05 mmol), tetrakis(triphenylphosphine)palladium (0.0340 g, 0.0294 mmol) and sodium carbonate (0.405 g, 3.82 mmol) in water (1.9 mL), ethanol (1 mL) and toluene (5 mL) was heated at reflux for 5 hours. The mixture was cooled to room temperature and evaporated to dryness. The residue was partitioned in methylene chloride and water. The organic phase was washed with brine, dried over anhydrous magnesium sulfate and evaporated to dryness. The residue was purified by flash chromatography using hexane as an eluant affording the title compound as thick yellow oil. $^1$HNMR (200 MHz, DMSO-d$_6$): δ 7.8 (d, 3H, J=7.7 Hz), 7.65 (d, 2H, J=7.7 Hz), 7.55 (d, 2H, J=2.0 Hz), 7.2–7.5 (m, 5H), 6.55 (d, 1H, J=1.5 Hz), and 5.5 ppm (s, 2H).

Step 3

Ethyl 2-[1-benzyl-6-(4-trifluoromethoxylphenyl)-1H-indol-3-yl]-2-oxoacetate

Following the procedure described in Step 3 of Example 1, ethyl 2-[1-benzyl-6-(4-trifluoromethoxyphenyl)-1H-indol-3-yl]-2-oxoacetate was prepared from 1-benzyl-6-(4-trifluoromethoxyphenyl)-1H-indole (1.20 g, 3.27 mmol), oxalyl chloride (0.85 mL, 10 mmol) in THF (20 mL), and ethanol (5 mL). Purification by flash chromatography (Biotage apparatus) using 5–10% ethyl acetate in hexane as an eluant yielded the title compound as a yellow gum (0.128 g, 84%). $^1$HNMR (300 MHz, DMSO-d$_6$): δ 8.7 (s, 1H), 8.25 (d, 1H, J=7.7 Hz), 8.0 (s, 1H), 7.8 (d, 2H, J=7.7 Hz), 7.65 (dd, 1H, J=7.7 Hz and 0.77 Hz), 7.45 (d, 2H, J=7.7 Hz), 7.25–7.4 (m, 5H), 5.65 (s, 2H), 4.35 (q, 2H, J=7.2 Hz), and 1.35 ppm (t, 3H, J=7.2 Hz).

Step 4

{1-Benzyl-6-[4-(trifluoromethoxy)phenyl]-1H-indol-3-yl}(oxo)acetic acid

A mixture of ethyl 2-[1-benzyl-6-(4-trifluoromethoxyphenyl)-1H-indol-3-yl]-2-oxoacetate (1.27 g, 2.72 mmol), potassium hydroxide (0.539 g, 9.61 mmol) in THF (12 mL) and water (12 mL) was stirred at room temperature for 3.5 hours. The mixture was poured into excess water, acidified with 2N hydrochloric acid, and extracted with ethyl acetate. The organic phase was washed with water and brine, dried over anhydrous magnesium sulfate, and evaporated to dryness. The residue was dried under vacuum at 92° C. for 15 hours to yield the title compound (0.985 g, 82%) as a yellow solid. A sample crystallized from isopropanol gave a solid, mp: 202–204° C. (dec.). Mass spectrum (+APCI, [M+H]$^+$) m/z 440; $^1$HNMR (400 MHz, DMSO-d$_6$): δ 13.8–14.2 (br s, 1H), 8.7 (s, 1H), 8.25 (d, 1H, J=8.3 Hz), 7.95 (t, 1H, J=0.73 Hz), 7.8–7.85 (m, 2H), 7.65 (dd, 1H, J=8.3 Hz and 1.5 Hz), 7.45 (d, 2H, J=8.8 Hz), 7.25–7.4 (m, 5H), and 5.65 ppm (s, 2H).

Elemental Analysis for $C_{24}H_{16}F_3NO_4$: Calculated: C, 65.61; H, 3.67; N, 3.19. Found: C, 65.59; H, 3.54; N, 3.18.

EXAMPLE 6

{1-Benzyl-6-[4-(trifluoromethyl)phenyl]-1H-indol-3-yl}(oxo)acetic acid

Step 1

1-Benzyl-6-[4-(trifluoromethyl)phenyl]-1H-indole

Following the procedure described in Step 2 of Example 5, 1-benzyl-6-bromo-1H-indole (0.490 g, 1.71 mmol), was coupled to 4-trifluoromethylbenzeneboronic acid (0.376 g, 1.98 mmol), using tetrakis(triphenylphosphine)palladium (0.0663 g, 0.057 mmol) and sodium carbonate (0.733 g, 6.92 mmol) in water (3.5 mL), ethanol (2 mL) and toluene (10 mL). Purification by flash chromatography using 0–1% ethyl acetate in hexane as an eluant yielded the title compound as a yellow solid (0.426 g, 71%), mp: 83–85° C. $^1$HNMR (300 MHz, DMSO-d$_6$): δ 7.9 (d, 3H, J=7.7 Hz), 7.8 (d, 2H, J=7.7 Hz), 7.7 (d, 1H, J=7.7 Hz), 7.6 (d, 1H, J=3.9 Hz), 7.4 (d, 1H, J=7.7 Hz), 7.2–7.4 (m, 5H), 6.55 (d, 1H, J=2.3 Hz), and 5.55 ppm (s, 2H).

Step 2

Ethyl 2-{1-benzyl-6-[4-(trifluoromethyl)phenyl]-1H-indol-3-yl}-2-oxoacetate

Following the procedure described in Step 3 of Example 1, ethyl 2-[1-benzyl-6-(4-trifluoromethyl)-1H-indol-3-yl]-2-oxoacetate was prepared from 1-benzyl-6-[4-(trifluoromethyl)phenyl]-1H-indole (0.392 g, 1.12 mmol), oxalyl chloride (0.11 mL, 1.2 mmol), and ethanol (1.4 mL). Purification by flash chromatography using 5–10% ethyl acetate in hexane as an eluant followed by trituration with hexane yielded the title compound as a light yellow solid (0.314 g, 62%), mp: 109–110° C. Mass spectrum (+APCI, [M+H]$^+$) m/z 452; $^1$HNMR (400 MHz, DMSO-d$_6$): δ 8.75 (s, 1H), 8.25 (d, 1H, J=8.3 Hz), 8.05 (d, 1H, J=0.98 Hz), 7.95 (d, 2H, J=8.1 Hz), 7.8 (d, 2H, J=8.3 Hz), 7.7 (dd, 1H, J=8.3 Hz and 1.5 Hz), 7.25–7.35 (m, 5H), 5.7 (s, 2H), 4.35 (q, 2H, J=7.2 Hz), and 1.35 ppm (t, 3H, J=7.1 Hz).

Elemental Analysis for $C_{26}H_{20}F_3NO_3 \cdot 0.25\ H_2O$: Calculated: C, 68.49; H, 4.53; N, 3.07. Found: C, 68.24; H, 4.46; N, 3.10.

Step 3

{1-Benzyl-6-[4-(trifluoromethyl)phenyl]-1H-indol-3-yl}(oxo)acetic acid

Following the procedure described in Step 4 of Example 5, {1-benzyl-6-[4-(trifluoromethyl)phenyl]-1H-indol-3-yl}(oxo)acetic acid was prepared from ethyl 2-[1-benzyl-6-(4-trifluoromethyl)-1H-indol-3-yl]-2-oxoacetate (0.208 g, 0.461 mmol) using 1N sodium hydroxide (1.4 mL, 1.4 mmol) in ethanol (12 mL). The title compound was obtained as a light yellow solid (0.155 g, 80%), mp: 223–224° C. (dec.). Mass spectrum (+APCI, [M+H]$^+$) m/z 424; $^1$HNMR (400 MHz, DMSO-d$_6$): δ 13.95–14.05 (br s, 1H), 8.75 (s, 1H), 8.3 (dd, 1H, J=8.3 Hz and 0.49 Hz), 8.05 (d, 1H, J=0.98

Hz), 7.9 (d, 2H, J=8.3 Hz), 7.8 (d, 2H, J=8.3 Hz), 7.7 (dd, 1H, J=8.3 Hz and 1.7 Hz), 7.25–7.35 (m, 5H), and 5.7 ppm (s, 2H).

Elemental Analysis for $C_{24}H_{16}F_3NO_3 \cdot 0.10\ H_2O$: Calculated: C, 67.80; H, 3.84; N, 3.29. Found: C, 67.58; H, 3.63; N, 3.29.

EXAMPLE 7

{1-[4-(tert-Butyl)benzyl]-6-[4-(trifluoromethyl)phenyl]-1H-indol-3-yl}(oxo)acetic acid Step 1

6-Bromo-1-[4-(tert-butyl)benzyl]-1H-indole

Following the procedure described in Step 1 of Example 5, 6-Bromo-1-[4-(tert-butyl)benzyl]-1H-indole was prepared from 6-bromoindole (6.00 g, 30.6 mmol), and 1-(bromomethyl)-4-(tert-butyl)benzene (11.2 mL, 60 mmol), using sodium hydride (2.42 g of 60% dispersion in oil, 60.5 mmol) in dry DMF (60 mL). Flash chromatography on a Biotage apparatus using hexane as an eluant yielded the title compound as green syrup (8.23 g, 79%). $^1$HNMR (200 MHz, DMSO-$d_6$): δ 7.75 (s, 1H), 7.5 (t, 2H, J=6.1 Hz), 7.35 (d, 2H, J=6.1 Hz), 7.0–7.2 (m, 3H), 6.5 (d, 1H, J=2.6 Hz), 5.2 (s, 2H), and 1.3 ppm (s, 9H).

Step 2

1-[4-(tert-Butyl)benzyl]-6-[4-(trifluoromethyl)phenyl]-1H-indole

Following the procedure described in Step 2 of Example 5, 6-bromo-1-[4-(tert-butyl)benzyl]-1H-indole (0.490 g, 1.43 mmol) was coupled to 4-trifluoromethylbenzeneboronic acid (0.300 g, 1.58 mmol), using tetrakis(triphenylphosphine)palladium (0.0560 g, 0.0484 mmol) and sodium carbonate (0.615 g, 5.80 mmol) in water (2.8 mL), ethanol (1.4 mL) and toluene (10 mL). Purification by flash chromatography using hexane as an eluant afforded 1-[4-(tert-butyl)benzyl]-6-[4-(trifluoromethyl)phenyl]-1-H-indole as a white solid (0.392 g, 67%), mp 134–135° C. $^1$HNMR (200 MHz, DMSO-$d_6$): δ 7.85 (d, 3H, J=7.7 Hz), 7.75 (d, 2H, J=7.7 Hz), 7.65 (d, 1H, J=7.7 Hz), 7.55 (d, 1H, J=4.1 Hz), 7.25–7.4 (m, 3H), 7.15 (d, 2H, J=7.7 Hz), 6.5 (d, 1H, J=2.6 Hz), 5.45 (s, 2H), and 1.2 ppm (s, 9H).

Step 3

Ethyl 2-{1-[4-(tert-butyl)benzyl]-6-[4-(trifluoromethyl)phenyl]-1H-indol-3-yl}-2-oxoacetate Following the procedure described in Step 3 of Example 1, ethyl 2-{1-[4-(tert-butyl)benzyl]-6-[4-(trifluoromethyl)phenyl]-1H-indol-3-yl}-2-oxoacetate was prepared from 1-[4-(tert-butyl)benzyl]-6-[4-(trifluoromethyl)phenyl]-1H-indole (0.382 g, 0.932 mmol), oxalyl chloride (0.09 mL, 1 mmol), and ethanol (2 mL). Purification by flash chromatography using 2.5–10% ethyl acetate in hexane as an eluant followed by drying at 65° C. for 50 minutes yielded the title compound as a light yellow solid (0.267 g, 56%), mp: 164–165° C. Mass spectrum (+APCI, [M+H]$^+$) m/z 508; $^1$HNMR (400 MHz, DMSO-$d_6$): δ 8.7 (s, 1H), 8.25 (d, 1H, J=8.3 Hz), 8.1 (d, 1H, J=0.98 Hz), 7.95 (d, 2H, J=8.1 Hz), 7.8 (d, 2H, J=8.3 Hz), 7.7 (dd, 1H, J=8.3 Hz and 1.5 Hz), 7.35 (d, 2H, J=8.3 Hz), 7.30 (d, 2H, J=8.3 Hz), 5.65 (s, 2H), 4.35 (q, 2H, J=7.2 Hz), 1.35 (t, 3H, J=7.1 Hz), and 1.2 ppm (s, 9H).

Elemental Analysis for $C_{30}H_{28}F_3NO_3$: Calculated: C, 70.99; H, 5.56; N, 2.76. Found: C, 70.71; H, 5.50; N, 2.67.

Step 4

{1-[4-(tert-Butyl)benzyl]-6-[4-(trifluoromethyl)phenyl]-1H-indol-3-yl}(oxo)acetic acid Following the procedure described in Step 4 of Example 5, {1-[4-(tert-butyl)benzyl]-6-[4-(trifluoromethyl)phenyl]-1H-indol-3-yl}(oxo)acetic acid was prepared from ethyl 2-{1-[4-(tert-butyl)benzyl]-6-[4-(trifluoromethyl)phenyl]-1H-indol-3-yl}-2-oxoacetate (0.185 g, 0.365 mmol), using 1N sodium hydroxide (1.1 mL, 1.1 mmol) and ethanol (10 mL). The title compound was obtained as a yellow solid (0.137 g, 78%), mp 205–206° C. (dec.). Mass spectrum (−ESI, M$^−$) m/z 479; $^1$HNMR (400 MHz, DMSO-$d_6$): δ 13.8–14.1 (br s, 1H), 8.75 (s, 1H), 8.3 (dd, 1H, J=8.3 Hz and 0.49 Hz), 8.05 (d, 1H, J=0.98 Hz), 7.95 (d, 2H, J=8.3 Hz), 7.8 (d, 2H, J=8.3 Hz), 7.7 (dd, 1H, J=8.3 Hz and 1.5 Hz), 7.35–7.4 (m, 2H), 7.25–7.3 (m, 2H), 5.65 (s, 2H), and 1.2 ppm (s, 9H).

Elemental Analysis for $C_{28}H_{24}F_3NO_3$: Calculated: C, 70.14; H, 5.04; N, 2.92. Found: C, 69.79; H, 5.04; N, 2.92.

EXAMPLE 8

{1-[4-(tert-Butyl)benzyl]-6-[4-(trifluoromethoxy)phenyl]-1H-indol-3-yl}(oxo)acetic acid Step 1

1-[4-(tert-Butyl)benzyl]-6-[4-(trifluoromethoxy)phenyl]-1H-indole

Following the procedure described in Step 2 of Example 5, 6-bromo-1-[4-(tert-butyl)benzyl]-1H-indole (0.488 g, 1.43 mmol) was coupled to 4-trifluoromethoxybenzene boronic acid (0.329 g, 1.60 mmol), using tetrakis(triphenylphosphine)palladium (0.0574 g, 0.0496 mmol) and sodium carbonate (0.617 g, 5.82 mmol) in water (2.8 mL), ethanol (1.4 mL) and toluene (10 mL). Purification by flash chromatography using hexane as an eluant yielded 1-[4-(tert-butyl)benzyl]-6-[4-(trifluoromethoxy)phenyl]-1H-indole as a white solid (0.372 g, 61%), mp 100–102° C. $^1$HNMR (200 MHz, DMSO-$d_6$): δ 7.8 (d, 3H, J=8.5 Hz), 7.65 (d, 1H, J=8.5 Hz), 7.55 (d, 1H, J=3.5 Hz), 7.3–7.5 (m, 5H), 7.15 (d, 2H, J=7.5 Hz), 6.5 (d, 1H, J=3.5 Hz), 5.45 (s, 2H), and 1.2 ppm (s, 9H).

Step 2

Ethyl{1-[4-(tert-butyl)benzyl]-6-[4-(trifluoromethoxy)phenyl]-1H-indol-3-yl}(oxo)acetate Following the procedure described in Step 3 of Example 1, ethyl {1-[4-(tert-butyl)benzyl]-6-[4-(trifluoromethoxy)phenyl]-1H-indol-3-yl}(oxo)acetate was prepared from 1-[4-(tert-butyl)benzyl]-6-[4-(trifluoromethoxy)phenyl]-1H-indole (3.52 g, 8.31 mmol), oxalyl chloride (2.9 mL, 33 mmol) and ethanol (10 mL). Purification by flash chromatography using 10% tert-butyl methyl ether in hexane as an eluant and crystallization from acetonitrile yielded the title compound as a light yellow solid (2.69 g, 62%), mp: 146–147° C. Mass spectrum (+ESI, [M+H]$^+$) m/z 524; $^1$HNMR (500 MHz, DMSO-$d_6$): δ 8.7 (s, 1H), 8.25 (d, 1H, J=8.4 Hz), 8.0 (d, 1H, J=0.61 Hz), 7.85 (d, 2H, J=8.9 Hz), 7.65 (dd, 1H, J=8.3 Hz and 1.5 Hz), 7.45 (d, 2H, J=8.2 Hz), 7.35 (d, 2H, J=8.4 Hz), 7.30 (d, 2H, J=8.4 Hz), 5.65 (s, 2H), 4.35 (q, 2H, J=7.1 Hz), 1.35 (t, 3H, J=7.1 Hz), and 1.2 ppm (s, 9H).

Elemental Analysis for $C_{30}H_{28}F_3NO_4$: Calculated: C, 68.82; H, 5.39; N, 2.68. Found: C, 68.56; H, 5.19; N, 2.88.

Step 3

{1-[4-(tert-Butyl)benzyl]-6-[4-(trifluoromethoxy)phenyl]-1H-indol-3-yl}(oxo)acetic acid Following the procedure described in Step 4 of Example 5, {1-[4-(tert-butyl)benzyl]-6-[4-(trifluoromethoxy)phenyl]-1H-indol-3-yl}(oxo)acetic acid was prepared from ethyl 2-{1-[4-(tert-butyl)benzyl]-6-[4-(trifluoromethoxy)phenyl]-1H-indol-3-yl}-2-oxoacetate (2.53 g, 4.83 mmol) using potassium hydroxide (0.897 g, 16.0 mmol) in THF (25 mL) and water (25 mL). Crystallization from acetonitrile and drying for 24 hours at 92° C. yielded the title compound as a yellow solid (1.51 g, 63%), mp: 183–186° C. Mass spectrum (–ESI, [M–H]$^-$) m/z 494; $^1$HNMR (500 MHz, DMSO-d$_6$): δ 13.8–14.1 (br s, 1H), 8.7 (s, 1H), 8.25 (d, 1H, J=8.4 Hz), 8.0 (s, 1H), 7.85 (d, 2H, J=8.7 Hz), 7.60 (d, 1H, J=9.0 Hz), 7.45 (d, 2H, J=8.3 Hz), 7.35 (d, 2H, J=8.4 Hz), 7.30 (d, 2H, J=8.4 Hz), 5.65 (s, 2H), and 1.2 ppm (m, 9H).

Elemental Analysis for C$_{28}$H$_{24}$F$_3$NO$_4$: Calculated: C, 67.87; H, 4.88; N, 2.83. Found: C, 67.92; H, 4.72; N, 2.72.

EXAMPLE 9

{1-Benzyl-5-[4-(trifluoromethyl)phenyl]-1H-indol-3-yl}(oxo)acetic acid

Step 1

1-Benzyl-5-bromo-1H-indole

The title compound was prepared from 5-bromoindole (5.02 g, 25.6 mmol) and benzyl bromide (6.7 mL, 56 mmol), following the procedure described in Step 1 of Example 5. Purification by flash chromatography on Biotage apparatus using hexane as an eluant yielded 1-benzyl-5-bromo-1H-indole as a white solid (5.69 g, 78%), mp 93–95° C. Mass spectrum (+ESI, [M+H]$^+$) m/z 286; $^1$HNMR (500 MHz, DMSO-d$_6$): δ 7.7 (d, 1H, J=1.8 Hz), 7.55 (d, 1H, J=3.1 Hz), 7.4 (d, 1H, J=8.7 Hz), 7.15–7.30 (m, 6H), 6.45 (dd, 1H, J=3.2 Hz and 0.6 Hz), and 5.45 ppm (s, 2H).

Elemental Analysis for C$_{15}$H$_{12}$BrN: Calculated: C, 62.96; H, 4.23; N, 4.89. Found: C, 63.36; H, 4.31; N, 4.73.

Step 2

1-Benzyl-5-[4-(trifluoromethyl)phenyl]-1H-indole

Following the procedure described in Step 2 of Example 5 1-benzyl-5-bromo-1H-indole (2.22 g, 7.76 mmol) was coupled to 4-trifluoromethylphenyl boronic acid (1.62 g, 8.54 mmol), using tetrakis(triphenylphosphine)palladium (0.892 g, 0.772 mmol), and potassium carbonate (4.29 g, 31.1 mmol) in water (17 mL), ethanol (4 mL), and toluene (37 mL). Purification by flash chromatography using 0.5–1.0% ethyl acetate in hexane as eluant afforded the title compound as a light yellow solid (0.317 g, 12%). $^1$HNMR (200 MHz, DMSO-d$_6$): δ 7.7–8.0 (m, 5H), 7.4–7.6 (m, 3H), 7.15–7.4 (m, 5H), 6.6 (d, 1H, J=3.6 Hz), and 5.45 ppm (s, 2H).

Step 3

Ethyl 2-{1-benzyl-5-[4-(trifluoromethyl)phenyl]-1H-indol-3-yl}-2-oxoacetate

Ethyl 2-{1-benzyl-5-[4-(trifluoromethyl)phenyl]-1H-indol-3-yl}-2-oxoacetate was prepared from 1-Benzyl-5-[4-(trifluoromethyl)phenyl]-1H-indole (0.307 g, 0.874 mmol), oxalyl chloride (0.29 mL, 3.3 mmol), and ethanol (3 mL) following the procedure described in Step 3 of Example 1. The compound was purified by flash chromatography using 10–20% ethyl acetate in hexane as an eluant and dried for 20 minutes at 60° C. to give a light yellow solid (0.249 g, 63%), mp: 99–100° C. $^1$ HNMR (200 MHz, DMSO-d$_6$): δ 8.8 (s, 1H), 8.5 (s, 1H), 7.6–7.95 (m, 6H), 7.25–7.4 (m, 5H), 5.65 (s, 2H), 4.35 (q, 2H, J=7.7 Hz), and 1.35 ppm (t, 3H, J=7.7 Hz).

Step 4

{1-Benzyl-5-[4-(trifluoromethyl)phenyl]-1H-indol-3-yl}(oxo)acetic acid

Following the procedure described in Step 4 of Example 5 {1-benzyl-5-[4-(trifluoromethyl)phenyl]-1H-indol-3-yl}(oxo)acetic acid was prepared from ethyl 2-{1-benzyl-5-[4-(trifluoromethyl)phenyl]-1H-indol-3-yl}-2-oxoacetate (0.232 g, 0.515 mmol), potassium hydroxide (0.113 g, 2.37 mmol) in THF (3 mL) and water (3 mL). The compound was dried for 2.5 hours at 60° C. to yield a light yellow solid (0.181 g, 83%), mp: 201–202° C. (dec.). Mass spectrum (–APCI, [M–H]$^-$) m/z 422; $^1$HNMR (400 MHz, DMSO-d$_6$): δ 13.8–14.2 (br s, 1H), 8.75 (s, 1H), 8.5 (d, 1H, J=1.7 Hz), 7.9 (d, 2H, J=8.3 Hz), 7.8 (d, 2H, J=8.5 Hz), 7.7 (d, 1H, J=8.5 Hz), 7.65 (dd, 1H, J=8.6 Hz and 1.8 Hz), 7.25–7.35 (m, 5H), and 5.65 ppm (s, 2H).

Elemental Analysis for C$_{24}$H$_{16}$F$_3$NO$_4$: Calculated: C, 68.08; H, 3.81; N, 3.31. Found: C, 67.99; H, 3.63; N, 3.29.

EXAMPLE 10

{6-[4-(tert-Butyl)phenyl]-1-methyl-1H-indol-3-yl}(oxo)acetic acid

Step 1

6-[4-(tert-Butyl)phenyl]-1-methyl-1H-indole

Following the procedure described in Step 2 of Example 5, 6-bromo-1-methyl-1H-indole (1.12 g, 5.33 mmol) was coupled to 4-(tert-butyl)phenylboronic acid (1.07 g, 6.00 mmol), using tetrakis(triphenylphosphine)palladium (0.655 g, 0.567 mmol), and potassium carbonate (2.94 g, 21.3 mmol) in water (10.6 mL), ethanol (2.2 mL), and toluene (23 mL). Purification by flash chromatography (Biotage apparatus) using 0–1% ethyl acetate in hexane as an eluant then drying at 60° C. yielded 6-[4-(tert-butyl)phenyl]-1-methyl-1H-indole as a yellow solid (0.790 g, 56%), mp: 92–94° C. $^1$HNMR (200 MHz, DMSO-d$_6$): δ 7.55–7.7 (m, 5H), 7.45 (d, 2H, J=7.5 Hz), 7.3 (d, 2H, J=8.5 Hz), 6.6 (d, 1H, J=3.5 Hz), 3.9 (s, 3H), and 1.3 ppm (s, 9H).

Step 2

Ethyl 2-{6-[4-(tert-butyl)phenyl]-1-methyl-1H-indol-3-yl}-2-oxoacetate

Ethyl 2-{6-[4-(tert-butyl)phenyl]-1-methyl-1H-indol-3-yl}-2-oxoacetate was prepared from 6-[4-(tert-butyl)phenyl]-1-methyl-1H-indole (0.230 g, 0.874 mmol), oxalyl chloride (0.16 mL, 1.8 mmol), and ethanol (2 mL) following the procedure described in Step 3 of Example 1. The compound was purified by HPLC using 30% ethyl acetate in hexane as the mobile phase and dried for 20 minutes at 60° C. to yield a light yellow solid (0.141 g, 44%). $^1$HNMR (300 MHz, DMSO-d$_6$): δ 8.5 (s, 1H), 8.2 (d, 1H, J=8.3 Hz), 7.9 (s, 1H), 7.7 (d, 2H, J=7.5 Hz), 7.65 (d, 1H, J=9.0 Hz), 7.5 (d, 2H, J=7.5 Hz), 4.35 (q, 2H, J=7.5 Jz), 3.95 (s, 3H), and 1.3–1.4 ppm (m, 12H).

Step 3

{6-[4-(tert-Butyl)phenyl]-1-methyl-1H-indol-3-yl}(oxo)acetic acid

Following the procedure described in Step 4 of Example 5, {6-[4-(tert-butyl)phenyl]-1-methyl-1H-indol-3-yl}(oxo)acetic acid was prepared from ethyl 2-{6-[4-(tert-butyl)phenyl]-1-methyl-1H-indol-3-yl}-2-oxoacetate (0.136 g, 0.374 mmol), and potassium hydroxide (0.096 g, 1.71 mmol) in THF (10 mL) and water (10 mL). The compound was dried for 3 hours at 70° C. to yield a yellow solid (0.0943 g, 75%), mp: 201–202° C. (dec.). Mass spectrum (–APCI, [M–H]$^-$) m/z 334; $^1$HNMR (400 MHz, DMSO-d$_6$): δ 13.8–14.1 (br s, 1H), 8.5 (s, 1H), 8.2 (d, 1H, J=8.3 Hz), 7.85 (d, 1H, J=0.98 Hz), 7.7 (dd, 2H, J=6.6 Hz and 2.0 Hz), 7.6 (dd, 1H, J=8.3 Hz and 1.5 Hz), 7.5 (d, 1H, J=8.5 Hz), 4.0 (s, 3H), and 1.3 ppm (s, 9H).

Elemental Analysis for C$_{21}$H$_{21}$NO$_3$.0.20 H$_2$O: Calculated: C, 74.40; H, 6.36; N, 4.13. Found: C, 74.58; H, 6.13; N, 4.04.

EXAMPLE 11

[5-(4-Acetylphenyl)-1-benzyl-1H-indol-3-yl](oxo)acetic acid

Step 1

1-[4-(1-Benzyl-1H-indol-5-yl)phenyl]-1-ethanone

A mixture of 1-benzyl-5-bromo-1H-indole (1.00 g, 3.49 mmol), 4-acetylphenylboronic acid (0.692 g, 4.22 mmol),

[1,1'-bis(diphenylphosphino)ferrocene]dichloropalladium (II) complex with dichloromethane (1:1) (0.0581 g, 0.0711 mmol), potassium carbonate (0.725 g, 5.25 mmol) in dioxane (35 mL) and water (3.5 mL) was heated at 65–70° C. for 3 hours. The reaction mixture was evaporated to dryness and partitioned in ethyl acetate and 2N hydrochloric acid. The organic phase was washed with water and brine, dried over anhydrous magnesium sulfate and evaporated to dryness. The residue was purified by flash chromatography using (1–10% ethyl acetate in hexane and 10–15% chloroform in hexane) to yield 1-[4-(1-benzyl-1H-indol-5-yl)phenyl]-1-ethanone as a buff-colored solid (0.262 g, 23%), mp: 134–135° C. $^1$HNMR (300 MHz, DMSO-d$_6$): δ 7.95–8.1 (m, 3H), 7.85 (d, 2H, J=7.7 Hz), 7.5–7.65 (m, 3H), 7.2–7.4 (m, 5H), 6.6 (d, 1H, J=2.5 Hz), 5.5 (s, 2H), and 2.6 ppm (s, 3H).

Step 2

Ethyl 2-[5-(4-acetylphenyl)-1-benzyl-1H-indol-3-yl]-2-oxoacetate

Ethyl 2-[5-(4-acetylphenyl)-1-benzyl-1H-indol-3-yl]-2-oxoacetate was prepared from 1-[4-(1-benzyl-1H-indol-5-yl)phenyl]-1-ethanone (0.255 g, 0.784 mmol), oxalyl chloride (0.14 mL, 1.6 mmol), and ethanol (2 mL), following the procedure described in Step 3 of Example 1. Purification by flash chromatography using 30–50% chloroform in hexane as an eluant and drying at 55° C. yielded a brownish solid (0.243 g, 73%). $^1$HNMR (300 MHz, DMSO-d$_6$): δ 8.75 (s, 1H), 8.5 (s, 1H), 8.05 (d, 2H, J=9.2 Hz), 7.8 (d, 2H, J=7.7 Hz), 7.7 (q, 2H, J=8.5 Hz), 7.25–7.4 (m, 5H), 5.65 (s, 2H), 4.35 (q, 2H, J=7.2 Hz), 2.6 (s, 3H), and 1.35 ppm (t, 3H, J=7.3 Hz).

Step 3

[5-(4-Acetylphenyl)-1-benzyl-1H-indol-3-yl](oxo)acetic acid

[5-(4-Acetylphenyl)-1-benzyl-1H-indol-3-yl](oxo)acetic acid was prepared from ethyl [5-(4-acetylphenyl)-1-benzyl-1H-indol-3-yl](oxo)acetate (0.225 g, 0.529 mmol), and potassium hydroxide (0.104 g, 1.85 mmol) in THF (7 mL) and water (7 mL) according to the procedure described in Step 4 of Example 5. After drying for 15 hours at 96° C., the title compound was obtained as a tan solid (0.166 g, 79%), mp: 213–214° C. (dec.). Mass spectrum (−APCI, [M−H]$^−$) m/z 396; $^1$HNMR (400 MHz, DMSO-d$_6$): δ 8.75 (s, 1H), 8.5 (d, 1H, J=1.7 Hz), 8.05 (d, 2H, J=8.3 Hz), 7.8 (d, 2H, J=8.3 Hz), 7.7 (d, 1H, J=8.8 Hz), 7.65 (dd, 1H, J=8.7 Hz and 1.6 Hz), 7.25–7.4 (m, 5H), 5.65 (s, 2H), and 2.6 ppm (s, 3H).

Elemental Analysis for $C_{25}H_{19}NO_4 \cdot 0.50\ H_2O$: Calculated: C, 73.87; H, 4.96; N, 3.45. Found: C, 73.54; H, 4.64; N, 3.32.

EXAMPLE 12

{1-Benzyl-5-[4-(trifluoromethoxy)phenyl]-1H-indol-3-yl}(oxo)acetic acid

Step 1

1-Benzyl-5-[4-(trifluoromethoxy)phenyl]-1H-indole

1-Benzyl-5-[4-(trifluoromethoxy)phenyl]-1H-indole was prepared by coupling of 1-benzyl-5-bromo-1H-indole (5.2 g, 18 mmol) and 4-trifluoromethoxyphenylboronic acid (4.7 g, 23 mmol), using [1,1'-bis(diphenylphosphino)ferrocene]dichloropalladium(II) complex with dichloromethane (1:1) (0.88 g, 1.1 mmol), and potassium carbonate (3.8 g, 27 mmol) in dioxane (135 mL) and water (13.5 mL) according to the procedure described in Step 1 of Example 11. Purification by flash chromatography (Biotage apparatus) using hexane as an eluant yielded the title compound as a light yellow solid (2.8 g, 42%), mp: 62–63° C. $^1$HNMR (300 MHz, DMSO-d$_6$): δ 7.85 (s, 1H), 7.75 (d, 2H, J=7.7 Hz), 7.5–7.6 (m, 2H), 7.4 (d, 3H, J=7.7 Hz), 7.2–7.35 (m, 5H), 6.6 (d, 1H, J=3.9 Hz), and 5.45 ppm (s, 2H).

Step 2

Ethyl 2-{1-benzyl-5-[4-(trifluoromethoxy)phenyl]-1H-indol-3-yl}-2-oxoacetate

Ethyl {1-benzyl-5-[4-(trifluoromethoxy)phenyl]-1H-indol-3-yl}(oxo)acetate was prepared from 1-benzyl-5-[4-(trifluoromethoxy)phenyl]-1H-indole (2.80 g, 7.62 mmol), oxalyl chloride (2.0 mL, 23 mmol), and ethanol (4.5 mL) according to the procedure described in Step 3 of Example 1. Purification by flash chromatography using 5–10% ethyl acetate in hexane as an eluant then drying at 60° C. furnished the title compound as a yellow gum (3.05 g, 86%). $^1$HNMR (300 MHz, DMSO-d$_6$): δ 8.75 (s, 1H), 8.45 (s, 1H), 7.8 (d, 2H, J=9.2 Hz), 7.75 (d, 1H, J=9.2 Hz), 7.6 (d, 1H, J=9.2 Hz), 7.45 (d, 2H, J=9.2 Hz), 7.3–7.4 (m, 5H), 5.85 (s, 2H), 4.35 (q, 2H, J=7.5 Hz), and 1.35 ppm (t, 3H, J=7.5 Hz).

Step 3

{1-Benzyl-5-[4-(trifluoromethoxy)phenyl]-1H-indol-3-yl}(oxo)acetic acid

{1-Benzyl-5-[4-(trifluoromethoxy)phenyl]-1H-indol-3-yl}(oxo)acetic acid was prepared from ethyl 2-{1-benzyl-5-[4-(trifluoromethoxy)phenyl]-1H-indol-3-yl}-2-oxoacetate (0.463 g, 0.991 mmol), potassium hydroxide (0.224 g, 3.99 mmol) in THF (5 mL) and water (5 mL) according to the procedure described in Step 4 of Example 5. The title compound was obtained as a light yellow solid (0.314 g, 78%), mp 169–171° C. Mass spectrum (+APCI, [M+H]$^+$) m/z 440; $^1$HNMR (400 MHz, DMSO-d$_6$): δ 13.8–14.2 (br s, 1H), 8.75 (s, 1H), 8.45 (d, 1H, J=1.5 Hz), 7.75–7.8 (m, 2H), 7.7 (d, 1H, J=8.5 Hz), 7.6 (dd, 1H, J=8.7 Hz), 7.45 (d, 2H, J=8.8 Hz), 7.25–7.35 (m, 5H), and 5.65 ppm (s, 2H).

Elemental Analysis for $C_{24}H_{16}F_3NO_4$: Calculated: C, 65.61; H, 3.67; N, 3.19. Found: C, 65.59; H, 3.54; N, 3.17.

EXAMPLE 13

{1-Benzyl-4-[4-(trifluoromethyl)phenyl]-1H-indol-3-yl}(oxo)acetic acid

Step 1

1-Benzyl-4-bromo-1H-indole

1-Benzyl-4-bromo-1H-indole was prepared from 4-bromo-1H-indole (1.58 g, 8.06 mmol), sodium hydride (0.680 g of 60% dispersion in oil, 17.0 mmol), and benzyl bromide (2.0 mL, 17 mmol) in DMF (15 mL) according to the procedure described in Step 1 of Example 5. Purification by flash chromatography (Biotage apparatus) using hexane as an eluant yielded a light yellow oil (1.61 g, 70%). $^1$HNMR (300 MHz, DMSO-d$_6$): δ 7.65 (d, 1H, J=3.8 Hz), 7.5 (d, 1H, J=7.7 Hz), 7.15–7.35 (m, 6H), 7.05 (t, 1H, J=7.7 Hz), 6.45 (d, 1H, J=3.1 Hz), and 5.6 ppm (s, 2H).

Step 2

1-Benzyl-4-[4-(trifluoromethyl)phenyl]-1H-indole

1-Benzyl-4-[4-(trifluoromethyl)phenyl]-1H-indole was prepared by coupling of 1-benzyl-4-bromo-1H-indole (0.428 g, 1.50 mmol), and 4-trifluoromethylphenylboronic acid (0.374 g, 1.97 mmol), using [1,1'-bis(diphenylphosphino)ferrocene]dichloropalladium (II) complex with dichloromethane (1:1) (0.0638 g, 0.0781 mmol), and potassium carbonate (0.416 g, 3.01 mmol) in dioxane (15 mL) and water (1.5 mL) following the procedure described in Step 1 of Example 11. Purification by flash chromatography (Biotage apparatus) using hexane as an eluant yielded the title compound as a yellow gum (0.259 g, 49%). $^1$HNMR (300 MHz, DMSO-d$_6$): δ 7.8–7.95 (m, 4H), 7.65 (d, 1H, J=3 Hz), 7.55 (d, 1H, J=7.5 Hz), 7.15–7.35 (m, 7H), 6.65 (d, 1H, J=3 Hz), and 5.5 ppm (s, 2H).

Step 3

Ethyl {1-benzyl-4-[4-(trifluoromethyl)phenyl]-1H-indol-3-yl}(oxo)acetate

Ethyl {1-benzyl-4-[4-(trifluoromethyl)phenyl]-1H-indol-3-yl}(oxo)acetate was prepared from 1-benzyl-4-[4-(trifluoromethyl)phenyl]-1H-indole (0.257 g, 0.731 mmol), oxalyl chloride (2.2 mL, 26 mmol), and ethanol (6 mL) according to the procedure described in Step 3 of Example 1. Purification by HPLC using 3% ethanol in hexane as the mobile phase afforded the title compound as a hard yellow gum (0.064 g, 19%). $^1$HNMR (200 MHz, DMSO-$d_6$): δ 8.7 (s, 1H), 7.7 (d, 3H, J=7.7 Hz), 7.15–7.5 (m, 9H), 5.65 (s, 2H), 4.25 (q, 2H, J=7.0 Hz), and 1.35 ppm (t, 3H, J=7.1 Hz).

Step 4

{1-Benzyl-4-[4-(trifluoromethyl)phenyl]-1H-indol-3-yl}(oxo)acetic acid

2-{1-Benzyl-4-[4-(trifluoromethyl)phenyl]-1H-indol-3-yl}-2-oxoacetic acid was prepared from ethyl {1-benzyl-4-[4-(trifluoromethyl)phenyl]-1H-indol-3-yl}(oxo)acetate (0.064 g, 0.142 mmol), and potassium hydroxide (0.0471 g, 0.839 mmol) in THF (2.5 mL) and water (2.5 mL) according to the procedure described in Step 4 of Example 5. The title compound was obtained as a light yellow solid (0.0497 g, 89%), mp: 183–184° C. Mass spectrum (+APCI, [M+H]$^+$) m/z 424; $^1$HNMR (400 MHz, DMSO-$d_6$): δ 13.5–14.0 (br s, 1H), 8.65 (s, 1H), 7.65–7.7 (m, 3H), 7.25–7.45 (m, 8H), 7.2 (dd, 1H, J=7.3 Hz and 0.73 Hz), and 5.65 ppm (s, 2H).

Elemental Analysis for $C_{24}H_{16}F_3NO_3 \cdot 0.20\ H_2O$: Calculated: C, 67.51; H, 3.87; N, 3.28. Found: C, 67.54; H, 3.56; N, 3.17.

EXAMPLE 14

{1-Benzyl-5-[4-(tert-butyl)phenyl]-1H-indol-3-yl}(oxo)acetic acid

Step 1

1-Benzyl-5-[4-(tert-butyl)phenyl]-1H-indole

-Benzyl-5-[4-(tert-butyl)phenyl]-1H-indole was prepared by coupling 1-benzyl-5-bromo-1H-indole (1.44 g, 5.03 mmol), and 4-(tert-butyl)phenylboronic acid (1.08 g, 6.07 mmol), using [1,1'-bis(diphenylphosphino)ferrocene] dichloropalladium(II) complex with dichloromethane (1:1) (0.204 g, 0.250 mmol), and potassium carbonate (1.39 g, 10.1 mmol) in dioxane (50 mL) and water (5 mL) following the procedure described in Step 1 of Example 11. Purification by flash chromatography (Biotage apparatus) using 0–5% chloroform in hexane as an eluant yielded the title compound as an aqua solid (0.741 g, 43%), mp: 136–137° C. $^1$HNMR (200 MHz, DMSO-$d_6$): δ 7.8 (s, 1H), 7.2–7.6 (m, 12H), 6.55 (d, 1H, J=2.6 Hz), 5.45 (s, 2H), and 1.3 ppm (s, 9H).

Step 2

Ethyl {1-benzyl-5-[4-(tert-butyl)phenyl]-1H-indol-3-yl}(oxo)acetate

Ethyl {1-benzyl-5-[4-(tert-butyl)phenyl]-1H-indol-3-yl}(oxo)acetate was prepared from 1-benzyl-5-[4-(tert-butyl)phenyl]-1H-indole (0.732 g, 2.16 mmol), oxalyl chloride (0.75 mL, 8.6 mmol), and ethanol (6 mL) according to the procedure described in Step 3 of Example 1. Purification by flash chromatography (Biotage apparatus) using 5–10% ethyl acetate in hexane as an eluant afforded the title compound as a light yellow solid (0.671 g, 71%). $^1$HNMR (200 MHz, DMSO-$d_6$): δ 8.7 (s, 1H), 8.4 (s, 1H), 7.45–7.7 (m, 6H), 7.35 (s, 5H), 5.65 (s, 2H), 4.35 (q, 2H, J=6.7 Hz), and 1.3–1.45 ppm (m, 12H).

Step 3

{1-Benzyl-5-[4-(tert-butyl)phenyl]-1H-indol-3-yl}(oxo)acetic acid

{1-Benzyl-5-[4-(tert-butyl)phenyl]-1H-indol-3-yl}(oxo)acetic acid was prepared from ethyl {1-benzyl-5-[4-(tert-butyl)phenyl]-1H-indol-3-yl}(oxo)acetate (0.669 g, 1.52 mmol), potassium hydroxide (0.30 g, 5.3 mmol) in THF (15 mL) and water (15 mL) according to the procedure described in Step 4 of Example 5. Purification by crystallization from acetonitrile and drying at 90° C. furnished the title compound as a light yellow solid (0.391 g, 63%), mp: 210–211° C. (dec.). Mass spectrum (+APCI, [M+H]$^+$) m/z 412; $^1$ HNMR (400 MHz, DMSO-$d_6$): δ 13.8–14.2 (br s, 1H), 8.7 (s, 1H), 8.4 (d, 1H, J=1.7 Hz), 7.65 (d, 1H, J=8.5 Hz), 7.55–7.6 (m, 3H), 7.5 (dd, 2H, J=6.5 Hz and 1.8 Hz), 7.3–7.35 (m, 5H), 5.6 (s, 2H), and 1.3 ppm (s, 9H).

Elemental Analysis for $C_{27}H_{25}NO_3 \cdot 0.1\ H_2O$: Calculated: C, 78.46; H, 6.15; N, 3.39. Found: C, 78.34; H, 5.94; N, 3.35.

EXAMPLE 15

[1-Benzyl-5-(3-chloro-4-fluorophenyl)-1H-indol-3-yl](oxo)acetic acid

Step 1

1-Benzyl-5-(3-chloro-4-fluorophenyl)-1H-indole

1-Benzyl-5-(3-chloro-4-fluorophenyl)-1H-indole was prepared by coupling 1-benzyl-5-bromo-1H-indole (1.46 g, 5.10 mmol), and 3-chloro-4-fluorophenylboronic acid (1.08 g, 6.19 mmol), [1,1'-bis(diphenylphosphino)ferrocene] dichloropalladium(II) complex with dichloromethane (1:1) (0.209 g, 0.256 mmol), potassium carbonate (1.44 g, 10.4 mmol) in dioxane (51 mL) and water (5 mL), following the procedure described in Step 1 of Example 11. Purification by flash chromatography (Biotage apparatus) using hexane as an eluant and drying 60° C. furnished the title compound as a light brown gum (0.706 g, 41%). $^1$HNMR (200 MHz, DMSO-$d_6$): δ 7.8–7.9 (m, 2H), 7.6–7.7 (m, 1H), 7.4–7.6 (m, 3H), 7.15–7.4 (m, 6H), 6.55 (d, 1H, J=2.5 Hz), and 5.45 ppm (s, 2H).

Step 2

Ethyl [1-benzyl-5-(3-chloro-4-fluorophenyl)-1H-indol-3-yl](oxo)acetate

Ethyl [1-benzyl-5-(3-chloro-4-fluorophenyl)-1H-indol-3-yl](oxo)acetate was prepared from 1-benzyl-5-(3-chloro-4-fluorophenyl)-1H-indole (0.705 g, 2.10 mmol), oxalyl chloride (0.73 mL, 8.4 mmol), and ethanol (6 mL) according to the procedure described in Step 3 of Example 1. Purification by flash chromatography (Biotage apparatus) using 5–10% ethyl acetate in hexane as an eluant afforded the title compound as a yellow solid (0.616 g, 67%), mp: 148–149° C. Mass spectrum (+APCI, [M+H]$^+$) m/z 436; $^1$HNMR (400 MHz, DMSO-$d_6$): δ 8.75 (s, 1H), 8.4 (d, 1H, J=2.0 Hz), 7.85 (dd, 1H, J=7.1 Hz and 2.4 Hz), 7.6–7.7 (m, 3H), 7.5 (t, 1H, J=8.9 Hz), 7.25–7.35 (m, 5H), 5.65 (s, 2H), 4.35 (q, 2H, J=7.1 Hz), and 1.35 ppm (t, 3H, J=7.1 Hz).

Step 3

[1-Benzyl-5-(3-chloro-4-fluorophenyl)-1H-indol-3-yl](oxo)acetic acid

[1-Benzyl-5-(3-chloro-4-fluorophenyl)-1H-indol-3-yl](oxo)acetic acid was prepared from ethyl [1-benzyl-5-(3-chloro-4-fluorophenyl)-1H-indol-3-yl](oxo)acetate (0.540 g, 1.24 mmol), and potassium hydroxide (0.218 g, 3.89 mmol) in THF (6 mL) and water (6 mL) according to the procedure described in Step 4 of Example 5. Purification by crystallization from methylene chloride/hexane and drying at 85° C. furnished the title compound as a white solid (0.319 g, 63%), mp: 145–146° C. (dec.). Mass spectrum (+APCI, [M+H]$^+$) m/z 408; $^1$HNMR (400 MHz, DMSO-d$_6$): δ 13.8–14.3 (br s, 1H), 8.75 (s, 1H), 8.4 (d, 1H, J=1.7 Hz), 7.8 (dd, 1H, J=7.2 Hz and 2.3 Hz), 7.65–7.7 (m, 2H), 7.6 (dd, 1H, J=8.5 Hz and 2.0 Hz), 7.5 (t, 1H, J=8.9 Hz), 7.25–7.35 (m, 5H), and 5.6 ppm (s, 2H).

Elemental Analysis for C$_{23}$H$_{15}$ClFNO$_3$.H$_2$O: Calculated: C, 67.44; H, 3.74; N, 3.42. Found: C, 67.24; H, 3.6; N, 3.36.

EXAMPLE 16

{1-Benzyl-5-[3,5-bis(trifluoromethyl)phenyl]-1H-indol-3-yl}(oxo)acetic acid

Step 1

1-Benzyl-5-[3,5-bis(trifluoromethyl)phenyl]-1H-indole

1-Benzyl-5-[3,5-bis(trifluoromethyl)phenyl]-1H-indole was prepared by coupling 1-benzyl-5-bromo-1H-indole (1.44 g, 5.03 mmol), and 3,5-bis-(trifluoromethyl) phenylboronic acid (1.63 g, 6.32 mmol), using [1,1'-bis(diphenylphosphino)ferrocene]dichloropalladium (II) complex with dichloromethane (1:1) (0.211 g, 0.258 mmol), and potassium carbonate (1.38 g, 9.98 mmol) in dioxane (54 mL) and water (5.4 mL) following the procedure described in Step 1 of Example 11. The reaction mixture was heated to 85° C. for 3 hours. Purification by HPLC using 10% methylene chloride in hexane as the mobile phase furnished the title compound as a light yellow solid (1.08 g, 51%), mp: 90–95° C. $^1$HNMR (200 MHz, DMSO-d$_6$): δ 8.3 (s, 2H), 8.1 (s, 1H), 8.0 (s, 1H), 7.6 (s, 3H), 7.15–7.4 (m, 5H), 6.6 (d, 1H, J=2.6 Hz), and 5.5 ppm (s, 2H).

Step 2

Ethyl {1-benzyl-5-[3,5-bis(trifluoromethyl)phenyl]-1H-indol-3-yl}(oxo)acetate

Ethyl 2-{1-benzyl-5-[3,5-bis(trifluoromethyl)phenyl]-1H-indol-3-yl}-2-oxoacetate was prepared from 1-benzyl-5-[3,5-bis(trifluoromethyl)phenyl]-1H-indole (1.07 g, 2.56 mmol), oxalyl chloride (1.3 mL, 15 mmol), and ethanol (6 mL) following the procedure described in Step 3 of Example 1. Purification by HPLC (reverse phase column) using 85% acetonitrile and 0.1% trifluoroacetic acid in water as the mobile phase yielded the title compound as a light yellow solid (0.746 g, 56%). $^1$HNMR (300 MHz, DMSO-d$_6$): δ 8.8 (s, 1H), 8.5 (s, 1H), 8.3 (s, 2H), 8.1 (s, 1H), 7.75 (s, 2H), 7.25–7.4 (m, 5H), 5.65 (s, 2H), 4.35 (q, 2H, J=7.5 Hz), and 1.35 ppm (t, 3H, J=7.5 Hz).

Step 3

{1-Benzyl-5-[3,5-bis(trifluoromethyl)phenyl]-1H-indol-3-yl}(oxo)acetic acid

{1-Benzyl-5-[3,5-bis(trifluoromethyl)phenyl]-1H-indol-3-yl}(oxo)acetic acid was prepared from ethyl {1-benzyl-5-[3,5-bis(trifluoromethyl)phenyl]-1H-indol-3-yl}(oxo)acetate (0.737 g, 1.42 mmol), potassium hydroxide (0.260 g, 4.63 mmol) in THF (9 mL) and water (9 mL) according to the procedure described in Step 4 of Example 5. Purification by crystallization from acetonitrile and drying at 88° C. furnished the title compound as a white solid (0.326 g, 47%), mp: 206–207° C. Mass spectrum (+APCI, [M+H]$^+$) m/z 492; $^1$HNMR (400 MHz, DMSO-d$_6$): δ 13.8–14.3 (br s, 1H), 8.75 (s, 1H), 8.5 (s, 1H), 8.25 (s, 2H), 8.1 (s, 1H), 7.75 (s, 2H), 7.25–7.35 (m, 5H), and 5.6 ppm(s, 2H).

Elemental Analysis for C$_{25}$H$_{15}$F$_6$NO$_3$: Calculated: C, 61.11; H, 3.08; N, 2.85. Found: C, 60.91; H, 2.87; N, 2.83.

EXAMPLE 17

{1-Benzyl-7-[4-(trifluoromethoxy)phenyl]-1H-indol-3-yl}(oxo)acetic acid

Step 1

1-Benzyl-7-bromo-1H-indole

1-Benzyl-7-bromo-1H-indole was prepared from 7-bromo-1H-indole (0.500 g, 2.55 mmol), sodium hydride (0.285 g, 7.13 mmol of 60% dispersion on mineral oil), benzyl bromide (0.67 mL, 5.6 mmol) in DMF (5 mL). The reaction mixture was stirred for 1 hour after the addition of sodium hydride and for 1 hour after the addition of benzyl bromide. The compound was purified by flash chromatography (using hexane as an eluant) and dried at 60° C. for 30 minutes to yield a cream-colored solid (0.508 g, 70%), mp: 74–75° C. $^1$HNMR (300 MHz, DMSO-d$_6$): δ 7.5–7.65 (m, 2H), 7.15–7.35 (m, 4H), 6.8–7.0 (m, 3H), 6.6 (s, 1H), and 5.8 ppm (s, 2H).

Step 2

1-Benzyl-7-[4-(trifluoromethoxy)phenyl]-1H-indole

1-Benzyl-7-bromo-1H-indole (0.677 g, 2.37 mmol) was coupled to 4-trifluoromethoxyphenylboronic acid (0.585 g, 2.84 mmol), using [1,1'-bis(diphenylphosphino)ferrocene] dichloropalladium (II) complex with dichloromethane (1:1) (0.0585 g, 0.0716 mmol), and potassium carbonate (0.492 g, 3.56 mmol), in dioxane (18 mL) and water (1.8 mL), according to the procedure described in Step 1 of Example 11. Purication by HPLC using hexane as the mobile phase yielded the title compound as a sage green solid (0.432 g, 50%). $^1$HNMR (300 MHz, DMSO-d$_6$): δ 7.65 (d, 1H, J=7.5 Hz), 7.5 (d, 1H, J=3.8 Hz), 7.15–7.35 (m, 4H), 7.0–7.15 (m, 4H), 6.8 (d, 1H, J=7.5 Hz), 6.65 (d, 1H, J=3.8 Hz), 6.25 (d, 2H, J=7.5 Hz), and 5.05 ppm (s, 2H).

Step 3

Ethyl {1-benzyl-7-[4-(trifluoromethoxy)phenyl]-1H-indol-3-yl}(oxo)acetate

Ethyl {1-benzyl-7-[4-(trifluoromethoxy)phenyl]-1H-indol-3-yl}(oxo)acetate was prepared from 1-benzyl-7-[4-(trifluoromethoxy)phenyl]-1H-indole (0.421 g, 1.15 mmol), oxalyl chloride (0.60 mL, 6.9 mmol), and ethanol (3 mL) following the procedure described in Step 3 of Example 1. Purification by flash chromatography (Biotage apparatus) using 3–7.5% ethyl acetate in hexane as an eluant yielded the title compound as a yellow gum (0.328 g, 61%). $^1$HNMR (300 MHz, DMSO-d$_6$): δ 8.7 (s, 1H), 8.35 (d, 1H, J=7.7 Hz), 7.35 (t, 1H, J=7.7 Hz), 7.0–7.3 (m, 8H), 6.3 (d, 2H, J=7.7 Hz), 5.25 (s, 2H), 4.35 (q, 2H, J=7.4 Hz), and 1.35 ppm (t, 3H, J=7.3 Hz).

Step 4

{1-Benzyl-7-[4-(trifluoromethoxy)phenyl]-1H-indol-3-yl}(oxo)acetic acid

{1-Benzyl-7-[4-(trifluoromethoxy)phenyl]-1H-indol-3-yl}(oxo)acetic acid was prepared from ethyl {1-benzyl-7-[4-(trifluoromethoxy)phenyl]-1H-indol-3-yl}(oxo)acetate (0.318 g, 0.680 mmol), and potassium hydroxide (0.123 g, 2.19 mmol) in THF (3 mL) and water (3 mL) according to the procedure described in Step 4 of Example 5. Purification by crystallization from isopropanol and drying for 12 hours at 80° C. yielded the title compound as a white solid (0.171 g, 57%), mp: 177–178° C. Mass spectrum (–ESI, [M–H]$^-$) m/z 438; $^1$HNMR (500 MHz, DMSO-d$_6$): δ 13.8–14.2 (br s, 1H), 8.65 (s, 1H), 8.35 (dd, 1H, J=7.9 Hz and 1.1 Hz), 7.35 (t, 1H, J=7.6 Hz), 7.2–7.25 (m, 4H), 7.1 (t, 1H, J=7.3 Hz), 7.0–7.05 (m, 3H), 6.25 (d, 2H, J=7.3 Hz), and 5.6 ppm (s, 2H).

Elemental Analysis for C$_{24}$H$_{16}$F$_3$NO$_4$: Calculated: C, 65.61; H, 3.67; N, 3.19. Found: C, 65.48; H, 3.44; N, 3.16.

EXAMPLE 18

[1-Benzyl-7-(3-chloro-4-fluorophenyl)-1H-indol-3-yl](oxo)acetic acid

Step 1

1-Benzyl-7-(3-chloro-4-fluorophenyl)-1H-indole

1-Benzyl-7-(3-chloro-4-fluorophenyl)-1H-indole was prepared by coupling 1-benzyl-7-bromo-1H-indole (0.691 g, 2.41 mmol), and 3-chloro-4-fluorophenylboronic acid (0.538 g, 3.09 mmol), using [1,1'-bis(diphenylphosphino)ferrocene]dichloropalladium (II) complex with dichloromethane (1:1) (0.0628 g, 0.0769 mmol), and potassium carbonate (0.502 g, 3.63 mmol) in dioxane (18 mL) and water (1.8 mL) following the procedure described in Step 1 of Example 11. Purification by HPLC using 1.5% ethyl acetate in hexane as the mobile phase furnished the title compound as a clear gum (0.189 g, 23%). $^1$HNMR (300 MHz, DMSO-$d_6$): δ 7.65 (d, 1H, J=7.5 Hz), 7.5 (s, 1H), 7.3 (t, 1H, J=8.3 Hz), 7.05–7.2 (m, 6H), 6.85 (d, 1H, J=7.5 Hz), 6.65 (d, 1H, J=3.8 Hz), 6.3–6.4 (m, 2H), and 4.95–5.2 ppm (m, 2H).

Step 2

Ethyl [1-benzyl-7-(3-chloro-4-fluorophenyl)-1H-indol-3-yl](oxo)acetate

Ethyl [1-benzyl-7-(3-chloro-4-fluorophenyl)-1H-indol-3-yl](oxo)acetate was prepared from 1-benzyl-7-(3-chloro-4-fluorophenyl)-1H-indole (0.182 g, 0.542 mmol), oxalyl chloride (0.28 mL, 3.3 mmol), and ethanol (0.75 mL) following the procedure described in Step 3 of Example 1. Purification by HPLC using 20% ethyl acetate in hexane as the mobile phase yielded the title compound as a hard yellow gum (0.143 g, 61%). $^1$H NMR (300 MHz, DMSO-$d_6$): δ 8.7 (s, 1H), 8.35 (d, 1H, J=7.5 Hz), 7.3–7.4 (m, 2H), 7.0–7.25 (m, 6H), 6.35 (d, 2H, J=7.5 Hz), 5.35 (d, 1H, J=15.8 Hz), 5.15 (d, 1H, J=15.8 Hz), 4.35 (q, 2H, J=7.5 Hz), and 1.35 ppm (t, 3H, J=7.5 Hz).

Step 3

[1-Benzyl-7-(3-chloro-4-fluorophenyl)-1H-indol-3-yl](oxo)acetic acid

[1-Benzyl-7-(3-chloro-4-fluorophenyl)-1H-indol-3-yl](oxo)acetic acid was prepared from ethyl 2-[1-benzyl-7-(3-chloro-4-fluorophenyl)-1H-indol-3-yl]-2-oxoacetate (0.139 g, 0.319 mmol), and potassium hydroxide (0.076 g, 1.35 mmol) in THF (2.5 mL) and water (2.5 mL) following the procedure described in Step 4 of Example 5. Following work-up, and trituration of the residue with hexane, a solid was obtained. Drying for 12 hours at 82° C. yielded the title compound as a yellow solid (0.0836 g, 64%), mp: 153–156° C. Mass spectrum (–ESI, [M–H]$^-$) m/z 406; $^1$HNMR (500 MHz, DMSO-$d_6$): δ 13.8–14.2 (br s, 1H), 8.65 (s, 1H), 8.35 (m, 1H), 7.3–7.35 (m, 2H), 7.05–7.2 (m, 5H), 7.0 (s, 1H, J=7.1 Hz), 6.35 (d, 2H, J=6.9 Hz), 5.35 (d, 1H, J=16.6 Hz), and 5.15 ppm (d, 1H, J=16.6 Hz).

Elemental Analysis for $C_{23}H_{15}ClFNO_3$: Calculated: C, 67.74; H, 3.71; N, 3.43. Found: C, 67.53; H, 3.9; N, 3.3.

EXAMPLE 19

{1-(4-tert-Butylbenzyl)-5-[4-(trifluoromethoxy)phenyl]-1H-indol-3-yl}(oxo)acetic acid Step 1

1-[4-(tert-Butyl)benzyl]-5-[4-(trifluoromethoxy)phenyl]-1H-indole

1-[4-(tert-Butyl)benzyl]-5-[4-(trifluoromethoxy)phenyl]-1H-indole was prepared by coupling 1-[4-(tert-Butyl)benzyl]-5-bromo-1H-indole (5.34 g, 15.6 mmol), and 4-trifluoromethoxyphenyl boronic acid (3.86 g, 18.7 mmol), using [1,1'-bis(diphenylphosphino)ferrocene]dichloropalladium(II) complex with dichloromethane (1:1) (0.453 g, 0.555 mmol), and potassium carbonate (3.22 g, 23.3 mmol) in dioxane (120 mL) and water (11.8 mL) following the procedure described in Step 1 of Example 11. Purification by flash chromatography (Biotage apparatus) using hexane as the mobile phase yielded a dark yellow gum that solidified upon standing to a light yellow solid (2.53 g, 38%). $^1$HNMR (300 MHz, DMSO-$d_6$): δ 7.95 (s, 1H), 7.75 (d, 2H, J=7.7 Hz), 7.55–7.6 (m, 2H), 7.45 (d, 3H, J=7.7 Hz), 7.35 (d, 2H, J=7.7 Hz), 7.15 (d, 2H, J=7.7 Hz), 6.45 (d, 1H, J=3.9 Hz), 5.4 (s, 2H), and 1.2 ppm (s, 9H).

Step 2

Ethyl{1-[4-(tert-butyl)benzyl]-5-[4-(trifluoromethoxy)phenyl]-1H-indol-3-yl}(oxo)acetate Ethyl {1-[4-(tert-butyl)benzyl]-5-[4-(trifluoromethoxy)phenyl]-1H-indol-3-yl}(oxo)acetate was prepared from 1-[4-(tert-butyl)benzyl]-5-[4-(trifluoromethoxy)phenyl]-1H-indole (2.52 g, 5.95 mmol), oxalyl chloride (1.6 mL, 18 mmol), and ethanol (5 mL) following the procedure described in Step 3 of Example 1. Purification by reverse phase HPLC using 92% acetonitrile and 8% water as the mobile phase followed by drying for 12 hours at 82° C. yielded the title compound as a light yellow solid (1.84 g, 59%), mp: 141–142° C. Mass spectrum (+ESI, [M+H]$^+$) m/z 524; $^1$HNMR (500 MHz, DMSO-$d_6$): δ 8.7 (s, 1H), 8.4 (d, 1H J=1.5 Hz), 7.75–8.0 (m, 3H), 7.6 (dd, 1H, J=8.6 Hz and 1.8 Hz), 7.45 (d, 2H, J=8.1 Hz), 7.35 (d, 2H, J=8.4 Hz), 7.25 (d, 2H, J=8.4 Hz), 5.6 (s, 2H), 4.35 (q, 2H, J=7.1 Hz), 1.35 (t, 3H, J=7.0 Hz), and 1.2 ppm (s, 9H).

Elemental Analysis for $C_{30}H_{28}F_3NO_4$: Calculated: C, 68.82; H, 5.39; N, 2.68; Found: C, 68.84; H, 5.69; N, 2.57.

Step 3

{1-(4-tert-Butylbenzyl)-5-[4-(trifluoromethoxy)phenyl]-1H-indol-3-yl}(oxo)acetic acid {1-[4-(tert-Butyl)benzyl]-5-[4-(trifluoromethoxy)phenyl]-1H-indol-3-yl}(oxo)acetic acid was prepared from ethyl {1-[4-(tert-butyl)benzyl]-5-[4-(trifluoromethoxy)phenyl]-1H-indol-3-yl}(oxo)acetate (1.72 g, 3.29 mmol), and potassium hydroxide (0.614 g, 10.9 mmol) in THF (20 mL) and water (20 mL) following the procedure described in Step 4 of Example 5. Following work-up, and trituration of the residue with hexane, a solid was obtained. Crystallization from methylene chloride/hexane and drying for 10 hours at 82° C. yielded the title compound as a yellow solid (1.12 g, 69%), mp: 158–160° C. Mass spectrum (–ESI, [M–H]$^-$) m/z 494; $^1$HNMR (500 MHz, DMSO-$d_6$): δ 13.8–14.1 (br s, 1H), 8.7 (s, 1H), 8.4 (d, 1H, J=1.4 Hz), 7.75 (d, 2H, J=8.7 Hz), 7.7 (d, 1H, J=8.7 Hz), 7.6 (dd, 1H, J=8.6 Hz and 1.7 Hz), 7.45 (d, 2H, J=8.2 Hz), 7.35 (d, 2H, J=8.4 Hz), 7.25 (d, 2H, J=8.4 Hz), 5.6 (s, 2H), and 1.2 ppm (s, 9H).

Elemental Analysis for $C_{28}H_{24}F_3NO_4$: Calculated: C, 67.87; H, 4.88; N, 2.83. Found: C, 67.69; H, 4.83; N, 2.52.

EXAMPLE 20

{1-Benzyl-4-[4-(trifluoromethoxy)phenyl]-1H-indol-3-yl}(oxo)acetic acid

Step 1

1-Benzyl-4-[4-(trifluoromethoxy)phenyl]-1H-indole 1-benzyl-4-[4-(trifluoromethoxy)phenyl]-1H-indole was prepared by coupling 1-benzyl-4-bromo-1H-indole (0.787 g, 2.75 mmol), and 4-trifluoromethoxyphenylboronic acid (0.683 g, 3.32 mmol), using [1,1'-bis(diphenylphosphino)ferrocene]dichloropalladium (II) complex with dichloromethane (1:1) (0.0679 g, 0.0831 mmol), and potassium carbonate (0.575 g, 4.16 mmol) in dioxane (21 mL) and water (2.1 mL) following the procedure described in Step 1 of Example 11. Purification by HPLC using hexane as the mobile phase yielded the title compound as a light yellow gum (0.246 g, 24%). $^1$HNMR (300 MHz, DMSO-$d_6$): δ 6 7.75 (d, 2H, J=8.3 Hz), 7.65 (d, 1H, J=2.3 Hz), 7.45–7.55 (m, 3H), 7.1–7.4 (m, 7H), 6.6 (d, 1H, J=2.3 Hz), and 5.45 ppm (s, 2H).

Step 2

Ethyl {1-benzyl-4-[4-(trifluoromethoxy)phenyl]-1H-indol-3-yl}(oxo)acetate

Ethyl {1-benzyl-4-[4-(trifluoromethoxy)phenyl]-1H-indol-3-yl}(oxo)acetate was prepared from 1-benzyl-4-[4-(trifluoromethoxy)phenyl]-1H-indole (0.243 g, 0.661 mmol), oxalyl chloride (1.03 mL, 13.0 mmol), and ethanol (5 mL) according to the procedure described in Step 3 of Example 1. Purification was carried out by reverse phase HPLC using 22% water in acetonitrile as the mobile phase. Extraction with ethyl acetate, washing with brine, and evaporation to dryness afforded the title compound as a yellow gum (0.169 g, 55%). $^1$HNMR (300 MHz, DMSO-$d_6$): δ 8.65 (s, 1H), 7.65 (d, 1H, J=7.5 Hz), 7.3–7.45 (m, 10H), 7.2 (d, 1H, J=7.5 Hz), 5.65 (s, 2H), 4.25 (q, 2H, J=7.3 Hz), and 1.35 ppm (t, 3H, J=7.5 Hz).

Step 3

{1-Benzyl-4-[4-(trifluoromethoxy)phenyl]-1H-indol-3-yl}(oxo)acetic acid

{1-Benzyl-4-[4-(trifluoromethoxy)phenyl]-1H-indol-3-yl}(oxo)acetic acid was prepared from ethyl {1-benzyl-4-[4-(trifluoromethoxy)phenyl]-1H-indol-3-yl}(oxo)acetate (0.167 g, 0.357 mmol), and potassium hydroxide (0.103 g, 1.84 mmol) in THF (5 mL) and water (5 mL), according to the procedure described in Step 4 of Example 5. Drying for 12 hours at 90° C. furnished the title compound as a light yellow solid (0.131 g, 83%), mp: 167–169° C. (dec.). Mass spectrum (+ESI, [M+H]$^+$) m/z 440; $^1$HNMR (500 MHz, DMSO-$d_6$): δ 13.5–14.0 (br s, 1H), 8.65 (s, 1H), 7.65 (d, 1H, J=8.2 Hz), 7.25–7.4 (m, 10H), 7.15 (d, 2H, J=7.3 Hz), and 5.6 ppm (s, 2H).

Elemental Analysis for $C_{24}H_{16}F_3NO_4$: Calculated: C, 65.61; H, 3.67; N, 3.19. Found: C, 65.57; 3.50; N, 3.16.

EXAMPLE 21

[1-Benzyl-6-(3-chlorophenyl)-1H-indol-3-yl](oxo)acetic acid

Step 1

1-Benzyl-6-(3-chlorophenyl)-1H-indole

3-Chlorophenylboronic acid (1.21 g, 7.76 mmol) was added in four poritions to the mixture of 1-benzyl-6-bromo-1H-indole (1.12 g, 3.91 mmol), palladium(II) acetate (0.0191 g, 0,0850 mmol), and tetrabutylammonium bromide (1.26 g, 3.91 mmol) in water (22.5 mL) and THF (2.5 mL) while heating at 70° C. for 4 hours. The reaction mixture was allowed to cool to room temperature and 2N hydrochloric acid was slowly added. The mixture was extracted with ethyl acetate, washed with water and brine, dried over anhydrous magnesium sulfate, filtered and evaporated to dryness. The residue was purified by flash chromatography (Biotage apparatus) using 0–100% ethyl acetate in hexane as an eluant. Drying at 60° C. for 40 minutes yielded (0.621 g, 50%) of 1-benzyl-6-(3-chlorophenyl)-1H-indole as a yellow gum. Mass spectrum (+ESI, [M+H]$^+$) m/z 318; $^1$HNMR (500 MHz, DMSO-$d_6$): δ 7.85 (s, 1H), 7.75 (t, 1H, J=1.8 Hz), 7.6–7.65 (m, 2H), 7.55 (d, 1H, J=3.1 Hz), 7.45 (t, 1H, J=7.8 Hz), 7.25–7.35 (m, 4H), 7.2–7.25 (m, 3H), 6.5 (d, 1H, J=3.1 Hz), and 5.5 ppm (s, 2H).

Elemental Analysis for $C_{21}H_{16}ClN$: Calculated: C, 79.36; H, 5.07; N, 4.41. Found: C, 79.32; H, 5.21; N, 4.28.

Step 2

Ethyl 2-[1-benzyl-6-(3-chlorophenyl)-1H-indol-3-yl]-2-oxoacetate

Ethyl [1-benzyl-6-(3-chlorophenyl)-1H-indol-3-yl](oxo)acetate was prepared from 1-benzyl-6-(3-chlorophenyl)-1H-indole (0.591 g, 1.86 mmol), oxalyl chloride (0.49 mL, 5.6 mmol), and ethanol (2 mL) following the procedure described in Step 3 of Example 1. Purification by flash chromatography using 5–100% ethyl acetate in hexane as an eluant yielded the title compound as a hard reddish gum (0.520 g, 67%). Mass spectrum (+ESI, [M+H]$^+$) m/z 418; $^1$HNMR (500 MHz, DMSO-$d_6$): δ 8.7 (s, 1H), 8.25 (d, 1H, J=8.2 Hz), 8.0 (s, 1H), 7.8 (s, 1H), 7.65–7.0 (m, 2H), 7.5 (t, 1H, J=7.9 Hz), 7.4 (d, 1H, J=0.92 Hz), 7.35–7.4 (m, 4H), 7.25–7.3 (m, 1H), 5.7 (s, 2H), 4.35 (q, 2H, J=7.1 Hz), and 1.35 ppm (t, 3H, J=7.2 Hz).

Step 3

[1-Benzyl-6-(3-chlorophenyl)-1H-indol-3-yl](oxo)acetic acid

{1-Benzyl-6-(3-chlorophenyl)-1H-indol-3-yl}(oxo)acetic acid was prepared from ethyl [1-benzyl-6-(3-chlorophenyl)-1H-indol-3-yl](oxo)acetate (0.489 g, 1.17 mmol), and potassium hydroxide (0.214 g, 3.81 mmol) in THF (10 mL) and water (10 mL), according to the procedure described in Step 4 of Example 5. Crystallization from acetonitrile and drying for 24 hours at 94° C. furnished the title compound as a yellow solid (0.275 g, 60%), mp: 186–188° C. Mass spectrum (−ESI, [M−H]$^-$) m/z 388; $^1$HNMR (500 MHz, DMSO-$d_6$): δ 13.8–14.2 (br s, 1H), 8.7 (s, 1H), 8.25 (d, 1H, J=8.4 Hz), 8.0 (d, 1H, J=0.76 Hz), 7.75 (t, 1H, J=1.8 Hz), 7.65–7.7 (m, 2H), 7.5 (t, 1H, J=7.9 Hz), 7.4 (m, 1H), 7.3–7.4 (m, 4H), 7.25–7.3 (m, 1H), and 5.7 ppm (s, 1H).

Elemental Analysis for $C_{23}H_{16}ClNO_3 \cdot 0.05\ H_2O$: Calculated: C, 70.70; H, 4.15; N, 3.58. Found: C, 70.45; H, 3.97; N, 3.71.

EXAMPLE 22

{1-Benzyl-5-[3-(trifluoromethoxy)phenyl]-1H-indol-3-yl}(oxo)acetic acid

Step 1

1-Benzyl-5-[3-(trifluoromethoxy)phenyl]-1H-indole

1-Benzyl-5-[3-(trifluoromethoxy)phenyl]-1H-indole was prepared by coupling 1-benzyl-5-bromo-1H-indole (2.28 g, 7.97 mmol), and 3-(trifluoromethoxy)phenylboronic acid (1.66 g, 8.06 mmol), using potassium carbonate (2.75, 19.9 mmol), palladium(II) acetate (0.0731 g, 0.326 mmol), and tetrabutylammonium bromide (2.78 g, 8.62 mmol) in water (45 mL) and THF (5 mL), according to the procedure described in Step 1 of Example 21. Following work-up the residue was purified by reverse phase HPLC using 81% acetonitrile and 0.1% TFA in water as the mobile phase. Evaporation of the acetonitrile, extraction of the aqueous phase with ethyl acetate, and evaporation to dryness afforded the title compound as an orange solid (1.10 g, 38%), mp: 62–65° C. Mass spectrum (+ESI, [M+H]$^+$) m/z 368.5; $^1$HNMR (500 MHz, DMSO-$d_6$): δ 7.9 (s, 1H), 7.7 (m, 1H), 7.5–7.6 (m, 4H), 7.45 (dd, 1H, J=8.6 Hz and 1.8 Hz), 7.2–7.3 (m, 6H), 6.55 (m, 1H), and 5.45 ppm (s, 1H).

Elemental Analysis for $C_{22}H_{16}F_3NO$: Calculated: C, 71.93; H, 4.39; N, 3.81. Found: C, 71.53; H, 4.16; N, 3.79.

Step 2

Ethyl {1-benzyl-5-[3-(trifluoromethoxy)phenyl]-1H-indol-3-yl}(oxo)acetate

Ethyl {1-benzyl-5-[3-(trifluoromethoxy)phenyl]-1H-indol-3-yl}(oxo)acetate was prepared from 1-benzyl-5-[3-(trifluoromethoxy)phenyl]-1H-indole (1.06 g, 2.89 mmol), oxalyl chloride (1.04 mL, 13.0 mmol), and ethanol (1.5 mL), following the procedure described in Step 3 of Example 1. Purification by flash chromatography using 5–10% ethyl acetate in hexane as an eluant yielded the title compound as a light brown gum (1.14 g, 84%). Mass spectrum (+ESI, [M+H]$^+$) m/z 468; $^1$HNMR (500 MHz, DMSO-d$_6$): δ 8.75 (s, 1H), 8.45 (d, 1H, J=1.4 Hz), 7.7 (m, 2H), 7.6–7.65 (m, 3H), 7.25–7.4 (m, 6H), 5.65 (s, 2H), 4.35 (q, 2H, J=7.1 Hz), and 1.35 ppm (t, 3H, J=7.2 Hz).

Elemental Analysis for C$_{26}$H$_{20}$F$_3$NO$_4$: Calculated: C, 66.81; H, 4.31; N, 3.00. Found: C, 66.82; H, 4.28; N, 2.98.

Step 3

{1-Benzyl-5-[3-(trifluoromethoxy)phenyl]-1H-indol-3-yl}(oxo)acetic acid

1-Benzyl-5-[3-(trifluoromethoxy)phenyl]-1H-indol-3-yl}(oxo)acetic acid was prepared from ethyl {1-benzyl-5-[3-(trifluoromethoxy)phenyl]-1H-indol-3-yl}(oxo)acetate (1.1 g, 2.4 mmol), and potassium hydroxide (0.44 g, 7.8 mmol) in THF (25 mL) and water (25 mL), according to the procedure described in Step 4 of Example 5. Crystallization from methylene chloride/hexane yielded the title compound as a light yellow solid (0.596 g, 54%), mp: 141–142° C. Mass spectrum (+ESI, [M+H]$^+$) m/z 440; $^1$HNMR (500 MHz, DMSO-d$_6$): δ 13.8–14.2 (br s, 1H), 8.75 (s, 1H), 8.45 (s, 1H), 7.7 (m, 2H), 7.6 (t, 3H, J=4.4 Hz), 7.25–7.35 (m, 6H), and 5.65 ppm (s, 2H).

Elemental Analysis for C$_{24}$H$_{16}$F$_3$NO$_4$: Calculated: C, 65.61; H, 3.67; N, 3.19. Found: C, 65.41; H, 3.39; N, 3.09.

EXAMPLE 23

(1-Benzyl-6-phenyl-1H-indol-3-yl)(oxo)acetic acid

Step 1

1-Benzyl-6-phenyl-1H-indole (15)

1-Benzyl-6-phenyl-1H-indole was prepared by coupling 1-benzyl-6-bromo-1H-indole (3.48 g, 12.2 mmol), and phenylboronic acid (1.63 g, 13.4 mmol), using tetrakis(triphenylphosphine)palladium (0.976 g, 0.846 mmol), and sodium carbonate (5.2 g, 49 mmol) in water (25 mL), ethanol (5 mL), and toluene (55 mL), according to the procedure described in Step 2 of Example 2. Purification by flash chromatography using 0–2.5% ethyl acetate in hexane as an eluant afforded the title compound as a light green solid (2.02 g, 58%), mp: 109–110° C. Mass spectrum (+ES, [M+H]$^+$) m/z 284; $^1$HNMR (500 MHz, DMSO-d$_6$): δ 7.75 (s, 1H), 7.6–7.65 (m, 3H), 7.55 (d, 1H, J=3.1 Hz), 7.45 (t, 2H, J=7.5 Hz), 7.3–7.35 (m, 4H), 7.2–7.25 (m, 3H), 6.5 (d, 1H, J=3.0 Hz), and 5.5 ppm (s, 2H).

Elemental Analysis for C$_{21}$H$_{17}$N: Calculated: C, 89.01; H, 6.05; N, 4.94. Found: C, 89.04; H, 5.87; N, 4.79.

Step 2

Ethyl (1-benzyl-6-phenyl-1H-indol-3-yl)(oxo)acetate

Ethyl (1-benzyl-6-phenyl-1H-indol-3-yl)(oxo)acetate was prepared from, 1-benzyl-6-phenyl-1H-indole (1.90 g, 6.71 mmol), oxalyl chloride (1.8 mL, 20 mmol), and ethanol (4 mL). Purification by flash chromatography, using 5–12.5% ethyl acetate in hexane as an eluant, yielded the title compound as a light yellow solid (1.98 g, 77%), mp: 121–123° C. Mass spectrum (+ES, [M+H]$^+$) m/z 384; $^1$HNMR (500 MHz, DMSO-d$_6$): δ 8.7 (s, 1H), 8.25 (d, 1H, J=8.2 Hz), 7.9 (d, 1H, J=0.46 Hz), 7.7 (d, 2H, J=7.9 Hz), 7.65 (dd, 1H, J=8.2 H and 0.76 Hz), 7.45 (t, 2H, J=7.6 Hz), 7.35–7.4 (m, 5H), 7.25–7.35 (m, 1H), 5.65 (s, 2H), 4.35 (q, 2H, J=7.1 Hz), and 1.35 ppm (t, 3H, J=7.1).

Elemental Analysis for C$_{25}$H$_{17}$NO$_3$: Calculated: C, 78.31; H, 5.52; N, 3.65. Found: C, 77.93; H, 5.40; N, 3.58.

Step 3

(1-Benzyl-6-phenyl-1H-indol-3-yl)(oxo)acetic acid (1-Benzyl-6-phenyl-1H-indol-3-yl)(oxo)acetic acid was prepared from ethyl (1-benzyl-6-phenyl-1H-indol-3-yl)(oxo)acetate (1.90 g, 4.96 mmol), and potassium hydroxide (0.856 g, 15.3 mmol) in THF (20 mL) and water (20 mL), following the procedure described in Step 4 of Example 5. Crystallization from acetonitrile and drying for 8 hours at 70° C. yielded the title compound as a light yellow solid (1.23 g, 70%), mp: 210–212° C. (dec.). Mass spectrum (+ES, [M+H]$^+$) m/z 356; $^1$ HNMR (500 MHz, DMSO-d$_6$): δ 13.8–14.2 (br s, 1H), 8.7 (s, 1H), 8.25 (d, 1H, J=8.2 Hz), 7.9 (s, 1H), 7.65 (d, 2H, J=8.1 Hz), 7.6 (d, 1H, J=8.4 Hz), 7.45 (t, 2H, J=7.7 Hz), 7.3–7.35 (m, 5H), 7.25–7.3 (m, 1H), and 5.65 ppm (s, 2H).

Elemental Analysis for C$_{23}$H$_{17}$NO$_3$: Calculated: C, 77.73; H, 4.82; N, 3.94. Found: C, 77.58; H, 4.68; N, 3.90.

EXAMPLE 24

(1-Benzyl-5-phenyl-1H-indol-3-yl)(oxo)acetic acid

Step 1

1-Benzyl-5-phenyl-1H-indole

1-Benzyl-5-phenyl-1H-indole was prepared by coupling 1-benzyl-5-bromo-1H-indole (2.72 g, 9.50 mmol), and phenylboronic acid (1.39 g, 11.4 mmol), using [1,1'-bis(diphenylphosphino)ferrocene]dichloropalladium (II) complex with dichloromethane (1:1) (0.266 g, 0.326 mmol), and potassium carbonate (2.06 g, 14.9 mmol) in dioxane (72 mL) and water (7.2 mL), following the procedure described in Step 1 of Example 11. Purification by flash chromatography (Biotage apparatus) using hexane as an eluant yielded the title compound as a light yellow solid (0.928 g, 35%), mp: 105–106° C. Mass spectrum (+ES, [M+H]$^+$) m/z 284; $^1$HNMR (500 MHz, DMSO-d$_6$): δ 7.8 (d, 1H, J=0.92 Hz), 7.65 (dd, 2H, J=8.2 Hz and 0.84 Hz), 7.5–7.55 (m, 2H), 7.35–7.45 (m, 3H), 7.2–7.3 (m, 6H), 6.55 (dd, 1H, J=3.1 Hz and 0.61 Hz), and 5.45 ppm (s, 2H).

Step 2

Ethyl 2-(1-benzyl-5-phenyl-1H-indol-3-yl)-2-oxoacetate

Ethyl {1-benzyl-5-phenyl-1H-indol-3-yl}(oxo)acetate was prepared from 1-benzyl-5-phenyl-1H-indole (0.846 g, 2.99 mmol), oxalyl chloride (0.78 mL, 9.0 mmol), and ethanol (2 mL), following the procedure described in Step 3 of Example 1. Purification by flash chromatography (Biotage apparatus) using 5–7.5% ethyl acetate in hexane as an eluant yielded the title compound as a light yellow solid (0.754 g, 66%), mp: 116–117° C. Mass spectrum (+ES, [M+H]$^+$) m/z 384; $^1$HNMR (500 MHz, DMSO-d$_6$): δ 8.7 (s, 1H), 8.4 (d, 1H, J=0.92 Hz), 7.6–7.7 (m, 3H), 7.55–7.6 (m, 1H), 7.45 (t, 2H, J=7.7 Hz), 7.3–7.4 (m, 6H), 5.65 (s, 2H), 4.35 (q, 2H, J=7.1 Hz), and 1.35 ppm (t, 3H, J=7.1 Hz).

Elemental Analysis for C$_{25}$H$_{21}$NO$_3$: Calculated: C, 78.31; H, 5.52; N, 3.65. Found: C, 78.15; H, 5.63; N, 3.51.

Step 3

(1-Benzyl-5-phenyl-1H-indol-3-yl)(oxo)acetic acid

{1-Benzyl-5-phenyl-1H-indol-3-yl}(oxo)acetic acid was prepared from ethyl {1-benzyl-5-phenyl-1H-indol-3-yl}(oxo)acetate (0.680 g, 1.77 mmol), and potassium hydroxide (0.322 g, 5.74 mmol) in THF (10 mL) and water (10 mL), following the procedure described in Step 4 of Example 5. Crystallization from acetonitrile, and drying for 3.5 hours at 70° C., yielded the title compound as a yellow solid (0.392 g, 62%), mp: 193–195° C. (dec.). Mass spectrum (+ES, [M+H]$^+$) m/z 356; $^1$ HNMR (500 MHz, DMSO-d$_6$): δ 13.7–14.2 (br s, 1H), 8.7 (s, 1H), 8.45 (d, 1H, J=0.61 Hz), 7.65 (m, 3H), 7.55 (dd, 1H, J=8.7 Hz and 1.1 Hz), 7.45 (t, 2H, J=7.6 Hz), 7.25–7.35 (m, 6H), and 5.65 ppm (s, 2H).

Elemental Analysis for C$_{23}$H$_{17}$NO$_3$: Calculated: C, 77.73; H, 4.82; N, 3.94. Found: C, 77.52; H, 4.81; N, 3.95.

EXAMPLE 25

[1-(4-Methylbenzyl)-5-phenyl-1H-indol-3-yl](oxo) acetic acid

Step 1

5-Bromo-1-(4-methylbenzyl)-1H-indole

NaH (60%, 2.53 g, 63.1 mmol) was added portionwise to a stirring solution of 5-bromoindole (8.25 g, 42.1 mmol) in DMF (80 mL) at 0° C. under a nitrogen atmosphere over a period of 10 min. The mixture was then warmed up to room temperature. After the reaction mixture was stirred at room temperature for 1 hour, 4-methylbenzyl bromide (12.0 g, 63.1 mmol) was added and the mixture was stirred at room temperature overnight. The reaction was quenched with aqueous ammonium chloride and diluted with water. The aqueous phase was extracted with ethyl acetate. The organic extract was washed with water and brine, then dried over anhydrous magnesium sulfate. This mixture was concentrated to give a crude oil (14.1 g, 71%). Crystallization from petroleum ether afforded the title compound as a white solid, m.p: 56–57° C. Mass spectrum (APCI, [M+H]$^+$) m/z 300. $^1$HNMR (400 MHz, DMSO-d6): δ 7.73 (s, 1H), 7.53 (s, 1H), 7.40 (d, 1H, J=8.9 Hz), 7.18 (d, 1H, J=10.5 Hz), 7.09 (d, 2H, J=8.2 Hz), 7.07 (d, 2H, J=8.2 Hz), 6.45 (s, 1H), 5.35 (s, 2H), and 2.22 ppm (s, 3H).

Elemental Analysis for $C_{16}H_{14}BrN$: Calculated: C, 64.02; H, 4.70; N, 4.67. Found: C, 63.66; H, 4.59; N, 4.71.

Step 2

1-(4-Methylbenzyl)-5-phenyl-1H-indole

A mixture of 5-bromo-1-(4-methylbenzyl)-1H-indole (1.0 g, 3.33 mmol), benzeneboronic acid (0.621 g, 5.0 mmol), potassium carbonate (0.691 g, 5.0 mmol), and [1'1'-bis (diphenylphosphino)-ferrocene]dichloropalladium(II) complex with methylenechloride (1:1) (0.816 g, 1.0 mmol) in dioxane-water (10:1, 16.5 mL) was stirred at 70° C. for 2 day. The reaction mixture was diluted with water and extracted with ethyl acetate. The organic extract was washed with water and brine, and then concentrated to an oil. The residue was purified by flash column chromatography using hexane/ethyl acetate (96:4) as an eluant to give the title compound as a semi-solid (0.48 g, 49%). Mass spectrum (+ESI, [M+H]$^+$) m/z 298. $^1$HNMR (300 MHz, DMSO-d$_6$): δ 7.80 (s, 1H), 7.63 (d, 2H, J=8.4 Hz), 7.48 (d, 2H, J=11.1 Hz), 7.38–7.45 (m, 3H), 7.11 (m, 4H), 6.52 (d, 2H, J=2.8 Hz), 5.38 (s, 2H), and 2.22 ppm (s, 3H).

Elemental Analysis for $C_{22}H_{19}N$: Calculated: C, 88.85; H, 6.44; N, 4.71. Found: C, 88.65; H, 6.42; N, 4.61.

Step 3

[1-(4-Methylbenzyl)-5-phenyl-1H-indol-3-yl](oxo)acetic acid

Oxalyl chloride (0.474 mL, 5.43 mmol) was added dropwise to a stirring solution of 1-(4-methylbenzyl)-5-phenyl-1H-indole (0.46 g, 1.55 mmol) in THF (15 mL) at room temperature over a period of 5 minutes under a nitrogen atmosphere. After the reaction mixture was stirred at room temperature for 4 hours, the reaction was quenched carefully with water. The aqueous mixture was extracted with ethyl acetate. The extract was washed with water, and brine, dried over anhydrous magnesium sulfate, and concentrated to give the title compound as a yellow solid (0.41 g, 72%), m.p: 195–196° C. Mass spectrum (ESI, [M+H]$^+$) m/z 370. $^1$HNMR (400 MHz, DMSO-d$_6$): δ 13.95 (br s, 1H), 8.68 (s, 1H), 8.41 (s, 1H), 7.63–7.66 (m, 3H), 7.56 (d, 1H, J=10.4 Hz), 7.47 (t, 2H, J=7.5 Hz), 7.35 (t, 1H, J=7.3 Hz), 7.22 (d, 2H, J=8.1 Hz), 7.15 (d, 2H, J=8.0 Hz), 5.56 (s, 2H), and 2.25 ppm (s, 3H).

Elemental Analysis for $C_{24}H_{19}NO_3 \cdot 0.3 H_2O$: Calculated: C, 76.91; H, 5.27; N, 3.74. Found: C, 76.85; H, 5.18; N, 3.61.

EXAMPLE 26

{1-(4-Methylbenzyl)-5-[4-(trifluoromethoxy) phenyl]-1H-indol-3-yl}(oxo)acetic acid Step 1

1-(4-Methylbenzyl)-5-[4-(trifluoromethoxy)phenyl]-1H-indole

The title compound was prepared from 5-bromo-1-(4-methylbenzyl)-1H-indole (Step 1 of Example 25) and 4-(trifluoromethoxy)phenylboronic acid in substantially the same manner, as described in Step 2 of Example 25. The product was obtained as an oil. Mass spectrum (ESI, [M+H]$^+$) m/z 382. $^1$HNMR (300 MHz, DMSO-d$_6$): δ 7.83 (s, 1H), 7.76 (d, 2H, J=8.8 Hz), 7.52 (s, 1H), 7.53 (d, 2H, J=8.1 Hz), 7.41–7.38 (m, 3H), 7.11 (m, 4H), 6.54 (d, 1H, J=3 Hz), 5.39 (s, 2H), and 2.23 ppm (s, 3H).

Elemental Analysis for $C_{23}H_{18}F_3NO$: Calculated: C, 72.43; H, 4.76; N, 3.67. Found: C, 72.38; H, 4.70; N, 3.59.

Step 2

{1-(4-Methylbenzyl)-5-[4-(trifluoromethoxy)phenyl]-1H-indol-3-yl}(oxo)acetic acid The title compound was prepared from 1-(4-methylbenzyl)-5-[4-(trifluoromethoxy)phenyl]-1H-indole and oxalyl chloride in substantially the same manner, as described in Step 3 of Example 25. The product was obtained as a yellow solid, mp: 192–193° C. Mass spectrum (ESI, [M+H]$^+$) m/z 454. $^1$HNMR (400 MHz, DMSO-d$_6$): δ 13.50 (br s, 1H), 8.70 (s, 1H), 8.42 (s, 1H), 7.77 (d, 2H, J=8.7 Hz), 7.67 (d, 1H, J=8.5 Hz), 7.58 (dd, 1H, J=8.7 Hz and 1.8 Hz), 7.45 (d, 2H, J=8.3 Hz), 7.22 (d, 1H, J=7.9 Hz), 7.15 (d, 2H, J=8.1 Hz), 5.57 (s, 2H), and 2.25 ppm (s, 3H).

Elemental Analysis for $C_{25}H_{18}F_3NO_4 \cdot 0.2 H_2O$: Calculated: C, 65.70; H, 4.06; N, 3.06. Found: C, 65.74; H, 4.05; N, 2.94.

EXAMPLE 27

{1-(4-Fluorobenzyl)-5-[4-(trifluoromethoxy) phenyl]-1H-indol-3-yl}(oxo)acetic acid Step 1

5-Bromo-1-(4-fluorobenzyl)-1H-indole

The title compound was prepared from 4-fluorobenzyl bromide and 5-bromoindole in substantially the same manner, as described in Step 1 of Example 25. The product was obtained as a white solid; mp: 57–58° C. Mass spectrum (APCI, [M+H]$^+$) m/z 304. $^1$HNMR (400 MHz, DMSO-d$_6$): δ 7.73 (d, 1H, J=1.8 Hz), 7.55 (d, 1H, J=3.2 Hz), 7.43 (d, 1H, J=8.9 Hz), 7.24–7.19 (m, 3H), 7.12 (t, 2H, J=8.9 Hz), 6.47 (d, 1H, J=3.6 Hz), 5.40 (s, 2H), and 2.22 ppm (s, 3H).

Elemental Analysis for $C_{15}H_{11}BrFN$: Calculated: C, 59.23; H, 3.65; N, 4.61. Found: C, 59.00; H, 3.55; N, 4.58.

Step 2

1-(4-Fluorobenzyl)-5-[4-(trifluoromethoxy)phenyl]-1H-indole

The title compound was prepared from 5-bromo-1-(4-fluorobenzyl)-1H-indole and 4-(trifluoromethoxy) phenylboronic acid in substantially the same manner, as described in Step 2 of Example 25. The product was obtained as an oil. Mass spectrum (ESI, [M+H]$^+$) m/z 386. $^1$HNMR (300 MHz, DMSO-d$_6$): δ 7.84 (s, 1H), 7.76 (d, 2H, J=8.7 Hz), 7.56 (s, 1H), 7.55 (d, 1H, J=9.7 Hz), 7.41–7.39 (m, 3H), 7.23 (d, 2H, J=8.1 Hz), 7.16 (d, 2H, J=8.7 Hz), 6.55 (d, 1H, J=3.1 Hz), and 5.44 ppm (s, 2H).

Step 3

{1-(4-Fluorobenzyl)-5-[4-(trifluoromethoxy)phenyl]-1H-indol-3-yl}(oxo)acetic acid The title compound was prepared from 1-(4-fluorobenzyl)-5-[4-(trifluoromethoxy)phenyl]-1H-indole and oxalyl chloride in substantially the same manner, as described in Step 3 of Example 25. The product was obtained as a white solid; mp: 158–159° C. Mass spectrum (ESI, [M+H]$^+$) m/z 458. $^1$HNMR (400 MHz, DMSO-d$_6$): δ 14.00 (br s, 1H), 8.74 (s, 1H), 8.43 (s, 1H), 7.77 (d, 2H, J=6.7 Hz), 7.70 (d, 1H, J=8.6 Hz), 7.59 (dd, 1H, J=8.7 Hz and 1.7 Hz), 7.45 (d, 2H, J=8.1 Hz), 7.40 (d, 1H, J=8.7 Hz), 7.39 (d, 1H, J=8.5 Hz), 7.18 (t, 2H, J=9.1 Hz), and 5.61 ppm (s, 2H).

Elemental Analysis for C$_{24}$H$_{15}$F$_4$NO$_4$.0.2 H$_2$O: Calculated: C, 62.53; H, 3.37; N, 3.04. Found: C, 62.31; H, 3.20; N, 3.12.

EXAMPLE 28

[1-(4-Fluorobenzyl)-5-phenyl-1H-indol-3-yl](oxo) acetic acid

Step 1

1-(4-Fluorobenzyl)-5-phenyl-1H-indole

The title compound was prepared from 5-bromo-1-(4-fluorobenzyl)-1H-indole (Step 1 of Example 27) and benzeneboronic acid in substantially the same manner, as described in Step 2 of Example 25. The product was obtained as an oil. Mass spectrum (ESI, [M+H]$^+$) m/z 302. $^1$HNMR (300 MHz, DMSO-d$_6$): δ 7.81 (s, 1H), 7.63 (d, 2H, J=8.3 Hz), 7.56–7.51 (m, 2H), 7.45–7.37 (m, 3H), 7.30–7.22 (m, 3H), 7.20–7.08 (m, 2H), 6.54 (d, 1H, J=6.0 Hz), and 5.43 ppm (s, 2H).

Step 2

[1-(4-Fluorobenzyl)-5-phenyl-1H-indol-3-yl](oxo)acetic acid

The title compound was prepared from 1-(4-fluorobenzyl)-5-phenyl-1H-indole and oxalyl chloride in substantially the same manner, as described in Step 3 of Example 25. The product was obtained as a light brown solid, mp: 165–166° C. Mass spectrum (ESI, [M+H]$^+$) m/z 374. $^1$HNMR (400 MHz, DMSO-d$_6$): δ 13.54 (br s, 1H), 8.73 (s, 1H), 8.42 (s, 1H), 7.68 (d, 1H, J=8.5 Hz), 7.64 (d, 2H, J=7.5 Hz), 7.58 (dd, 1H, J=8.6 Hz and 1.7 Hz), 7.47 (t, 2H, J=7.6 Hz), 7.39 (d, 1H, J=8.6 Hz), 7.37 (d, 1H, J=8.2 Hz), 7.34 (t, 1H, J=7.4 Hz), and 5.61 ppm (s, 2H).

Elemental Analysis for C$_{23}$H$_{16}$FNO$_3$.0.4 H$_2$O: Calculated: C, 72.59; H, 4.45; N, 3.68. Found: C, 72.58; H, 4.29; N, 3.62.

EXAMPLE 29

[1-Butyl-5-(4-chlorophenyl)-1H-indol-3-yl](oxo) acetic acid

Step 1

5-Bromo-1-butyl-1H-indole

The title compound was prepared from 1-bromobutane (11 mL, 101 mmol) and 5-bromoindole (20 g, 101 mmol) in substantially the same manner, as described in Step 1 of Example 25. The product was obtained as an oil. Mass spectrum (ESI, [M+H]$^+$) m/z 252. $^1$HNMR (300 MHz, DMSO-d$_6$): δ 7.71 (d, 1H, J=1.9 Hz), 7.46 (d, 1H, J=8.7 Hz), 7.42 (d, 1H, J=3.1 Hz), 7.22 (dd, 1H, J=6.7 Hz and J=2.0 Hz), 6.40 (d, 1H, J=3.1 Hz), 4.15 (t, 2H, J=7.0 Hz), 1.70 (q, 2H, J=7.0 Hz), 1.19 (h, 2H, J=7.47 Hz), and 0.85 ppm (t, 3H, J=7.47 Hz).

Step 2

1-Butyl-5-(4-chlorophenyl)-1H-indole

The title compound was prepared from 5-bromo-1-butyl-1H-indole and 4-chlorophenylboronic acid in substantially the same manner, as described in Step 2 of Example 25. The product was obtained as an oil. Mass spectrum (ESI, [M+H]$^+$) m/z 284. $^1$HNMR (400 MHz, DMSO-d$_6$): δ 7.81 (s, 1H), 7.67 (d, 2H, J=8.56 Hz), 7.54 (d, 1H, J=8.55 Hz), 7.46 (d, 2H, J=8.55 Hz), 7.42–7.40 (m, 2H), 6.47 (d, 1H, J=3.0 Hz), 4.18 (t, 2H, J=7.02 Hz), 1.73 (p, 2H, J=7.18 Hz), 1.24 (h, 2H, J=7.47 Hz), and 0.88 ppm (t, 3H, J=7.33 Hz).

Elemental Analysis for C$_{18}$H$_{18}$ClN: Calculated: C, 76.18; H, 6.39; N, 4.94. Found: C, 75.71; H, 6.16; N, 4.74.

Step 3

[1-Butyl-5-(4-chlorophenyl)-1H-indol-3-yl](oxo)acetic acid

The title compound was prepared from 1-butyl-5-(4-chlorophenyl)-1H-indole and oxalyl chloride in substantially the same manner, as described in Step 3 of Example 25. The product was obtained as a yellow solid, mp: 136–137° C. Mass spectrum (ESI, [M+H]$^+$) m/z 356. $^1$HNMR (400 MHz, DMSO-d$_6$): δ 13.90 (br s, 1H), 8.52 (s, 1H), 8.42 ((d, 1H, J=1.38 Hz), 7.76 (d, 1H, J=8.57 Hz), 7.70 (d, 2H, J=8.5 Hz), 7.62 (d, 1H, J=10.39 Hz), 7.53 (d, 2H, J=8.70 Hz), 4.35 (t, 2H, J=7.02 Hz), 1.79 (p, 2H, J=7.33 Hz), 1.28 (h, 2H, J=7.64 Hz), and 0.89 ppm (t, 3H, J=7.33 Hz).

Elemental Analysis for C$_{20}$H$_{18}$ClNO$_3$: Calculated: C, 67.51; H, 5.10; N, 3.94. Found: C, 67.62; H, 5.05; N, 3.81.

EXAMPLE 30

[1-Butyl-5-(3-chlorophenyl)-1H-indol-3-yl](oxo) acetic acid

Step 1

1-Butyl-5-(3-chlorophenyl)-1H-indole

The title compound was prepared from 5-bromo-1-butyl-1H-indole (Step 1 of Example 29) and 3-chlorophenylboronic acid in substantially the same manner, as described in Step 2 of Example 25. The product was obtained as an oil. Mass spectrum (APCI, [M+H]$^+$) m/z 284. $^1$HNMR (400 MHz, DMSO-d$_6$): δ 7.85 (s, 1H), 7.69 (s, 1H), 7.63 (d, 1H, J=8.36 Hz), 7.55 (d, 1H, J=8.55 Hz), 7.47–7.41 (m, 3H), 7.34 (d, 1H, J=7.94 Hz), 6.48 (d, 1H, J=3.05 Hz), 4.19 (t, 2H, J=7.01 Hz), 1.73 (p, 2H, J=7.16 Hz), 1.25 (h, 2H, J=7.46 Hz), and 0.88 ppm (t, 3H, J=7.31 Hz).

Elemental Analysis for C$_{18}$H$_{18}$ClN: Calculated: C, 76.18; H, 6.39; N, 4.94. Found: C, 76.85; H, 6.23; N, 4.81.

Step 2

[1-Butyl-5-(3-chlorophenyl)-1H-indol-3-yl](oxo)acetic acid

The title compound was prepared from 1-butyl-5-(3-chlorophenyl)-1H-indole and oxalyl chloride in substantially the same manner, as described in Step 3 of Example 25. The product was obtained as a yellow solid, mp: 108–109° C. Mass spectrum (ESI, [M+H]$^+$) m/z 356. $^1$HNMR (400 MHz, DMSO-d$_6$): δ 13.90 (br s, 1H), 8.54 (s, 1H), 8.42 ((d, 1H, J=1.36 Hz), 7.77 (d, 1H, J=8.70 Hz), 7.69 (d, 1H, J=1.70 Hz), 7.65 (d, 1H, J=9.01 Hz), 7.50 (dd, 1H, J=7.79 and 7.94 Hz), 7.42 (dd, 1H, J=7.94 and 0.92 Hz), 4.36 (t, 2H, J=7.04 Hz), 1.79 (p, 2H, J=7.26 Hz), 1.27 (h, 2H, J=7.73 Hz), and 0.89 ppm (t, 3H, J=7.36 Hz).

Elemental Analysis for C$_{20}$H$_{18}$ClNO$_3$: Calculated: C, 67.51; H, 5.10; N, 3.94. Found: C, 67.58; H, 5.08; N, 3.71.

EXAMPLE 31

[1-Butyl-5-(3-methoxyphenyl)-1H-indol-3-yl](oxo) acetic acid

Step 1

1-Butyl-5-(3-methoxyphenyl)-1H-indole

The title compound was prepared from 5-bromo-1-butyl-1H-indole (Step 1 of Example 29) and 3-methoxyphenylboronic acid in substantially the same manner, as described in Step 2 of Example 25. The product was obtained as an oil. Mass spectrum (APCI, [M+H]$^+$) m/z 280. $^1$HNMR (300 MHz, DMSO-d$_6$): δ 7.81 (s, 1H), 7.52 (d, 1H, J=8.30 Hz), 7.43–7.38 (m, 2H), 7.39 (dd, 1H, J=7.70 and 7.91 Hz), 7.22 (d, 1H, J=8.50 Hz), 7.17 (s, 1H), 6.85 (d, 1H, J=7.10 Hz), 6.46 (d, 1H, J=3.05 Hz), 4.18 (t, 2H, J=7.01 Hz), 3.81 (s, 3H), 1.73 (p, 2H, J=7.16 Hz), 1.25 (h, 2H, J=7.46 Hz), and 0.87 ppm (t, 3H, J=7.31 Hz).

Elemental Analysis for $C_{19}H_{21}NO$: Calculated: C, 76.18; H, 6.39; N, 4.94. Found: C, 76.85; H, 6.23; N, 4.81.

Step 2

[1-Butyl-5-(3-methoxyphenyl)-1H-indol-3-yl](oxo)acetic acid

The title compound was prepared from 1-butyl-5-(3-methoxyphenyl)-1H-indole and oxalyl chloride in substantially the same manner, as described in Step 3 of Example 25. The product was obtained as a yellow solid, mp: 108–109° C. Mass spectrum (ESI, [M+H]$^+$) m/z 352. $^1$HNMR (400 MHz, DMSO-d$_6$): δ 8.56 (s, 1H), 8.49 (s, 1H), 7.64 (d, 1H, J=8.55 Hz), 7.54 (d, 1H, J=8.4 Hz), 7.33 (d, 1H, J=7.03 Hz), 7.19 (d, 1H, J=6.56 Hz), 7.14 (s, 1H), 6.89 (d, 1H, J=7.33 Hz), 4.27 (t, 2H, J=7.01 Hz), 3.81 (s, 3H), 1.75 (p, 2H, J=7.24 Hz), 1.25 (h, 2H, J=7.51 Hz), and 0.87 ppm (t, 3H, J=7.33 Hz).

Elemental Analysis for $C_{21}H_{21}NO_4 \cdot 0.2 H_2O$: Calculated: C, 71.05; H, 6.08; N, 3.95. Found: C, 70.93; H, 6.03; N, 3.88.

EXAMPLE 32

[1-Butyl-5-(4-methoxyphenyl)-1H-indol-3-yl](oxo)acetic acid

Step 1

1-Butyl-5-(4-methoxyphenyl)-1H-indole

The title compound was prepared from 5-bromo-1-butyl-1H-indole (Step 1 of Example 29) and 4-methoxyphenylboronic acid in substantially the same manner, as described in Step 2 of Example 25. The product was obtained as an oil. Mass spectrum (ESI, [M+H]$^+$) m/z 280.1 HNMR (400 MHz, DMSO-d$_6$): δ 7.72 (s, 1H), 7.58 (dd, 2H, J=8.86 and 1.99 Hz), 7.54–7.49 (m, 2H), 7.37–7.35 (m, 2H), 6.98 (dd, 1H, J=7.33 and 7.34 Hz), 6.44 (d, 1H, J=3.05 Hz), 4.17 (t, 2H, J=7.01 Hz), 3.78 (s, 3H), 1.73 (p, 2H, J=7.16 Hz), 1.25 (h, 2H, J=7.46 Hz), and 0.88 ppm (t, 3H, J=7.3, 1 Hz).

Step 2

[1-Butyl-5-(4-methoxyphenyl)-1H-indol-3-yl](oxo)acetic acid

The title compound was prepared from 1-butyl-5-(4-methoxyphenyl)-1H-indole and oxalyl chloride in substantially the same manner, as described in Step 3 of Example 25. The product was obtained as a yellow solid, mp: 172–173° C. Mass spectrum (ESI, [M+H]$^+$) m/z 352. $^1$HNMR (300 MHz, DMSO-d$_6$): δ 13.90 (br s, 1H), 8.54 (s, 1H), 8.50 (s, 1H), 8.37 (s, 1H), 7.73 (d, 1H, J=8.55 Hz), 7.61–7.55 (m, 3H), 7.05 (d, 2H, J=7.03 Hz), 4.34 (t, 2H, J=7.01 Hz), 3.80 (s, 3H), 1.79 (p, 2H, J=7.24 Hz), 1.26 (h, 2H, J=7.51 Hz), and 0.89 ppm (t, 3H, J=7.33 Hz).

Elemental Analysis for $C_{21}H_{21}NO_4$: Calculated: C, 71.78; H, 6.02; N, 3.99. Found: C, 72.01; H, 5.93; N, 3.98.

EXAMPLE 33

{1-Butyl-5-[4-(trifluoromethyl)phenyl]-1H-indol-3-yl}(oxo)acetic acid

Step 1

1-Butyl-5-[4-(trifluoromethyl)phenyl]-1H-indole

The title compound was prepared from 5-bromo-1-butyl-1H-indole (Step 1 of Example 29) and 4-trifluoromethylphenylboronic acid in substantially the same manner, as described in Step 2 of Example 25. The product was obtained as an oil, mp: 52–53° C. Mass spectrum (APCI, [M+H]$^+$) m/z 318. $^1$HNMR (400 MHz, DMSO-d$_6$): δ 7.91–7.88 (m, 3H), 7.76 (d, 2H, J=8.24 Hz), 7.59 (d, 1H, J=8.55 Hz), 7.49 (d, 1H, J=8.56 Hz), 7.43 (d, 1H, J=3.06 Hz), 6.51 (d, 1H, J=3.05 Hz), 4.20 (t, 2H, J=7.01 Hz), 1.74 (p, 2H, J=7.19 Hz), 1.25 (h, 2H, J=7.48 Hz), and 0.88 ppm (t, 3H, J=7.32 Hz).

Elemental Analysis for $C_{19}H_{18}F_3N$: Calculated: C, 71.91; H, 5.72; N, 4.41. Found: C, 71.53; H, 5.61; N, 4.36.

Step 2

{1-Butyl-5-[4-(trifluoromethyl)phenyl]-1H-indol-3-yl}(oxo)acetic acid

The title compound was prepared from 1-butyl-5-[4-(trifluoromethyl)phenyl]-1H-indole and oxalyl chloride in substantially the same manner, as described in Step 3 of Example 25. The product was obtained as a light yellow solid; mp: 149–149° C. Mass spectrum (ESI, [M−H]$^-$) m/z 388. $^1$HNMR (300 MHz, DMSO-d$_6$): δ 13.90 (br s, 1H), 8.55 (s, 1H), 8.50 (s, 1H), 7.90 (d, 2H, J=8.25 Hz), 7.84–7.80 (m, 3H), 7.70 (dd, 1H, J=8.85 and 2.33 Hz), 4.37 (t, 2H, J=7.01 Hz), 1.79 (p, 2H, J=7.24 Hz), 1.28 (h, 2H, J=7.51 Hz), and 0.90 ppm (t, 3H, J=7.33 Hz).

Elemental Analysis for $C_{21}H_{18}F_3NO_3$: Calculated: C, 64.78; H, 4.66; N, 3.60. Found: C, 65.08; H, 4.76; N, 3.61.

EXAMPLE 34

[1-(4-tert-Butylbenzyl)-5-(3-methylphenyl)-1H-indol-3-yl](oxo)acetic acid

Step 1

5-Bromo-1-[4-(tert-butyl)benzyl]-1H-indole

The title compound was prepared from 4-(tert-butyl)benzyl bromide (180 g, 768 mmol) and 5-bromoindole (152 g, 768 mmol) in substantially the same manner, as described in Step 1 of Example 25. The product (257 g, 97%) was obtained as a yellow solid, mp: 108–109° C. Mass spectrum (ESI, [M+H]$^+$) m/z 342. $^1$HNMR (400 MHz, DMSO-d$_6$): δ 7.73 (s, 1H), 7.55 (s, 1H), 7.44 (d, 1H, J=8.71 Hz), 7.30 (d, 2H, J=7.96 Hz), 7.19 (d, 1H, J=8.71 Hz), 7.10 (d, 2H, J=7.63 Hz), 6.46 (s, 1H), 5.36 (s, 2H), and 1.21 ppm (s, 9H).

Elemental Analysis for $C_{19}H_{20}BrN$: Calculated: C, 66.67; H, 5.89; N, 4.09. Found: C, 66.78; H, 5.86; N, 4.02.

Step 2

1-[4-(tert-Butyl)benzyl]-5-(3-methylphenyl)-1H-indole

The mixture of 5-bromo-1-(4-tert-butylbenzyl)-1H-indole (67.5 g, 197.2 mmol), 3-methylbenzeneboronic acid (27.6 g, 197.2 mmol), potassium carbonate (27.2 g, 493 mmol), palladium(II) acetate (0.338 g) and tetrabutylammonium bromide (63.5 g, 197.2 mmol) in 10% dioxane in water (degassed, 1.72 L) was stirred at 70° C. The reaction was monitored by TLC. 3-Methylbenzeneboronic acid (45.2 g, 394.4 mmol) was added in four portions every 10 hours, after which time 5-bromo-1-(4-tert-butylbenzyl)-1H-indole was no longer detected by TLC. The reaction was cooled to room temperature and the solvent was decanted. The dark gum-like oil was washed with water and extracted with petroleum ether (4×2 L). The combined petroleum ether extracts were washed with water and filtered. This mixture was concentrated to a volume of about 1.5 L and allowed to crystallize. The solid was isolated by filtration and dried under vacuum at 60° C. for 10 hours. to afford the title compound as a white solid (50.8 g, 73%), mp: 94–95° C. Mass spectrum (ESI, [M+H]$^+$) m/z 354. $^1$ HNMR (400 MHz, DMSO-d$_6$): δ 7.79 (s, 1H), 7.53–7.51 (m, 2H), 7.45 (s, 1H), 7.41 (d, 1H, J=7.79 Hz), 7.37 (d, 2H, J =8.55 Hz), 7.32–7.28 (m, 3H), 7.14 (d, 2H, J=8.40 Hz), 7.09 (d, 1H, J=8.40 Hz), 6.51 (d, 1H, J=2.75 Hz), 5.38 (s, 2H), 2.36 (s, 3H), and 1.21 ppm (s, 9H).

Elemental Analysis for $C_{26}H_{27}N$: Calculated: C, 88.34; H, 7.70; N, 3.96. Found: C, 88.24; H, 7.64; N, 3.92.

Step 3

[1-(4-tert-Butylbenzyl)-5-(3-methylphenyl)-1H-indol-3-yl](oxo)acetic acid

The title compound was prepared from 1-[4-(tert-butyl)benzyl]-5-(3-methylphenyl)-1H-indole (44.6 g, 126.2 mmol) and oxalyl chloride (22.0 mL, 252.4 mmol) in substantially the same manner, as described in Step 3 of Example 25. The product was obtained as a yellow solid (51.4 g, 96%), mp: 128–129° C. Mass spectrum (ESI, [M–H]$^-$) m/z 424. $^1$HNMR (400 MHz, DMSO-d$_6$): δ 13.50 (br s, 1H), 8.70 (s, 1H), 8.40 (s, 1H), 7.69 (d, 1H, J=8.71 Hz), 7.56 (d, 1H, J=8.55 Hz), 7.45–7.42 (m, 2H), 7.37–7.33 (m, 3H), 7.24 (d, 2H, J=8.40 Hz), 7.16 (d, 1H, J=7.49 Hz), 5.57 (s, 2H), 2.38 (s, 3H), and 1.22 ppm (s, 9H).

Elemental Analysis for $C_{28}H_{27}NO_3$: Calculated: C, 79.03; H, 6.40; N, 3.29. Found: C, 78.77; H, 6.29; N, 3.25.

EXAMPLE 35

[1-(4-tert-Butylbenzyl)-5-(3-methoxyphenyl)-1H-indol-3-yl](oxo)acetic acid

Step 1

1-[4-(tert-Butyl)benzyl]-5-(3-methoxyphenyl)-1H-indole

The title compound was prepared from 5-bromo-1-[4-(tert-butyl)benzyl]-1H-indole (Step 1 of Example 34) and 3-methoxyphenylboronic acid in substantially the same manner, as described in Step 2 of Example 25. The product was obtained as an oil. Mass spectrum (ESI, [M+H]$^+$) m/z 370. $^1$HNMR (400 MHz, DMSO-d$_6$): δ 7.81 (s, 1H), 7.53 (s, 1H), 7.51 (d, 1H, J=8.55 Hz), 7.39 (d, 1H, J=8.55 Hz), 7.34–7.30 (m, 3H), 7.20 (d, 1H, J=7.64 Hz), 7.15–7.13 (m, 3H), 6.85 (d, 1H, J=8.25 Hz), 6.52 (d, 1H, J=3.05 Hz), 5.39 (s, 2H), 5.81 (s, 3H), and 1.21 ppm (s, 9H).

Elemental Analysis for $C_{26}H_{27}NO$: Calculated: C, 84.51; H, 7.37; N, 3.79. Found: C, 83.30; H, 7.42; N, 3.74.

Step 2

[1-(4-tert-Butylbenzyl)-5-(3-methoxyphenyl)-1H-indol-3-yl](oxo)acetic acid

The title compound was prepared from 1-[4-(tert-butyl)benzyl]-5-(3-methoxyphenyl)-1H-indole and oxalyl chloride in substantially the same manner, as described in Step 3 of Example 25. The product was obtained as a yellow solid, mp: 86–87° C. Mass spectrum (ESI, [M+H]$^+$) m/z 442. $^1$HNMR (400 MHz, DMSO-d$_6$): δ 13.50 (br s, 1H), 8.71 (s, 1H), 8.40 (s, 1H), 7.69 (d, 1H, J=8.55 Hz), 7.58 (d, 1H, J=8.55 Hz), 7.40–7.35 (m, 3H), 7.24 (d, 2H, J=8.40 Hz), 7.20 (d, 1H, J=7.64 Hz), 7.14 (s, 1H), 6.93 (d, 1H, J=8.25 Hz), 5.57 (s, 2H), 3.82 (s, 3H), and 1.22 ppm (s, 9H).

Elemental Analysis for $C_{28}H_{27}NO_4 \cdot 0.1 H_2O$: Calculated: C, 75.86; H, 6.18; N, 3.16. Found: C, 75.84; H, 5.91; N, 2.98.

EXAMPLE 36

[1-(4-tert-Butylbenzyl)-5-(4-tert-butylphenyl)-1H-indol-3-yl](oxo)acetic acid

Step 1

1-[4-(tert-Butyl)benzyl]-5-[4-(tert-butyl)phenyl]-1H-indole

The title compound was prepared from 5-bromo-1-[4-(tert-butyl)benzyl]-1H-indole (Step 1 of Example 34) and 4-(tert-butyl)phenylboronic acid in substantially the same manner, as described in Step 2 of Example 25. The product was obtained as an off-white solid, mp: 167–168° C. Mass spectrum (ESI, [M+H]$^+$) m/z 396. $^1$ HNMR (400 MHz, DMSO-d$_6$): δ 7.77 (d, 1H, J=1.38 Hz), 7.55 (d, 2H, J=8.56 Hz), 7.52–7.51 (m, 2H), 7.43 (d, 1H, J=8.40 Hz), 7.36 (d, 1H, J=8.55 Hz), 7.31 (d, 2H, J=8.40 Hz), 7.14 (d, 2H, J=8.40 Hz), 6.51 (d, 1H, J=3.05 Hz), 5.38 (s, 2H), 1.30 (s, 9H), and 1.21 ppm (s, 9H).

Elemental Analysis for $C_{29}H_{33}N \cdot 0.3 H_2O$: Calculated: C, 86.87; H, 8.46; N, 3.49. Found: C, 87.08; H, 8.51; N, 3.46.

Step 2

[1-(4-tert-Butylbenzyl)-5-(4-tert-butylphenyl)-1H-indol-3-yl](oxo)acetic acid

The title compound was prepared from 1-[4-(tert-butyl)benzyl]-5-[4-(tert-butyl)phenyl]-1H-indole and oxalyl chloride in substantially the same manner, as described in Step 3 of Example 25. The product was obtained as a light brown solid, mp: 111–112° C. Mass spectrum (ESI, [M+H]$^+$) m/z 468. $^1$HNMR (400 MHz, DMSO-d$_6$): δ 13.50 (br s, 1H), 8.70 (s, 1H), 8.40 (s, 1H), 7.68 (d, 1H, J=8.55 Hz), 7.58–7.54 (m, 3H), 7.48 (d, 2H, J=8.40 Hz), 7.36 (d, 2H, J=8.25 Hz), 7.25 (d, 2H, J=8.40 Hz), 5.56 (s, 2H), 1.31 (s, 9H), and 1.22 ppm (s, 9H).

Elemental Analysis for $C_{31}H_{33}NO_3 \cdot 0.2 H_2O$: Calculated: C, 79.02; H, 7.14; N, 2.97. Found: C, 78.97; H, 7.22; N, 2.90.

EXAMPLE 37

[1-(4-tert-Butylbenzyl)-5-(3-chlorophenyl)-1H-indol-3-yl](oxo)acetic acid

Step 1

1-[4-(tert-Butyl)benzyl]-5-(3-chlorophenyl)-1H-indole

The title compound was prepared from 5-bromo-1-[4-(tert-butyl)benzyl]-1H-indole (Step 1 of Example 34) and 3-chlorophenylboronic acid in substantially the same manner, as described in Step 2 of Example 25. The product was obtained as an oil. Mass spectrum (ESI, [M+H]$^+$) m/z 374. $^1$HNMR (400 MHz, DMSO-d$_6$): δ 7.86 (d, 1H, J=1.53 Hz), 7.68 (dd, 1H, J=1.84 and 1.83 Hz), 7.61 (d, 1H, J=7.79 Hz), 7.43 (d, 1H, J=8.40 Hz), 7.36 (d, 1H, J=8.55 Hz), 7.55–7.54 (m, 2H), 7.46–7.41 (m, 2H), 7.34 (d, 1H, J=1.07 Hz), 7.31 (d, 2H, J=8.40 Hz), 7.13 (d, 2H, J=8.40 Hz), 6.53 (d, 1H, J=3.06 Hz), 5.40 (s, 2H), 1.30 (s, 9H), and 1.21 ppm (s, 9H).

Elemental Analysis for $C_{26}H_{27}NO$: Calculated: C, 84.51; H, 7.37; N, 3.79. Found: C, 85.08; H, 7.35; N, 3.66.

Step 2

[1-(4-tert-Butylbenzyl)-5-(3-chlorophenyl)-1H-indol-3-yl](oxo)acetic acid

The title compound was prepared from 1-[4-(tert-butyl)benzyl]-5-(3-chlorophenyl)-1H-indole and oxalyl chloride in substantially the same manner, as described in Step 3 of Example 25. The product was obtained as a light brown solid, mp: 138–139° C. Mass spectrum (ESI, [M+H]$^+$) m/z 446. $^1$HNMR (400 MHz, DMSO-d$_6$): δ 13.50 (br s, 1H), 8.73 (s, 1H), 8.42 (s, 1H), 7.72 (d, 1H, J=8.71 Hz), 7.67 (dd, 1H, J=1.83 Hz and 1.83 Hz), 7.63–7.60 (m, 2H), 7.50 (dd, 1H, J=7.94 Hz and 7.79 Hz), 7.41 (d, 1H, J=7.95 Hz), 7.35 (d, 2H, J=8.40 Hz), 7.24 (d, 2H, J=8.40 Hz), 5.56 (s, 2H), and 1.22 ppm (s, 9H).

Elemental Analysis for $C_{27}H_{24}ClNO_3$: Calculated: C, 72.72; H, 5.42; N, 3.14. Found: C, 72.43; H, 5.39; N, 3.07.

EXAMPLE 38

[1-(4-tert-Butylbenzyl)-5-(4-chlorophenyl)-1H-indol-3-yl](oxo)acetic acid

Step 1

1-[4-(tert-Butyl)benzyl]-5-(4-chlorophenyl)-1H-indole

The title compound was prepared from 5-bromo-1-[4-(tert-butyl)benzyl]-1H-indole (Step 1 of Example 34) and 4-chlorophenylboronic acid in substantially the same manner, as described in Step 2 of Example 25. The product was obtained as an oil. Mass spectrum (ESI, [M+H]$^+$) m/z 374. $^1$HNMR (400 MHz, DMSO-d$_6$): δ 7.82 (d, 1H, J=1.52 Hz), 7.66 (d, 2H, J=8.55 Hz), 7.55–7.53 (m, 2H), 7.46 (d, 2H, J=8.55 Hz), 7.39 (d, 1H, J=8.56 Hz), 7.31 (d, 2H, J=8.40 Hz), 7.13 (d, 2H, J=8.24 Hz), 6.53 (d, 1H, J=3.05 Hz), 5.39 (s, 2H), and 1.21 ppm (s, 9H).

Elemental Analysis for C$_{25}$H$_{24}$ClN: Calculated: C, 78.05; H, 6.60; N, 3.64. Found: C, 78.02; H, 6.27; N, 3.53.

Step 2

[1-(4-tert-Butylbenzyl)-5-(4-chlorophenyl)-1H-indol-3-yl](oxo)acetic acid

The title compound was prepared from 1-[4-(tert-butyl)benzyl]-5-(4-chlorophenyl)-1H-indole and oxalyl chloride in substantially the same manner, as described in Step 3 of Example 25. The product was obtained as a light brown solid, mp: 183–184° C. Mass spectrum (ESI, [M+H]$^+$) m/z 446. $^1$HNMR (400 MHz, DMSO-d$_6$): δ 13.50 (br s, 1H), 8.72 (s, 1H), 8.42 (s, 1H), 7.71 (d, 1H, J=8.55 Hz), 7.67 (d, 2H, J=8.70 Hz), 7.59 (d, 2H, J=8.70 Hz), 7.51 (d, 2H, J=8.55 Hz), 7.35 (d, 2H, J=8.24 Hz), 7.24 (d, 2H, J=8.40 Hz), 5.57 (s, 2H), and 1.22 ppm (s, 9H).

Elemental Analysis for C$_{27}$H$_{24}$ClNO$_3$: Calculated: C, 72.72; H, 5.42; N, 3.14. Found: C, 72.40; H, 5.43; N, 3.04.

EXAMPLE 39

[1-(4-tert-Butylbenzyl)-5-(2-methylphenyl)-1H-indol-3-yl](oxo)acetic acid

Step 1

1-[4-(tert-Butyl)benzyl]-5-(2-methylphenyl)-1H-indole

The title compound was prepared from 5-bromo-1-[4-(tert-butyl)benzyl]-1H-indole (Step 1 of Example 34) and 2-methylphenylboronic acid in substantially the same manner, as described in Step 2 of Example 25. The product was obtained as a brown oil. Mass spectrum (ESI, [M+H]$^+$) m/z 354. $^1$HNMR (400 MHz, DMSO-d$_6$): δ 7.53 (d, 1H, J=3.06 Hz), 7.50 (d, 1H, J=8.55 Hz), 7.46 (d, 1H, J=0.95 Hz), 7.33 (d, 2H, J=7.96 Hz), 7.26–7.18 (m, 5H), 7.05 (d, 1H, J=8.40 Hz), 6.48 (d, 1H, J=3.06 Hz), 5.38 (s, 2H), 2.22 (s, 3H), and 1.22 ppm (s, 9H).

Elemental Analysis for C$_{26}$H$_{27}$N: Calculated: C, 88.34; H, 7.70; N, 3.96. Found: C, 88.28; H, 7.58; N, 3.75.

Step 2

[1-(4-tert-Butylbenzyl)-5-(2-methylphenyl)-1H-indol-3-yl](oxo)acetic acid

The title compound was prepared from 1-[4-(tert-butyl)benzyl]-5-(2-methylphenyl)-1H-indole and oxalyl chloride in substantially the same manner, as described in Step 3 of Example 25. The product was obtained as a light brown solid, mp: 97–98° C. Mass spectrum (ESI, [M+H]$^+$) m/z 426. $^1$HNMR (400 MHz, DMSO-d$_6$): δ 13.59 (br s, 1H), 8.71 (s, 1H), 8.10 (s, 1H), 7.68 (d, 1H, J=8.55 Hz), 7.37 (d, 2H, J=8.25 Hz), 7.30–7.20 (m, 7H), 5.57 (s, 2H), 2.20 (s, 3H), and 1.23 ppm (s, 9H).

Elemental Analysis for C$_{28}$H$_{27}$NO$_3$: Calculated: C, 79.03; H, 6.40; N, 3.29. Found: C, 78.70; H, 6.42; N, 3.28.

EXAMPLE 40

{1-(2-Ethylbutyl)-5-[4-(trifluoromethoxy)phenyl]-1H-indol-3-yl}(oxo)acetic acid

Step 1

5-Bromo-1-(2-ethylbutyl)-1H-indole

The title compound was prepared from 1-bromo-2-ethylbutane (14.14 mL, 101 mmol) and 5-bromoindole (20 g, 101 mmol) in substantially the same manner, as described in Step 1 of Example 25. The product (17.78 g, 62%) was obtained as a colorless oil. Mass spectrum (ESI, [M+H]$^+$) m/z 280. $^1$ HNMR (400 MHz, DMSO-d$_6$): δ 7.71 (d, 1H, J=1.83 Hz), 7.43–7.39 (m, 2H), 7.21 (dd, 2H, J=8.72 and 1.99 Hz), 6.41 (d, 1H, J=2.90 Hz), 4.04 (d, 2H, J=7.48 Hz), 1.76 (hep, 1H), 1.21 (p, 4H), and 0.82 ppm (t, 6H).

Elemental Analysis for C$_{14}$H$_{18}$BrN: Calculated: C, 60.01; H, 6.47; N, 5.00. Found: C, 60.20; H, 6.46; N, 4.96.

Step 2

1-(2-Ethylbutyl)-5-[4-(trifluoromethoxy)phenyl]-1H-indole

The title compound was prepared from 5-bromo-1-(2-ethylbutyl)-1H-indole and 4-(trifluoromethoxy)phenylboronic acid in substantially the same manner, as described in Step 2 of Example 25. The product was obtained as an oil. Mass spectrum (APCI, [M+H]$^+$) m/z 362. $^1$HNMR (300 MHz, DMSO-d$_6$): δ 7.82 (s, 1H), 7.77 (d, 2H, J=8.56 Hz), 7.51 (d, 1H, J=8.50 Hz), 7.44–7.39 (m, 4H), 6.49 (d, 1H, J=3.12 Hz), 4.07 (d, 2H, J=7.32 Hz), 1.80 (hep, 1H), 1.24 (p, 4H), and 0.85 ppm (t, 6H).

Elemental Analysis for C$_{21}$H$_{22}$F$_3$NO: Calculated: C, 69.79; H, 6.14; N, 3.88. Found: C, 69.79; H, 5.85; N, 3.82.

Step 3

{1-(2-Ethylbutyl)-5-[4-(trifluoromethoxy)phenyl]-1H-indol-3-yl}(oxo)acetic acid

The title compound was prepared from 1-(2-ethylbutyl)-5-[4-(trifluoromethoxy)phenyl]-1H-indole and oxalyl chloride in substantially the same manner, as described in Step 3 of Example 25. The product was obtained as a light brown solid, mp: 98–99° C. Mass spectrum (ESI, [M+H]$^+$) m/z 434. $^1$HNMR (400 MHz, DMSO-d$_6$): δ 13.59 (br s, 1H), 8.51 (s, 1H), 8.43 (s, 1H), 7.79 (d, 2H, J=8.7 Hz), 7.74 (d, 1H, J=8.55 Hz), 7.64 (d, 1H, J=7.82 Hz), 7.63 (d, 2H, J=7.80 Hz), 7.47 (d, 2H, J=8.24 Hz), 4.26 (d, 2H, J=7.49 Hz), 1.86 (hep, 1H), 1.27 (p, 4H), and 0.86 ppm (t, 6H).

Elemental Analysis for C$_{23}$H$_{22}$F$_3$NO$_4$: Calculated: C, 69.79; H, 6.14; N, 3.88. Found: C, 69.79; H, 5.85; N, 3.82.

EXAMPLE 41

{2-[(Acetyloxy)methyl]-1-(4-methylbenzyl)-5-[4-(trifluoromethoxy)phenyl]-1H-indol-3-yl}(oxo) acetic acid Step 1

Ethyl 5-bromo-1-(4-methylbenzyl)-1H-indole-2-carboxylate

The title compound was prepared from ethyl 5-bromo-1H-indole-2-carboxylate and 4-methylbenzyl bromide in substantially the same manner, as described in Step 1 of Example 25. The product was obtained as a semi-solid contained 0.8 mole equivalent DMF. Mass spectrum (ESI, [M+H]$^+$) m/z 372. $^1$H NMR (400 MHz, DMSO-d$_6$) δ 7.93 (d, 1H, J=7.94 Hz), 7.55 (d, 1H, J=9.01 Hz), 7.40 (dd, 1H, J=8.85 and 1.98 Hz), 7.32 (s, 1H), 7.04 (d, 2H, J=7.96 Hz), 6.90 (d, 2H, J=7.94 Hz), 5.79 (s, 2H), 4.28 (q, 2H), 2.20 (s, 3H), and 1.28 ppm (t, 3H).

Step 2

Ethyl 1-(4-methylbenzyl)-5-[4-(trifluoromethoxy)phenyl]-1H-indole-2-carboxylate

The title compound was prepared from ethyl 5-bromo-1-(4-methylbenzyl)-1H-indole-2-carboxylate and 4-(trifluoromethoxy)phenylboronic acid in substantially the same manner, as described in Step 2 of Example 25. The product was obtained as an off-white solid, m.p. 77–78° C. Mass spectrum (ESI, [M+H]$^+$) m/z 454. $^1$H NMR (400 MHz, DMSO-d$_6$) δ 8.00 (s, 1H), 7.78 (d, 2H, J=8.70 Hz), 7.67 (d, 1H, J=8.85 Hz), 7.61 (dd, 1H, J=8.70 and 1.68 Hz), 7.44 (s, 1H), 7.42–7.41 (m, 3H), 7.06 (d, 2H, J=7.94 Hz), 6.94 (d, 2H, J=8.09 Hz), 5.83 (s, 2H), 4.29 (q, 2H), 2.21 (s, 3H), and 1.30 ppm (t, 3H).

Elemental Analysis for $C_{26}H_{22}F_3NO_3$: Calculated: C, 68.87; H, 4.89; N, 3.09. Found: C, 69.00; H, 4.66; N, 3.06.

Step 3

{1-(4-Methylbenzyl)-5-[4-(trifluoromethoxy)phenyl]-1H-indol-2-yl}methanol

Lithium aluminum hydride (0.244 g, 6.1 mmol) was added portionwise to a stirring solution of ethyl 1-(4-methylbenzyl)-5-[4-(trifluoromethoxy)phenyl]-1H-indole-2-carboxylate (2.0 g, 4.4 mmol) in ethyl ether (17 mL) at 0° C. under a nitrogen atmosphere over a period of 5 minutes. The mixture was then warmed up to room temperature. After the reaction mixture was stirred at room temperature for 5 hour, the reaction was carefully quenched with water then filtered. The filtrate was extracted with ethyl acetate. The organic extract was washed with water and brine, dried over anhydrous magnesium sulfate and evaporated to afford the title compound as a white solid (1.56 g, 86%). Mass spectrum (ESI, [M+H]$^+$) m/z 412. $^1$HNMR (400 MHz, DMSO-$d_6$): δ 7.81 (s, 1H), 7.76 (d, 2H, J=6.71 Hz), 7.45–7.35 (m, 4H), 7.08 (d, 2H, J=7.74 Hz), 6.96 (d, 2H, J=8.09 Hz), 6.50 (s, 1H), 5.44 (s, 2H), 5.35 (t, 1H), 4.60 (d, 2H), and 2.23 ppm (t, 3H).

Elemental Analysis for $C_{24}H_{20}F_3NO_2$: Calculated: C, 70.07; H, 4.90; N, 3.40. Found: C, 69.80; H, 4.75; N, 3.34.

Step 4

{1-(4-Methylbenzyl)-5-[4-(trifluoromethoxy)phenyl]-1H-indol-2-yl}methyl acetate

Acetyl chloride (0.222 mL, 3.08 mmol) was added to a stirring solution of {1-(4-methylbenzyl)-5-[4-(trifluoromethoxy)phenyl]-1H-indol-2-yl}methanol (0.507 g, 1.23 mmol) and N,N-diisopropylethylamine (0.547 mL, 3.08 mmol) in methylene chloride (8 mL) at 0° C. under a nitrogen atmosphere over a period of 5 minutes. After the reaction mixture was stirred at room temperature overnight, the reaction quenched carefully with water. The aqueous mixture was extracted with ethyl acetate. The organic extract was washed with water and brine, dried over anhydrous magnesium sulfate and evaporated to afford the title compound as a solid (0.557 g, 99.6%), mp: 125–126° C. Mass spectrum (ESI, [M+H]$^+$) m/z 454. $^1$HNMR (400 MHz, DMSO-$d_6$): δ 7.86 (s, 1H), 8.77 (d, 2H, J=8.96 Hz), 7.48–7.40 (m, 4H), 7.09 (d, 2H, J=7.94 Hz), 6.90 (d, 2H, J=7.94 Hz), 6.70 (s, 1H), 5.44 (s, 2H), 5.23 (s, 2H), 2.23 (s, 3H), and 1.85 ppm (s, 3H).

Elemental Analysis for $C_{26}H_{22}F_3NO_3$: Calculated: C, 68.32; H, 4.94; N, 3.07. Found: C, 67.96; H, 4.57; N, 2.96.

Step 5

{2-[(Acetyloxy)methyl]-1-(4-methylbenzyl)-5-[4-(trifluoromethoxy)phenyl]-1H-indol-3-yl}(oxo)acetic acid The title compound was prepared from {1-(4-methylbenzyl)-5-[4-(trifluoromethoxy)phenyl]-1H-indol-2-yl}methyl acetate and oxalyl chloride in substantially the same manner, as described in Step 3 of Example 25. The product was obtained as a light brown solid, mp: 79–80° C. Mass spectrum (ESI, [M–H]$^-$) m/z 524. $^1$HNMR (400 MHz, DMSO-$d_6$): δ 14.50 (br s, 1H), 8.20 (s, 1H), 7.74 (d, 2H, J=8.55 Hz), 7.70 (d, 1H, J=8.69 Hz), 7.62 (d, 1H, J=8.55 Hz), 7.47 (d, 2H, J=8.25 Hz), 7.15 (d, 2H, J=7.88 Hz), 6.99 (d, 2H, J=7.78 Hz), 5.64 (s, 2H), 5.53 (s, 2H), 2.25 (s, 3H), and 1.83 ppm (s, 3H).

Elemental Analysis for $C_{28}H_{22}F_3NO_6$: Calculated: C, 64.00; H, 2.67; N, 2.67. Found: C, 63.77; H, 3.99; N, 2.65.

EXAMPLE 42

{2-(Hydroxymethyl)-1-(4-methylbenzyl)-5-[4-(trifluoromethoxy)phenyl]-1H-indol-3-yl}(oxo)acetic acid, potassium salt A solution of {2-[(acetyloxy)methyl]-1-(4-methylbenzyl)-5-[4-(trifluoromethoxy)phenyl]-1H-indol-3-yl}(oxo)acetic acid (0.50 g, 0.96 mmol) (Step 5 of Example 41) and aqueous potassium hydroxide (1.0 N, 2.38 mL, 2.38 mmol) in THF : water (1:1, 16 mL) was stirred at room temperature for 4 hours. The reaction mixture was evaporated to dryness. The residual solid was stirred in water: hexane (8:92, 100 mL) and filtered to give the title compound as a white solid (0.4 g), mp: 248–249.5° C. Mass spectrum (ESI, [M–H]$^-$) m/z 482. $^1$HNMR (400 MHz, DMSO-$d_6$): δ 8.51 (s, 1H), 7.73 (d, 2H, J=8.86 Hz), 7.50 (d, 1H, J=8.56 Hz), 7.45 (d, 1H, J=8.55 Hz), 7.43 (d, 2H, J=7.94 Hz), 7.09 (d, 2H, J=8.09 Hz), 7.05 (d, 2H, J=8.09 Hz), 5.74 (t, 1H), 5.55 (s, 2H), 4.80 (d, 2H, J=6.80 Hz), and 2.23 ppm (s, 3H).

Elemental Analysis for $C_{26}H_{20}F_3NO_5 \cdot 1.0K \cdot 0.8H_2O$: Calculated: C, 58.27; H, 3.87; N, 2.61. Found: C, 58.14; H, 3.82; N, 2.59.

EXAMPLE 43

{2-[(Acetyloxy)methyl]-1-benzyl-5-[4-(trifluoromethoxy)phenyl]-1H-indol-3-yl}(oxo)acetic acid Step 1

Ethyl 5-bromo-1-benzyl-1H-indole-2-carboxylate

The title compound was prepared from ethyl 5-bromo-1H-indole-2-carboxylate and benzyl bromide in substantially the same manner, as described in Step 1 of Example 25. The product was obtained as a light yellow solid. Mass spectrum (ESI, [M+H]$^+$) m/z 358.1 HNMR (300 MHz, DMSO-$d_6$): δ 7.94 (s, 1H), 7.55 (d, 1H, J=9.01 Hz), 7.42 (d, 1H, J=8.85 Hz), 7.34 (s, 1H), 7.30–7.21 (m, 3H), 6.99 (d, 2H, J=7.94 Hz), 5.85 (s, 2H), 4.28 (q, 2H), and 1.28 ppm (t, 3H).

Elemental Analysis for $C_{18}H_{16}BrNO_2$: Calculated: C, 60.35; H, 4.50; N, 3.91. Found: C, 69.19; H, 4.51; N, 3.75.

Step 2

Ethyl 1-benzyl-5-[4-(trifluoromethoxy)phenyl]-1H-indole-2-carboxylate

The title compound was prepared from ethyl 5-bromo-1-benzyl-1H-indole-2-carboxylate and 4-(trifluoromethoxy)phenylboronic acid in substantially the same manner, as described in Step 2 of Example 25. The product was obtained as an oil. Mass spectrum (ESI, [M+H]$^+$) m/z 440. $^1$HNMR (400 MHz, DMSO-$d_6$): δ 8.01 (s, 1H), 7.79 (d, 2H, J=8.86 Hz), 7.67 (d, 1H, J=8.85 Hz), 7.62 (dd, 1H, J=8.70 and 1.68 Hz), 7.44–7.42 (m, 2H), 7.28–7.20 (m, 3H), 7.04 (d, 2H, J=7.94 Hz), 5.88 (s, 2H), 4.28 (q, 2H), and 1.29 ppm (t, 3H).

Step 3

{1-benzyl-5-[4-(trifluoromethoxy)phenyl]-1H-indol-2-yl}methanol

The title compound was prepared from Ethyl 1-benzyl-5-[4-(trifluoromethoxy)phenyl]-1H-indole-2-carboxylate (Step 2 of Example 25) and lithium aluminum hydride in substantially the same manner, as described in Step 1 of Example 21. The product was obtained as a white solid, mp: 108–109° C. Mass spectrum (ESI, [M+H]$^+$) m/z 398. $^1$HNMR (400 MHz, DMSO-$d_6$): δ 7.82 (s, 1H), 7.76 (d, 2H, J=8.86 Hz), 7.42–7.36 (m, 4H), 7.29 (d, 1H, J=7.03 Hz), 7.27 (d, 1H, J=7.63 Hz), 7.23–7.20 (m, 1H), 7.06 (d, 2H, J=7.03 Hz), 6.52 (s, 1H), 5.50 (s, 2H), 5.36 (t, 1H), and 4.60 ppm (d, 2H).

Elemental Analysis for $C_{23}H_{18}F_3NO_2$: Calculated: C, 69.52; H, 4.57; N, 3.52. Found: C, 69.21; H, 4.38; N, 3.40.

Step 4

{1-benzyl-5-[4-(trifluoromethoxy)phenyl]-1H-indol-2-yl}methyl acetate

The title compound was prepared from ethyl {1-benzyl-5-[4-(trifluoromethoxy)phenyl]-1H-indole-2-yl}methanol in substantially the same manner, as described in Step 2 of Example 42. The product was obtained as an oil. Mass spectrum (ESI, [M+H]$^+$) m/z 440. $^1$HNMR (300 MHz, DMSO-d$_6$): δ 7.88 (s, 1H), 7.77 (d, 2H, J=8.87 Hz), 7.48–7.40 (m, 4H), 7.29–7.22 (d, 3H), 7.00 (d, 2H, J=7.01 Hz), 6.72 (s, 1H), 5.50 (s, 2H), 5.24 (s, 2H), and 1.80 ppm (s, 3H).

Elemental Analysis for $C_{25}H_{20}F_3NO_3$: Calculated: C, 68.33; H, 4.59; N, 3.19. Found: C, 68.18; H, 4.70; N, 3.06.

Step 5

{2-[(Acetyloxy)methyl]-1-benzyl-5-[4-(trifluoromethoxy)phenyl]-1H-indol-3-yl}(oxo)acetic acid The title compound was prepared from {1-benzyl-5-[4-(trifluoromethoxy)phenyl]-1H-indol-2-yl}methyl acetate and oxalyl chloride in substantially the same manner, as described in Step 3 of Example 25. The product was obtained as a brown solid, mp: 85–86° C. Mass spectrum (ESI, [M–H]$^-$) m/z 510. $^1$HNMR (400 MHz, DMSO-d$_6$): δ 14.40 (br s, 1H), 8.20 (s, 1H), 7.76 (d, 2H, J=6.72 Hz), 7.72 (d, 1H, J=8.70 Hz), 7.63 (d, 1H, J=8.70 Hz), 7.48 (d, 2H, J=8.24 Hz), 7.34–7.25 (m, 3H), 7.08 (d, 1H, J=7.23 Hz), 5.70 (s, 2H), 5.53 (s, 2H), and 1.78 ppm (s, 3H).

Elemental Analysis for $C_{27}H_{20}F_3NO_6$: Calculated: C, 63.41; H, 3.94; N, 2.74. Found: C, 63.02; H, 3.97; N, 2.64.

EXAMPLE 44

{1-Benzyl-2-(hydroxymethyl)-5-[4-(trifluoromethoxy)phenyl]-1H-indol-3-yl}(oxo)acetic acid, potassium salt The title compound was prepared from {2-[(acetyloxy)methyl]-1-benzyl-5-[4-(trifluoromethoxy)phenyl]-1H-indol-3-yl}(oxo)acetic acid (Step 5 of Example 43) and aqueous potassium hydroxide in substantially the same manner, as described in Example 42. The product was obtained as a white solid, mp: 280–282° C. Mass spectrum (ESI, [M–H]$^-$) m/z 468. $^1$HNMR (400 MHz, DMSO-d$_6$): δ 8.51 (s, 1H), 7.72 (d, 2H, J=8.70 Hz), 7.52 (d, 1H, J=8.55 Hz), 7.47–7.43 (m, 3H), 7.31–28 (m, 2H), 7.23 (d, 1H, J=7.18 Hz), 7.15 (d, 2H, J=7.18 Hz), 5.75 (t, 1H), 5.62 (s, 2H), and 4.81 ppm (d, 2H, J=6.72 Hz).

Elemental Analysis for $C_{25}H_{18}F_3NO_5 \cdot 1.0K \cdot 1.0 H_2O$: Calculated: C, 57.14; H, 3.64; N, 2.67. Found: C, 57.05; H, 3.42; N, 2.55.

EXAMPLE 45

[5-(3-Chlorophenyl)-1-cyclopentyl-1H-indol-3-yl]-oxo-acetic acid

Step 1

5-(3-Chlorophenyl)indole

A stirred slurry of 4.23 g (40 mmol) Na$_2$CO$_3$, 1.84 g (9.4 mmol) 5-bromoindole, 1.88 g (10 mmol) 3-chlorophenylboronic acid, and 0.29 g (0.25 mmol) Pd(PPh$_3$)$_4$ in 50 mL 1:1 EtOH-water was heated to reflux for 2.5 hours. The reaction mixture was allowed to cool and was then poured into 400 mL water and extracted with EtOAc. The organic layer was separated, dried over MgSO$_4$, and concentrated to afford 2.15 g crude 5-(3-chlorophenyl) indole as a tan solid.

Step 2

1-Benzenesulfonyl-5-(3-chlorophenyl)-1H-indole

To a stirred slurry of 0.61 g (12.7 mmol), 50% dispersion of NaH in mineral oil, in 36 mL anhydrous THF was added 2.15 g crude 5-(3-chlorophenyl)indole (Step 1 of Example 45). The solution was allowed to stir at room temperature 15 min upon which time 1.2 mL (9.4 mmol) phenylsulfonyl chloride was added dropwise. The solution was allowed to stir at room temperature overnight and was poured into water and extracted with EtOAc. The organic phase was dried over MgSO$_4$ and concentrated. The crude product was chromatographed on SiO$_2$ using 10–25% EtOAc-Hex to afford 1.46 g 1-benzenesulfonyl-5-(3-chlorophenyl)-1H-indole as a tan solid.

Step 3

5-(3-Chlorophenyl)-1-cyclopentyl-1H-indole

A 5 mL conical glass microwave reaction vessel with stir bar, sealed with a septum and swept with nitrogen, was charged with a solution of 0.08 g (0.22 mmol) 1-(benzenesulfonyl-5-(3-chlorophenyl)-1H-indole in 1.2 mL anhydrous toluene. 32 μL (0.33 mmol) cyclopentanol was added with stirring, followed by 0.3 mL 1.0 M solution of KOt-Bu in THF. The septum was removed and the vial was sealed with a cap. The reaction vessel was heated to 150° C. for 350 seconds in a microwave reactor (Personal Chemistry Inc., Milford, Mass.) and allowed to cool to room temperature. An aliquot removed for LC analysis indicated that the reaction was complete. The crude reaction mixture was taken up in 10 mL of brine and extracted with EtOAc. The organic phase was filtered through an 8 mL aqueous/organic separation column (Alltech Associates, Inc., Deerfield, Ill.) and was concentrated. The residue was purified by RP-HPLC (see Note 1 below) to give 11.2 mg 5-(3-chlorophenyl)-1-cyclopentyl-1H-indole as an oil.

Step 4

[5-(3-Chlorophenyl)-1-cyclopentyl-1H-indol-3-yl]-oxo-acetic acid

The product from Step 3 of Example 45 was dissolved in 0.5 ml anhydrous THF and 50 μL (COCl)$_2$ was added. The solution was mixed at room temperature overnight with orbital shaking. An aliquot removed for LC analysis indicated that the reaction was complete. The solution was added to 1 mL aqueous NaHCO$_3$ and the vial was capped and shaken. 0.1 mL 2N HCl was added and the vial was again capped and shaken. The reaction was concentrated to dryness under vacuum. The residue was purified by RP-HPLC (see Note 1 below) to give 6.4 mg of the title compound as an oil.

LCMS Data (see Note 2 below):

Molecular ion and retention time:

366 (M–H); 2.98 min.

Note 1: Semi-preparative RP-HPLC Conditions:

Gilson Semi-Preparative HPLC system with Unipoint Software

Column: Phenomenex C18 Luna 21.6 mm×60 mm, 5 μM;

Solvent A: Water (0.02% TFA buffer); Solvent B: Acetonitrile (0.02% TFA buffer); Solvent Gradient: Time 0: 5% B; 2.5 min: 5% B; 7 min: 95% B; Hold 95% B 5 min.

Flow Rate: 22.5 mL/min

The product peak was collected based on UV absorption and concentrated.

Note 2: Analytical LCMS Conditions:

Hewlett Packard 1100 MSD with ChemStation Software

Column: YMC ODS-AM 2.0 mm×50 mm 5μ column at 50° C.

Solvent A: Water (0.02% formic acid buffer)

Solvent B: Acetonitrile (0.02% formic acid buffer)

Gradient: Time 0: 5% B; 0.3 min: 5% B; 3.0 min: 95% B; Hold 95% B 2 min.

Flow rate 1.0 mL/min

Detection: 254 nm DAD; API-ES Scanning Mode Negative 150–700; Fragmentor 70 mV.

Following the procedure described in Steps 1–4 of Example 45, and using 5-bromoindole, 3-chlorophenyl boronic acid, 4-methoxyphenylboronic acid, 4-trifluoromethylphenylboronic acid, or 3-trifluorophenylboronic acid, and cyclopentanol, cyclohexylmethanol, cyclobutylmethanol, 3-methylcyclopentanol, or cyclopentylpropanol, compounds of Examples 46–59 were prepared:

EXAMPLE 46

[5-(3-chlorophenyl)-1-(cyclobutylmethyl)-1H-indol-3-yl](oxo)acetic acid (LCMS$^2$ Data: Molecular ion and retention time): 366 (M–H); 3.02 min.

EXAMPLE 47

[5-(3-chlorophenyl)-1-(3-methylcyclopropyl)-1H-indol-3-yl](oxo)acetic acid (LCMS$^2$ Data: Molecular ion and retention time): 380 (M–H); 3.15 min.

EXAMPLE 48

[5-(3-chlorophenyl)-1-(cyclohexylmethyl)-1H-indol-3-yl](oxo)acetic acid (LCMS$^2$ Data: Molecular ion and retention time): 394 (M–H); 3.37 min.

EXAMPLE 49

[5-(4-trifluoromethylphenyl)-1-(cyclopentyl)-1H-indol-3-yl](oxo)acetic acid (LCMS$^2$ Data: Molecular ion and retention time): 400 (M–H); 3.06 min.

EXAMPLE 50

[5-(4-trifluoromethylphenyl)-1-(cyclobutylmethyl)-1H-indol-3-yl](oxo)acetic acid (LCMS$^2$ Data: Molecular ion and retention time): 400 (M–H); 3.10 min.

EXAMPLE 51

[5-(4-trifluoromethylphenyl)-1-(3-methylcyclopentyl)-1H-indol-3-yl](oxo)acetic acid (LCMS$^2$ Data: Molecular ion and retention time): 414 (M–H); 3.22 min.

EXAMPLE 52

[5-(4-trifluoromethylphenyl)-1-(cyclohexylmethyl)-1H-indol-3-yl](oxo)acetic acid (LCMS$^2$ Data: Molecular ion and retention time): 428 (M–H); 3.36 min.

EXAMPLE 53

[5-(4-trifluoromethylphenyl)-1-(cyclopentylpropyl)-1H-indol-3-yl](oxo)acetic acid (LCMS$^2$ Data: Molecular ion and retention time): 442 (M–H); 3.53 min.

EXAMPLE 54

[5-(3-trifluoromethylphenyl)-1-(cyclopentyl)-1H-indol-3-yl](oxo)acetic acid (LCMS$^2$ Data: Molecular ion and retention time): 400 (M–H); 3.08 min.

EXAMPLE 55

[5-(3-trifluoromethylphenyl)-1-(cyclobutylmethyl)-1H-indol-3-yl](oxo)acetic acid (LCMS$^2$ Data: Molecular ion and retention time): 400 (M–H); 3.08 min.

EXAMPLE 56

[5-(3-trifluoromethylphenyl)-1-(3-methylcyclopentyl)-1H-indol-3-yl](oxo)acetic acid (LCMS$^2$ Data: Molecular ion and retention time): 414 (M–H); 3.22 min.

EXAMPLE 57

[5-(3-trifluoromethylphenyl)-1-(cyclohexylmethyl)-1H-indol-3-yl](oxo)acetic acid (LCMS$^2$ Data: Molecular ion and retention time): 428 (M–H); 3.35 min.

EXAMPLE 58

[5-(3-trifluoromethylphenyl)-1-(cyclopentylpropyl)-1H-indol-3-yl](oxo)acetic acid (LCMS$^2$ Data: Molecular ion and retention time): 442 (M–H); 3.51 min.

Compound of Example 58 was resynthesized on a larger scale and purified by preparative HPLC to give a yellow solid: $^1$H NMR (d$_6$-DMSO, 400 MHz) δ 0.95–1.20 (m, 5H), 1.50–1.71 (M, 5H), 1.78–1.90 (m, 1H), 4.22 (d, J=6.9 Hz, 2H), 7.43 (d, J=6 Hz, 1H), 7.52 (t, J=7.9 Hz, 1H), 7.65 (d, J=8.36, 2H), 7.70 (s, 1H), 7.79 (d, J=8.6 Hz, 1H), 8.43 (s, 1H), 8.50 (s, 1H). Mass spectrum: (ESI, [M+H]$^+$): m/z 396

EXAMPLE 59

[5-(4-methoxyphenyl)-1-(cyclohexylmethyl)-1H-indol-3-yl](oxo)acetic acid (LCMS$^2$ Data: Molecular ion and retention time): 390 (M–H); 2.88 min.

EXAMPLE 60

1-Methyl-6-(4-trifluoromethyl-phenyl)-1H-indole-3-carboxylic acid

To a solution of 1-methyl-6-(4-trifluoromethyl-phenyl)-1H-indole (0.483 g, 1.75 mmol) in dry THF (10 mL) at −78° C. was added n-butyllithium (0.84 mL, 2.1 mmol). The reaction mixture was stirred under nitrogen at −78° C. for 30 minutes then at −50 to −40° C. for 30 minutes. It reaction temperature was cooled to −78° C. and crushed dry ice (3.5 g, 80 mmol) was added. The reaction mixture was stirred overnight at room temperature. It was then concentrated and partitioned in 2N hydrochloric acid and ethyl acetate. The organic phase was washed with water and brine, dried over anhydrous magnesium sulfate and evaporated to dryness.

The residue was purified by flash chromatography using 10–50% ethyl aceate in hexane as an eluant. The title compound was obtained as a yellow solid (0.108 g, 19%), mp: 237–239° C. (dec). Mass spectrum (–APCI, [M–H]⁻) m/z 318. ¹HNMR (400 MHz, DMSO-$d_6$): δ 12.8–13.2 (br s, 1H), 8.0 (d, 2H, J=8.1 Hz), 7.95 (s, 1H), 7.75–7.85 (m, 3H), 7.5 (dd, 1H, J=8.3 and 1.5 Hz), 7.25 (s, 1H), and 4.10 ppm (s, 3H).

Elemental Analysis for $C_{17}H_{12}F_3NO_2$: Calculated: C, 63.95; H, 3.79; N, 4.39. Found: C, 63.86; H, 3.55; N, 4.34.

EXAMPLE 61

6-(4-tert-Butyl-phenyl)-1-methyl-1H-indole-3-carboxylic acid 6-(4-tert-Butyl-phenyl)-1-methyl-1H-indole-3-carboxylic acid was prepared from 6-(4-tert-butyl-phenyl)-1-methyl-1H-indole (0.541 g, 2.05 mmol), n-butyllithium (0.98 mL, 2.5 mmol), crushed dry ice (3 g, 70 mmol) in dry THF (10 mL) according to the procedure described in Example 60. Purification by flash chromatography using 10–50% ethyl acetate in hexane and 100% ethyl acetate as eluants afforded the title compound as a light yellow solid (0.0675 g, 10.7%), mp: 236–238° C. (dec.). Mass spectrum (–APCI, [M–H]⁻) m/z 306. ¹HNMR (400 MHz, DMSO-$d_6$): δ 12.8–13.0 (br s, 1H), 7.8 (s, 1H), 7.65–7.7 (m, 3H), 7.45–7.5 (m, 2H), 7.4 (dd, 1H, J=8.3 Hz and 1.6 Hz), 7.2 (d, 1H, J=0.75 Hz), 4.05 (s, 3H) and 1.35 ppm (s, 9H).

Elemental Analysis for $C_{20}H_{21}NO_2$: Calculated: C, 78.15; H, 6.89; N, 4.56. Found: C, 77.82; H, 6.89; N, 4.42.

EXAMPLE 62

1-Benzyl-5-(3-chloro-4-fluoro-phenyl)-1H-indole-3-carboxylic acid

1-Benzyl-5-(3-chloro-4-fluoro-phenyl)-1H-indole-3-carboxylic acid was prepared from 1-benzyl-5-(3-chloro-4-fluorophenyl)-1H-indole (17.99 g, 53.6 mmol), n-butyllithium (26 mL, 65 mmol), crushed dry ice (20 g, 450 mmol) in dry THF (180 mL) according to the procedure described in Example 60. Purification by HPLC using 85% acetonitrile in water as the mobile phase afforded the title compound as a light pink solid (6.51 g, 32%), mp: 189–194° C. Mass spectrum (+APCI, [M+H]⁺) m/z 380. ¹HNMR (400 MHz, DMSO-$d_6$): δ 13.5–13.8 (br s, 1H), 8.05 (dd, 1H, J=6.5 Hz and 2.6 Hz), 8.0 (dd, 1H, J=6.1 Hz and 2.4 Hz ), 7.9 (d, 1H, J=1.5 Hz), 7.5–7.55 (m, 2H), 7.4 (dd, 1H, J=8.5 Hz and 2.0 Hz), 7.3–7.35 (m, 2H), 7.2–7.25 (m, 3H), 6.55 (dd, 1H, J=3.2 Hz and 0.75 Hz) and 5.45 ppm (s, 2H).

Elemental Analysis for $C_{22}H_{15}ClFNO_2$: Calculated: C, 69.57; H, 3.98; N, 3.69. Found: C, 69.87; H, 3.83; N, 3.69.

EXAMPLE 63

[1-Methyl-5-(4-trifluoromethyl-phenyl)-1H-indol-3-yl]-acetic acid

Step 1

(5-Bromo-1H-indol-3-ylmethyl)-dimethyl-amine

To a mixture of 40% aqueous dimethylamine (5.95 g, 52.8 mmol), 37% aqueous formaldehyde (4.21 g, 51.9 mmol) and acetic acid (7 mL) was added 5-bromo-1H-indole (9.79 g, 49.9 mmol). The reaction mixture was stirred for 21 hours at room temperature and poured into a 2.5 N sodium hydroxide/ice mixture (200 mL). This was extracted with ethyl acetate, washed with water and brine, dried over magnesium sulfate and evaporated to dryness. It was dried at 60° C. for 30 minutes to yield (5-bromo-1H-indol-3-ylmethyl)-dimethyl-amine (11.2 g) as a brown solid: mp 160–162° C. ¹HNMR (200 MHz, DMSO-$d_6$): δ 11.1 (br s, 1H), 7.75 (s, 1H), 7.15–7.35 (m, 3H), and 3.5 ppm (s, 2H).

Step 2

(5-Bromo-1H-indol-3-yl)-acetonitrile

To an ice cooled suspension of (5-bromo-1H-indol-3-ylmethyl)-dimethyl-amine (11.2 g, 44.1 mmol) in benzene (145 mL) was added iodomethane (8.2 mL, 130 mmol). The reaction mixture was stirred overnight at room temperature and concentrated. The residue was dissolved in THF (210 mL). Trimethylsilyl cyanide (11.7 mL, 87.7 mmol) and tetrabutylammonium fluoride (140 mL, 140 mmol of a 1.0 M solution in THF) were added. After stirring for 2.5 hours, at room temperature, water (12 mL) was added. The mixture was partially concentrated. The residue was partitioned in ethyl acetate and water. The organic phase was washed with water and brine, dried over anhydrous magnesium sulfate and evaporated to dryness. Purification by flash chromatography using 15–35% ethyl acetate in hexane as an eluant afforded (5-bromo-1H-indol-3-yl)-acetonitrile (5.30 g, 51%) as a mauve solid, mp 105–106° C. ¹HNMR (300 MHz, DMSO-$d_6$): δ 11.35 (s, 1H), 7.8 (d, 1H, J=2.2 Hz), 7.35–7.45 (m, 2H), 7.2–7.3 (m, 1H), and 4.0 ppm (s, 2H).

Step 3

[5-(4-Trifluoromethyl-phenyl)-1H-indol-3-yl]-acetonitrile 5-bromo-1H-indol-3-yl)-acetonitrile (1.94 g, 8.25 mmol) was coupled to 4-trifluoromethylphenylboronic acid (2.04 g, 10.7 mmol), using [1,1'-bis(diphenylphosphino)ferrocene]dichloropalladium (II) complex with dichloromethane (1:1) (0.331 g, 0.405 mmol), and potassium carbonate (2.30 g, 16.6 mmol), in dioxane (83 mL) and water (8.3 mL), according to the procedure described in Step 1 of Example 11. Purication by HPLC using 40% (6% MTBE in methylene chloride) in hexane as the mobile phase yielded the title compound as a white solid (0.872 g, 35%). ¹HNMR (300 MHz, DMSO-$d_6$): δ 11.3 (s, 1H), 8.0 (s, 1H), 7.9 (d, 2H, J=8.8 Hz), 7.8 (d, 2H, J=8.8 Hz), 7.55 (s, 2H), 7.45 (s, 1H), and 4.1 ppm (s, 2H).

Step 4

[1-Methyl-5-(4-trifluoromethyl-phenyl)-1H-indol-3-yl]-acetonitrile

[1-Methyl-5-(4-trifluoromethyl-phenyl)-1H-indol-3-yl]-acetonitrile was prepared from [5-(4-trifluoromethyl-phenyl)-1H-indol-3-yl]-acetonitrile (0.377 g, 1.26 mmol), sodium hydride (0.117 g, 2.93 mmol of a 60% dispersion on mineral oil), iodomethane ( 0.17 mL, 2.8 mmol) and THF (10 mL) according to the procedure described in Step 2 of Example 1. Purification by flash chromatography using 5–15% ethyl acetate in hexane as an eluant afforded the title compound as a yellow semi-solid (0.237 g, 60%), ¹HNMR (300 MHz, DMSO-$d_6$): δ 8.0 (s, 1H), 7.9 (d, 2H, J=7.7 Hz), 7.8 (d, 2H, J=7.7 Hz), 7.6 (s, 2H), 7.45 (s, 1H) 4.15 (s, 2H) and 3.8 ppm (s, 3H).

Step 5

[1-Methyl-5-(4-trifluoromethyl-phenyl)-1H-indol-3-yl]-acetic acid

The mixture of [1-methyl-5-(4-trifluoromethyl-phenyl)-1H-indol-3-yl]-acetonitrile (0.230 g, 0.732 mmol), potassium hydroxide (2.16 g, 38.5 mmol), methanol (5 mL) and water (5 mL) was heated at refluxed for 24 hours. The reaction mixture was cooled to room temperature and concentrated. Water was added and the mixture was acidified with 2N hydrochloric acid. The mixture was extracted with ethyl acetate, washed with water and brine, dried over anhydrous magnesium sulfate and evaporated to dryness. Purification of the residue by HPLC using 4% methanol in methylene chloride as the mobile phase afforded the title compound as a light brown solid (0.0598 g, 25%), mp 167–168° C. Mass spectrum (+APCI, [M+H]+) m/z 334. ¹HNMR (400 MHz, DMSO-d₆): δ 12.1–12.4 (br s, 1H), 7.9 (d, 3H, J=7.8 Hz), 7.8 (d, 2H, J=8.1 Hz), 7.55 (d, 2H, J=1.2 Hz), 7.3 (s, 1H), 3.8 (s, 3H) and 3.7 ppm (s, 2H).

Elemental Analysis for $C_{18}H_{14}F_3NO_2$: Calculated: C, 64.86; H, 4.23; N, 4.20. Found: C, 64.88; H, 4.17; N, 4.03.

EXAMPLE 64

2-[1-[4-(tert-Butyl)benzyl]-5-(3-methylphenyl)-1H-indol-3-yl]-acetic acid

Hydrazine monohydrate (0.56 mL, 11.75 mmol) was added to a stirring solution of 2-[1-[4-(tert-Butyl)benzyl]-5-(3-methylphenyl)-1H-indol-3-yl]-2-oxoacetic acid (WAY-201417, 1.0 g, 2.35 mmol) in 2-methoxyethanol (10 mL). After the mixture was heated to 60° C. Sodium methoxide (1.34 g, 23.5 mmol) was added portionwise to the mixture. The reaction mixture was then slowly heated to 150° C., and concentrated. The mixture was kept stirring at 150° C. for 1 hour. The reaction mixture was cooled and poured onto ice water (100 mL). The aqueous mixture was extracted with methylene chloride and acidified with concentrated hydrocloric acid at 0° C. The organic extracts were washed with water and brine. Evaporation of the solvent and purification by flash column chromatography (5% methanol in methylene chloride) afforded an orange solid (0.452 g), m.p. 91–92° C. Mass spectrum [+ESI, (M+H)+] m/z 412. ¹H NMR (400 MHz, DMSO-d₆) δ 12.00 (br s, 1H), 7.75 (s, 1H), 7.51 (d, 1H, J=8.55 Hz), 7.45 (s, 1H), 7.42–7.37 (m, 3H), 7.32–7.29 (m, 3H), 7.15 (d, 2H, J=8.25 Hz), 7.19 (d, 1H, J=7.48 Hz), 5.34 (s, 2H), 3.70 (s, 2H), 2.37 (s, 3H), and 1.22 ppm (s, 9H).

Elemental Analysis for $C_{28}H_{27}NO_3 \cdot 0.1H_2O$: Calculated: C, 81.36; H, 7.12; N, 3.39. Found: C, 81.15; H, 6.76; N, 3.52.

EXAMPLE 65

{1-(4-Methylbenzyl)-5-[4-(trifluoromethoxy)phenyl]-1H-indol-3-yl}acetic acid

The title compound was prepared from {1-(4-methylbenzyl)-5-[4-(trifluoromethoxy)phenyl]-1H-indol-3-yl}(oxo)acetic acid, hydrazine monohydrate and sodium methoxide according to the procedure described in Example 64. The product was obtained as a brown solid, mp: 62–63° C. Mass spectrum (-ESI, [M–H]⁻) m/z 438. ¹HNMR (400 MHz, DMSO-d₆): δ 7.79 (s, 1H), 7.75 (d, 2H, J=8.70 Hz), 7.50 (d, 1H, J=8.56 Hz), 7.42–7.39 (m, 4H), 7.12 (d, 2H, J=8.55 Hz), 7.11 (d, 2H, J=8.55 Hz), 5.34 (s, 2H), and 2.23 ppm (s, 3H).

Elemental Analysis for $C_{25}H_{20}F_3NO_3$: Calculated: C, 68.33; H, 4.59; N, 3.19. Found: C, 68.00; H, 4.59; N, 3.40.

What is claimed:

1. A compound of formula (I):

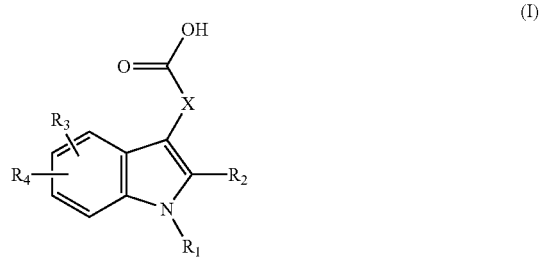

wherein:

X is —C(O)—;

$R_1$ is selected from $C_1$–$C_8$ alkyl, (—$CH_2$)$_n$–$C_3$–$C_6$ cycloalkyl, wherein n is an integer of from 0 to 3, pyridinyl, —$CH_2$-pyridinyl, phenyl or benzyl, the rings of the cycloalkyl, pyridinyl, phenyl and benzyl groups being optionally substituted by, from 1 to 3 groups selected from, halogen, $C_1$–$C_4$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$;

$R_2$ is selected from H, $C_1$–$C_6$ alkyl, $C_3$–$C_6$ cycloalkyl, —$CH_2$—$C_3$–$C_6$ cycloalkyl, or $C_1$–$C_3$ perfluoroalkyl, preferably —$CF_3$, —$CH_2OH$ or $CH_2OAc$;

$R_3$ is selected from H, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, $C_3$–$C_6$ cycloalkenyl, —$CH_2$—$C_3$–$C_6$ cycloalkenyl, —$NH_2$, or —$NO_2$;

$R_4$ is phenyl, substituted by from 1 to 3 groups selected from halogen, $C_1$–$C_4$ alkyl, $C_1$–$C_3$ perfluoroalkyl, —O—$C_1$–$C_3$ perfluoroalkyl, $C_1$–$C_3$ alkoxy, —OH, —$NH_2$, —$NO_2$ or (CO)$C_1$–$C_6$ alkyl, or a pharmaceutically acceptable salt or ester form thereof.

2. A compound of claim 1 of the formula:

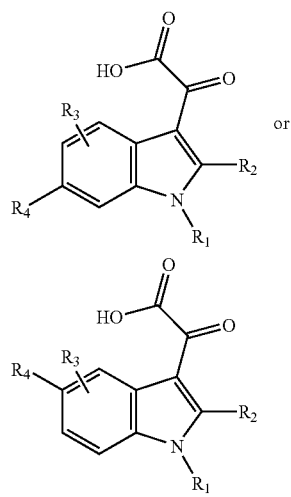

wherein $R_1$, $R_2$, $R_3$ and $R_4$ are as defined in claim 1, or a pharmaceutically acceptable salt or ester form thereof.

3. A compound of claim 1 of the formula:

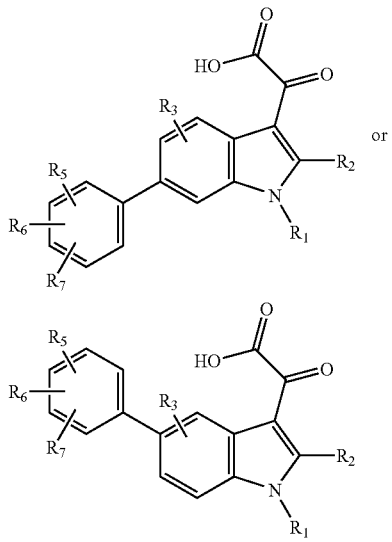

wherein:
R₁ is selected from $C_1$–$C_8$ alkyl, $C_3$–$C_6$ cycloalkyl, —CH₂—$C_3$–$C_6$ cycloalkyl, or benzyl, the rings of the cycloalkyl and benzyl groups being optionally substituted by from 1 to 3 groups selected from halogen, $C_1$–$C_4$ alkyl, $C_1$–$C_3$ perfluoroalkyl, —O—$C_1$–$C_3$ perfluoroalkyl, $C_1$–$C_3$ alkoxy, —OH, —NH₂, or —NO₂;
R₂ is selected from H, $C_1$–$C_6$ alkyl, $C_3$–$C_6$ cycloalkyl, —CH₂—$C_3$–$C_6$ cycloalkyl, or $C_1$–$C_3$ perfluoroalkyl;
R₃ is selected from H, halogen, $C_1$–$C_6$ alkyl, $C_1$–$C_3$ perfluoroalkyl, $C_1$–$C_6$ alkoxy, $C_3$–$C_6$ cycloalkyl, —CH₂—$C_3$–$C_6$ cycloalkyl, —NH₂, or —NO₂;
R₅ and R₆ are independently selected from H, halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH₂, or —NO₂; and
R₇ is selected from halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH₂, or —NO₂;
or a pharmaceutically acceptable salt or ester form thereof.

4. A compound of claim 1 which is selected from the group of:
a) {1-Methyl-6-[4-(trifluoromethoxy)phenyl]-1H-indol-3-yl}(oxo)acetic acid;
b) {1-Methyl-6-[4-(trifluoromethyl)phenyl]-1H-indol-3-yl}(oxo)acetic acid;
c) {1-Ethyl-6-[4-(trifluoromethoxy)phenyl]-1H-indol-3-yl}(oxo)acetic acid;
d) {1-Ethyl-6-[4-(trifluoromethyl)phenyl]-1H-indol-3-yl}(oxo)acetic acid; or
e) {1-Benzyl-6-[4-(trifluoromethoxy)phenyl]-1H-indol-3-yl}(oxo)acetic acid;
or a pharmaceutically acceptable salt or ester form thereof.

5. A compound of claim 1 which is selected from the group of:
a) {1-Benzyl-6-[4-(trifluoromethyl)phenyl]-1H-indol-3-yl}(oxo)acetic acid;
b) {1-[4-(tert-Butyl)benzyl]-6-[4-(trifluoromethyl)phenyl]-1H-indol-3-yl}(oxo)acetic acid;
c) {1-[4-(tert-Butyl)benzyl]-6-[4-(trifluoromethoxy)phenyl]-1H-indol-3-yl}(oxo)acetic acid;
d) {1-Benzyl-5-[4-(trifluoromethyl)phenyl]-1H-indol-3-yl}(oxo)acetic acid; or
e) {6-[4-(tert-Butyl)phenyl]-1-methyl-1H-indol-3-yl}(oxo)acetic acid;
or a pharmaceutically acceptable salt or ester form thereof.

6. A compound of claim 1 which is selected from the group of:
a) [5-(4-Acetylphenyl)-1-benzyl-1H-indol-3-yl](oxo)acetic acid;
b) {1-Benzyl-5-[4-(trifluoromethoxy)phenyl]-1H-indol-3-yl}(oxo)acetic acid;
c) {1-Benzyl-4-[4-(trifluoromethyl)phenyl]-1H-indol-3-yl}(oxo)acetic acid;
d) {1-Benzyl-5-[4-(tert-butyl)phenyl]-1H-indol-3-yl}(oxo)acetic acid; or
e) [1-Benzyl-5-(3-chloro-4-fluorophenyl)-1H-indol-3-yl](oxo)acetic acid;
or a pharmaceutically acceptable salt or ester form thereof.

7. A compound of claim 1 which is selected from the group of:
a) {1-Benzyl-5-[3,5-bis(trifluoromethyl)phenyl]-1H-indol-3-yl}(oxo)acetic acid;
b) {1-Benzyl-7-[4-(trifluoromethoxy)phenyl]-1H-indol-3-yl}(oxo)acetic acid;
c) [1-Benzyl-7-(3-chloro-4-fluorophenyl)-1H-indol-3-yl](oxo)acetic acid;
d) {1-(4-tert-Butylbenzyl)-5-[4-(trifluoromethoxy)phenyl]-1H-indol-3-yl}(oxo)acetic acid; or
e) {1-Benzyl-4-[4-(trifluoromethoxy)phenyl]-1H-indol-3-yl}(oxo)acetic acid;
or a pharmaceutically acceptable salt or ester form thereof.

8. A compound of claim 1 which is selected from the group of:
a) [1-Benzyl-6-(3-chlorophenyl)-1H-indol-3-yl](oxo)acetic acid; or
b) {1-Benzyl-5-[3-(trifluoromethoxy)phenyl]-1H-indol-3-yl}(oxo)acetic acid;
or a pharmaceutically acceptable salt or ester form thereof.

9. A compound of claim 1 which is selected from the group of:
a) {1-(4-Methylbenzyl)-5-[4-(trifluoromethoxy)phenyl]-1H-indol-3-yl}(oxo)acetic acid;
b) {1-(4-Fluorobenzyl)-5-[4-(trifluoromethoxy)phenyl]-1H-indol-3-yl}(oxo)acetic acid;
c) [1-Butyl-5-(4-chlorophenyl)-1H-indol-3-yl](oxo)acetic acid; or
d) [1-Butyl-5-(3-chlorophenyl)-1H-indol-3-yl](oxo)acetic acid;
or a pharmaceutically acceptable salt or ester form thereof.

10. A compound of claim 1 which is selected from the group of:
a) [1-Butyl-5-(3-methoxyphenyl)-1H-indol-3-yl](oxo)acetic acid;
b) [1-Butyl-5-(4-methoxyphenyl)-1H-indol-3-yl](oxo)acetic acid;
c) {1-Butyl-5-[4-(trifluoromethyl)phenyl]-1H-indol-3-yl}(oxo)acetic acid;
d) [1-(4-tert-Butylbenzyl)-5-(3-methylphenyl)-1H-indol-3-yl](oxo)acetic acid; or
e) [1-(4-tert-Butylbenzyl)-5-(3-methoxyphenyl)-1H-indol-3-yl](oxo)acetic acid
or a pharmaceutically acceptable salt or ester form thereof.

11. A compound of claim 1 which is selected from the group of:
   a) [1-(4-tert-Butylbenzyl)-5-(4-tert-butylphenyl)-1H-indol-3-yl](oxo)acetic acid;
   b) [1-(4-tert-Butylbenzyl)-5-(3-chlorophenyl)-1H-indol-3-yl](oxo)acetic acid;
   c) [1-(4-tert-Butylbenzyl)-5-(4-chlorophenyl)-1H-indol-3-yl](oxo)acetic acid;
   d) [1-(4-tert-Butylbenzyl)-5-(2-methylphenyl)-1H-indol-3-yl](oxo)acetic acid; or
   e) {1-(2-Ethylbutyl)-5-[4-(trifluoromethoxy)phenyl]-1H-indol-3-yl}(oxo)acetic acid;

or a pharmaceutically acceptable salt or ester form thereof.

12. A compound of claim 1 which is selected from the group of:
   a) {2-[(Acetyloxy)methyl]-1-(4-methylbenzyl)-5-[4-(trifluoromethoxy)phenyl]-1H-indol-3-yl}(oxo)acetic acid;
   b) {2-(Hydroxymethyl)-1-(4-methylbenzyl)-5-[4-(trifluoromethoxy)phenyl]-1H-indol-3-yl}(oxo)acetic acid;
   c) {2-[(Acetyloxy)methyl]-1-benzyl-5-[4-(trifluoromethoxy)phenyl]-1H-indol-3-yl}(oxo)acetic acid;
   d) {1-Benzyl-2-(hydroxymethyl)-5-[4-(trifluoromethoxy)phenyl]-1H-indol-3-yl}(oxo)acetic acid; or
   e) [5-(3-Chlorophenyl)-1-cyclopentyl-1H-indol-3-yl]-oxo-acetic acid;

or a pharmaceutically acceptable salt or ester form thereof.

13. A compound of claim 1 which is selected from the group of:
   a) [5-(3-chlorophenyl)-1-(cyclobutylmethyl)-1H-indol-3-yl](oxo)acetic acid;
   b) [5-(3-chlorophenyl)-1-(3-methylcyclopropyl)-1H-indol-3-yl](oxo)acetic acid;
   c) [5-(3-chlorophenyl)-1-(cyclohexylmethyl)-1H-indol-3-yl](oxo)acetic acid;
   d) [5-(4-trifluoromethylphenyl)-1-(cyclopentyl)-1H-indol-3-yl](oxo)acetic acid; or
   e) [5-(4-trifluoromethylphenyl)-1-(cyclobutylmethyl)-1H-indol-3-yl](oxo)acetic acid; or a pharmaceutically acceptable salt or ester form thereof.

14. A compound of claim 1 which is selected from the group of:
   a) [5-(4-trifluoromethylphenyl)-1-(3-methylcyclopentyl)-1H-indol-3-yl](oxo)acetic acid;
   b) [5-(4-trifluoromethylphenyl)-1-(cyclohexylmethyl)-1H-indol-3-yl](oxo)acetic acid;
   c) [5-(4-trifluoromethylphenyl)-1-(cyclopentylpropyl)-1H-indol-3-yl](oxo)acetic acid;
   d) [5-(3-trifluoromethylphenyl)-1-(cyclopentyl)-1H-indol-3-yl](oxo)acetic acid; or
   e) [5-(3-trifluoromethylphenyl)-1-(cyclobutylmethyl)-1H-indol-3-yl](oxo)acetic acid; or a pharmaceutically acceptable salt or ester form thereof.

15. A compound of claim 1 which is selected from the group of:
   a) [5-(3-trifluoromethylphenyl)-1-(3-methylcyclopentyl)-1H-indol-3-yl](oxo)acetic acid;
   b) [5-(3-trifluoromethylphenyl)-1-(cyclohexylmethyl)-1H-indol-3-yl](oxo)acetic acid;
   c) [5-(3-trifluoromethylphenyl)-1-(cyclopentylpropyl)-1H-indol-3-yl](oxo)acetic acid; or
   d) [5-(4-methoxyphenyl)-1-(cyclohexylmethyl)-1H-indol-3-yl](oxo)acetic acid;

or a pharmaceutically acceptable salt or ester form thereof.

16. A pharmaceutical composition comprising pharmaceutically effective amount of a compound of claim 1, or a pharmaceutically acceptable salt or ester form thereof, and a pharmaceutically acceptable excipient or carrier.

17. A compound of claim 1 wherein
   $R_1$ is $C_1$–$C_6$ alkyl, $(—CH_2)_n$—$C_3$–$C_6$ cycloalkyl, wherein n is an integer of from 0 to 3, pyridinyl, —CH$_2$-pyridinyl, phenyl or benzyl, the rings of the cycloalkyl, pyridinyl, phenyl and benzyl groups being optionally substituted by, from 1 to 3 groups selected from, halogen, $C_1$–$C_4$ alkyl, —CF$_3$, —O—CF$_3$, $C_1$–$C_3$ alkoxy, —OH, —NH$_2$, or —NO$_2$;
   $R_2$ is H, $C_1$–$C_6$ alkyl, $C_3$–$C_6$ cycloalkyl, —CH$_2$—$C_3$–$C_6$ cycloalkyl, —CF$_3$, —CH$_2$OH or CH$_2$OAc; and
   $R_3$ is H, halogen, $C_1$–$C_6$ alkyl, —CF$_3$, $C_1$–$C_6$ alkoxy, $C_3$–$C_6$ cycloalkyl, —CH$_2$—$C_3$–$C_6$ cycloalkyl, $C_3$–$C_6$ cycloalkenyl, —CH$_2$—$C_3$–$C_6$ cycloalkenyl, —NH$_2$, or —NO$_2$;

or a pharmaceutically acceptable salt or ester form thereof.

18. A compound of claim 3 wherein
   $R_2$ is H, $C_1$–$C_6$ alkyl, $C_3$–$C_6$ cycloalkyl, —CH$_2$—$C_3$–$C_6$ cycloalkyl, or —CF$_3$; and
   $R_3$ is H, halogen, $C_1$–$C_6$ alkyl, —CF$_3$, $C_1$–$C_6$ alkoxy, $C_3$–$C_6$ cycloalkyl, —CH$_2$—$C_3$–$C_6$ cycloalkyl, —NH$_2$, or —NO$_2$;

or a pharmaceutically acceptable salt or ester form thereof.

19. A compound of claim 1 that is {1-Benzyl-5-[4-(trifluoromethoxy)phenyl]-1H-indol-3-yl}(oxo)acetic acid or a pharmaceutically acceptable salt or ester form thereof.

20. A compound of claim 1 that is [1-(4-tert-Butylbenzyl)-5-(3-methylphenyl)-1H-indol-3-yl](oxo)acetic acid or a pharmaceutically acceptable salt or ester form thereof.

21. A pharmaceutical composition comprising pharmaceutically effective amount of a compound of claim 19, or a pharmaceutically acceptable salt or ester form thereof, and a pharmaceutically acceptable excipient or carrier.

22. A pharmaceutical composition comprising pharmaceutically effective amount of a compound of claim 20, or a pharmaceutically acceptable salt or ester form thereof, and a pharmaceutically acceptable excipient or carrier.

* * * * *

UNITED STATES PATENT AND TRADEMARK OFFICE
CERTIFICATE OF CORRECTION

PATENT NO.        : 7,074,817 B2                                    Page 1 of 4
APPLICATION NO.   : 10/174159
DATED             : July 11, 2006
INVENTOR(S)       : Hassan Mahmoud Elokdah et al.

It is certified that error appears in the above-identified patent and that said Letters Patent is hereby corrected as shown below:

Column 2,
Line 7, delete "carboxyyl, etc. cloalkenyl," and insert -- carboxyl, etc., cycloalkenyl, --.
Line 31, after "acyl" insert -- . --.

Column 5,
Line 3, delete "benzylzmine," and insert -- benzylamine --.
Line 10, delete "peperidine" and insert -- piperidine --.
Line 12, delete "N-(2-hyroxyethyl)" and insert -- N-(2-hydroxyethyl) --.

Column 7,
Line 27, delete "orginate" and insert -- originate --.

Column 8,
Line 59, delete "The" and insert -- the --.
Line 60, delete "Bromoindoles" and insert -- bromoindoles --.

Column 10,
Lines 1-56
"

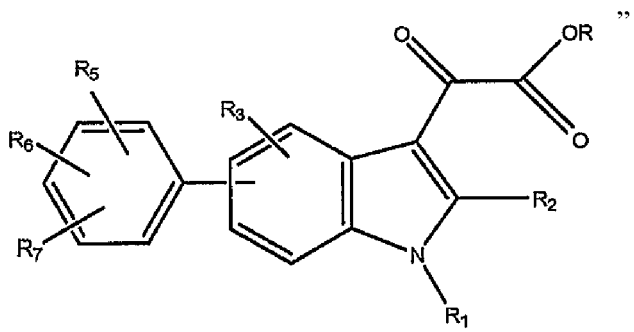

and insert
--

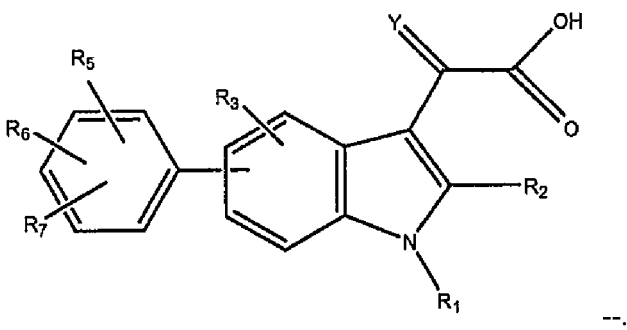

--.

UNITED STATES PATENT AND TRADEMARK OFFICE
CERTIFICATE OF CORRECTION

PATENT NO. : 7,074,817 B2
APPLICATION NO. : 10/174159
DATED : July 11, 2006
INVENTOR(S) : Hassan Mahmoud Elokdah et al.

It is certified that error appears in the above-identified patent and that said Letters Patent is hereby corrected as shown below:

Column 11,
Lines 17-28, delete
"

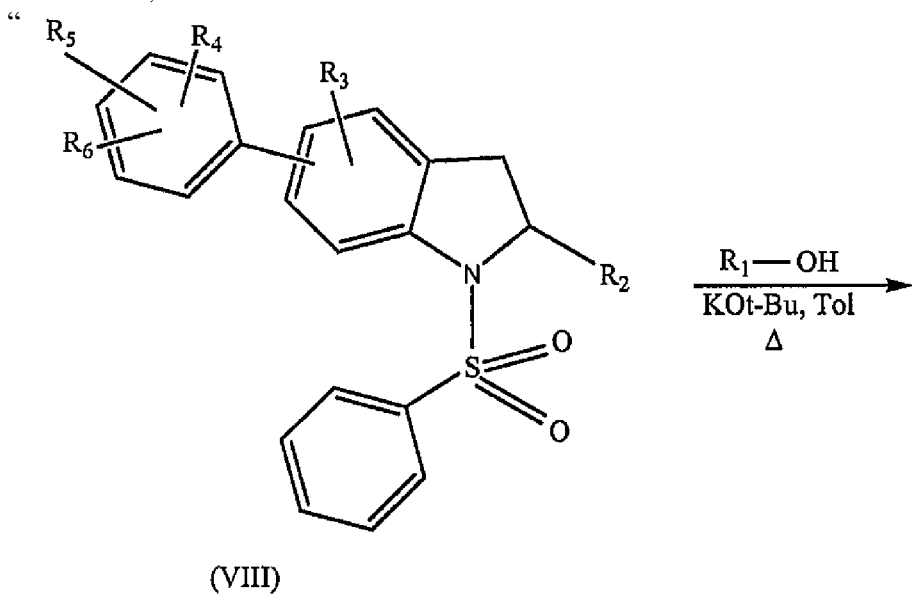

(VIII)
"

and insert
--

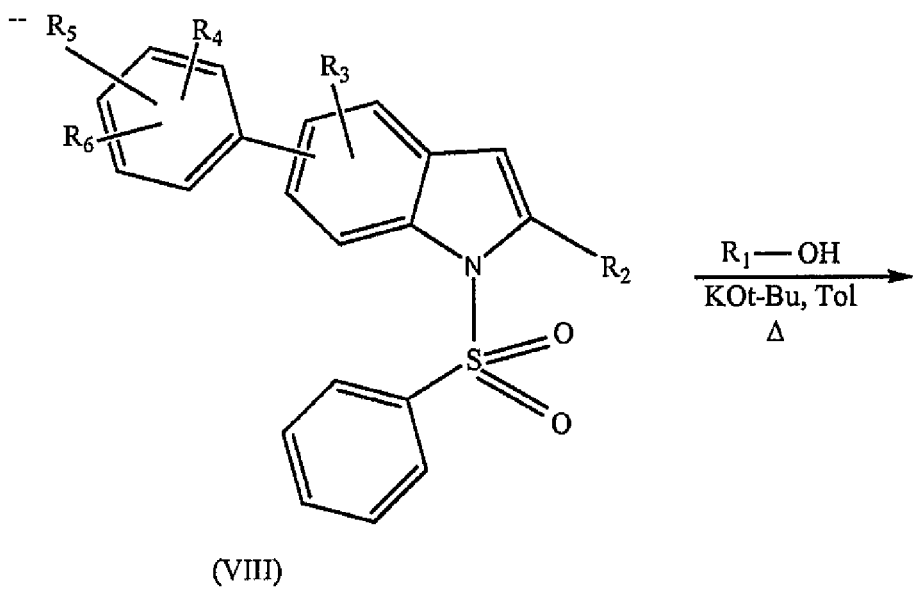

(VIII)
--.

UNITED STATES PATENT AND TRADEMARK OFFICE
CERTIFICATE OF CORRECTION

PATENT NO.         : 7,074,817 B2
APPLICATION NO. : 10/174159
DATED                 : July 11, 2006
INVENTOR(S)       : Hassan Mahmoud Elokdah et al.

Page 3 of 4

It is certified that error appears in the above-identified patent and that said Letters Patent is hereby corrected as shown below:

Lines 37-45, delete
"
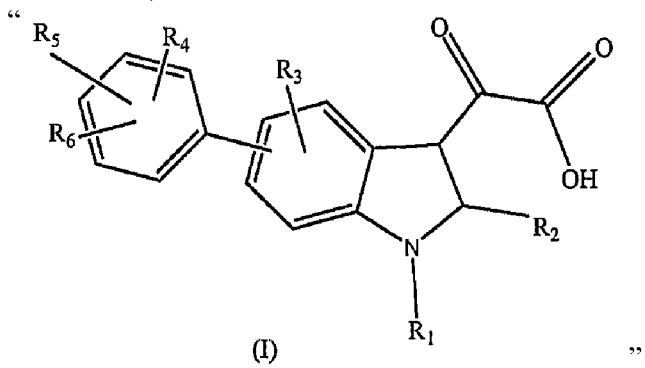
"

and insert

--
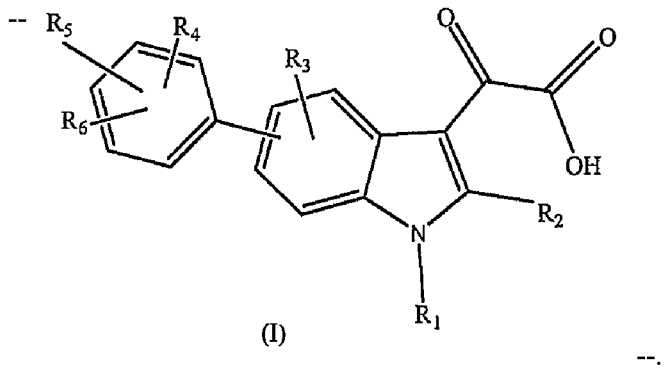
--.

Column 19,
Line 31, delete "4-trifuoromethoxybenzeneboronic" and insert
-- 4-trifluromethoxybenzeneboronic --.

Column 21,
Line 36, delete "phenyl]-1-H-indole" and insert -- phenyl]-1H-indole --.

Column 26,
Line 53, delete "1-Benzyl4-" and insert -- 1-Benzyl-4- --.

Column 27,
Line 39, delete "-Benzyl-" and insert -- 1-Benzyl- --.

UNITED STATES PATENT AND TRADEMARK OFFICE
CERTIFICATE OF CORRECTION

PATENT NO. : 7,074,817 B2
APPLICATION NO. : 10/174159
DATED : July 11, 2006
INVENTOR(S) : Hassan Mahmoud Elokdah et al.

It is certified that error appears in the above-identified patent and that said Letters Patent is hereby corrected as shown below:

Column 33,
Lines 2-3, delete "δ 6 7.75" and insert -- δ 7.75 --.
Line 48, delete "poritions" and insert -- portions --.

Column 37,
Line 20, delete "DMSO-d6):" and insert -- DMSO-$d_6$): --.

Column 41,
Line 36, delete "280.1 HNMR" and insert -- 280.   $^1$HNMR --.
Line 56, delete "H, 5,93;" and insert -- H, 5.93; --.

Column 48,
Line 30, delete "358.1 HNMR" and insert -- 358.   $^1$HNMR --.

Column 52,
Line 61, delete "It" and insert -- The --.

Column 56,
Line 30, delete "or".
Line 31, delete "preferably –$CF_3$,".
Line 37, after "phenyl" delete " ,".

Column 60,
Line 15, after "comprising" insert -- a --.
Line 47, after "comprising" insert -- a --.
Line 51, after "comprising" insert -- a --.

Signed and Sealed this

Tenth Day of July, 2007

JON W. DUDAS
*Director of the United States Patent and Trademark Office*